US012674145B2

(12) United States Patent
Li et al.

(10) Patent No.: US 12,674,145 B2
(45) Date of Patent: Jul. 7, 2026

(54) VECTOR GENETICALLY ENGINEERED WITH CHIMERIC ANTIGEN RECEPTOR AND AGAINST TWO OR MORE TARGETS AND APPLICATION THEREOF

(71) Applicant: SPH BIOTHERAPEUTICS (SHANGHAI) LIMITED., Shanghai (CN)

(72) Inventors: Benshang Li, Shanghai (CN); Tianyi Wang, Shanghai (CN); Xinyu Wan, Shanghai (CN); Xiaomin Yang, Shanghai (CN)

(73) Assignee: SPH BIOTHERAPEUTICS (SHANGHAI) LIMITED., Shanghai (CN)

( * ) Notice: Subject to any disclaimer, the term of this patent is extended or adjusted under 35 U.S.C. 154(b) by 578 days.

(21) Appl. No.: 18/251,264

(22) PCT Filed: Nov. 2, 2021

(86) PCT No.: PCT/CN2021/128240
§ 371 (c)(1),
(2) Date: May 1, 2023

(87) PCT Pub. No.: WO2022/089656
PCT Pub. Date: May 5, 2022

(65) Prior Publication Data
US 2023/0399627 A1 Dec. 14, 2023

(30) Foreign Application Priority Data

Nov. 2, 2020 (WO) ................ PCT/CN2020/125956

(51) Int. Cl.
*C12N 5/10* (2006.01)
*C12N 15/62* (2006.01)
*C12N 15/79* (2006.01)

(52) U.S. Cl.
CPC .............. *C12N 5/10* (2013.01); *C12N 15/62* (2013.01); *C12N 15/79* (2013.01); *C12N 2740/16032* (2013.01)

(58) Field of Classification Search
CPC .................... C12N 15/62; C12N 15/79; C12N 2740/16032; A61K 40/11; A61K 40/31;
(Continued)

(56) References Cited

U.S. PATENT DOCUMENTS

2020/0172879 A1* 6/2020 Suri ................... A61K 40/4215

FOREIGN PATENT DOCUMENTS

CN 108220247 A 6/2018
CN 108884167 A 11/2018
CN 110129369 A 8/2019

OTHER PUBLICATIONS

Dai, H., 2020. Bispecific CAR-T cells targeting both CD19 and CD22 for therapy of adults with relapsed or refractory B cell acute lymphoblastic leukemia. Journal of hematology & oncology, 13(1), p. 30. (Year: 2020).*

(Continued)

*Primary Examiner* — Jeremy C Flinders
*Assistant Examiner* — Masudur Rahman
(74) *Attorney, Agent, or Firm* — Merchant & Gould P.C.; Daniel J. Pereira

(57) ABSTRACT

Provided are a vector genetically engineered with a chimeric antigen receptor and against two or more targets for combined treatment of disease such as human tumors, a related immune cell and application thereof. The vector genetically engineered with a chimeric antigen receptor and the related immune cell have enhanced ability to kill target cells.

13 Claims, 21 Drawing Sheets

Specification includes a Sequence Listing.

(58) Field of Classification Search
CPC ............ A61K 40/4211; A61K 40/4212; A61K
2239/28; C07K 14/70517; C07K
14/70521; C07K 14/7051
See application file for complete search history.

(56) References Cited

OTHER PUBLICATIONS

Schultz, L.M., 2019. Phase I trial using CD19/CD22 bispecific CAR T cells in pediatric and adult acute lymphoblastic leukemia (All). Blood, 134, p. 744. (Year: 2019).*

International Search Report mailed on Feb. 9, 2022 in PCT/CN2021/128240 filed on Nov. 2, 2021 (4 pages).

Chu. Suxia et al. (Advances on the Study of Multi-gene Expression System), China Biotechnology, vol. 31. No. 6. Jun. 15, 2011 (Jun. 15, 2011). ISSN: 1671-8135. see pp. 116-121.

Gheybi. E et al. "Designing a recombinant chimeric construct contain MUC1 and HER2 extracellular domain for prediagnostic breast cancer", Tumor Biology, vol. 35, No. 11, Aug. 16, 2014 (Aug. 16, 2014), ISSN: 1010-4283, see pp. 11489-11496.

* cited by examiner

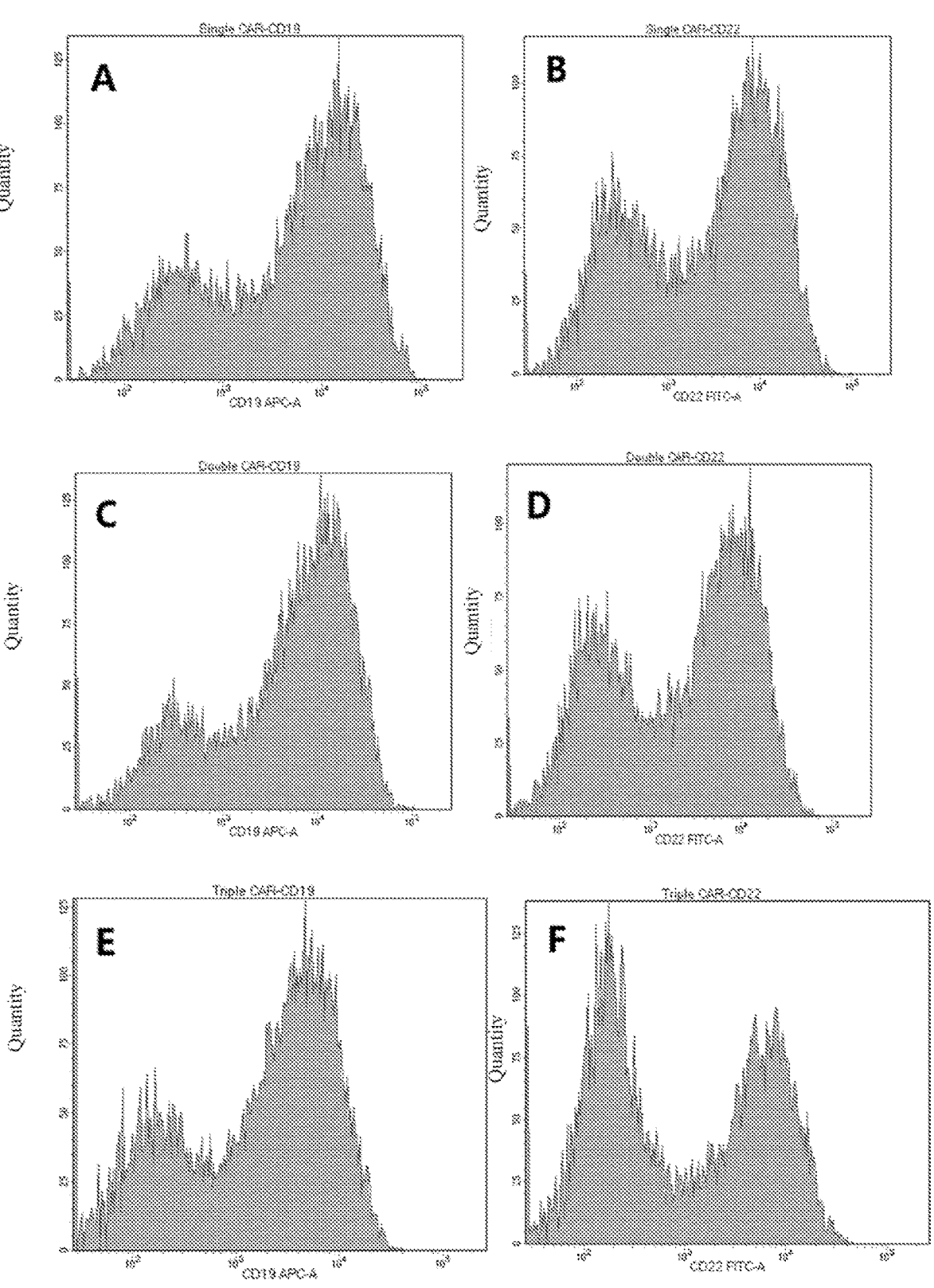
FIGs. 9A-F

Day18

SEQUENCE LISTING

<160> NUMBER OF SEQ ID NOS: 84

<210> SEQ ID NO 1
<211> LENGTH: 1172
<212> TYPE: DNA
<213> ORGANISM: Artificial Sequence
<220> FEATURE:
<223> OTHER INFORMATION: EF1-alpha

<400> SEQUENCE: 1

```
gtgcccgtca gtgggcagag cgcacatcgc ccacagtccc cgagaagttg ggggggagggg      60 tcggcaattg aaccggtgcc tagagaaggt ggcgcggggt aaactgggaa agtgatgtcg     120
tgtactggct ccgccttttt cccgagggtg ggggagaacc gtatataagt gcagtagtcg     180
ccgtgaacgt tcttttttcgc aacgggtttg ccgccagaac acaggtaagt gccgtgtgtg     240
gttcccgcgg gcctggcctc tttacgggtt atggcccttg cgtgccttga attacttcca     300
cctggctgca gtacgtgatt cttgatcccg agcttcgggt tggaagtggg tgggagagtt     360
cgaggccttg cgcttaagga gcccttcgc ctcgtgcttg agttgaggcc tggcctgggc     420
gctggggccg ccgcgtgcga atctggtggc accttcgcgc ctgtctcgct gctttcgata     480
agtctctagc catttaaaat ttttgatgac ctgctgcgac gctttttttc tggcaagata     540
gtcttgtaaa tgcgggccaa gatctgcaca ctggtatttc ggtttttggg gccgcgggcg     600
gcgacggggc ccgtgcgtcc cagcgcacat gttcggcgag gcggggcctg cgagcgcggc     660
caccgagaat cggacggggg tagtctcaag ctggccggcc tgctctggtg cctggcctcg     720
cgccgccgtg tatcgccccg ccctgggcgg caaggctggc ccggtcggca ccagttgcgt     780
gagcggaaag atggccgctt cccggccctg ctgcagggag ctcaaaatgg aggacgcggc     840
gctcgggaga gcggcgcggt gagtcaccca cacaaaggaa aagggccttt ccgtcctcag     900
ccgtcgcttc atgtgactcc acggagtacc gggcgccgtc caggcacctc gattagttct     960
cgagcttttg gagtacgtcg tctttaggtt ggggggaggg gtttttatgcg atggagtttc    1020 cccacactga gtgggtggag actgaagtta ggccagcttg gcacttgatg taattctcct    1080
tggaatttgc ccttttttgag tttggatctt ggttcattct caagcctcag acagtggttc    1140 aaagttttttt tcttccattt caggtgtcgt ga                                 1172
```

<210> SEQ ID NO 2
<211> LENGTH: 72
<212> TYPE: DNA
<213> ORGANISM: Artificial Sequence
<220> FEATURE:
<223> OTHER INFORMATION: CD8a-1

<400> SEQUENCE: 2

```
atgagctttc catgtaaatt tgtagccagc ttccttctga ttttcaatgt ttcttccaaa      60
ggtgcagtct cc                                                          72
```

<210> SEQ ID NO 3
<211> LENGTH: 75
<212> TYPE: DNA
<213> ORGANISM: Artificial Sequence
<220> FEATURE:
<223> OTHER INFORMATION: CD8a-2

<400> SEQUENCE: 3

```
atgaccatgt atttgtggct taaactcttg gcatttggct ttgcctttct ggacacagaa      60
gtatttgtga caggg                                                       75
```

-continued

```
<210> SEQ ID NO 4
<211> LENGTH: 54
<212> TYPE: DNA
<213> ORGANISM: Artificial Sequence
<220> FEATURE:
<223> OTHER INFORMATION: CD8a-3

<400> SEQUENCE: 4
atgctgtttt tgctacttcc attgttagct gttctcccag gtgatggcaa tgca          54

<210> SEQ ID NO 5
<211> LENGTH: 51
<212> TYPE: DNA
<213> ORGANISM: Artificial Sequence
<220> FEATURE:
<223> OTHER INFORMATION: CD8a-4

<400> SEQUENCE: 5
atgctgtttc tgcagtttct gctgctagct cttcttctcc caggtggtga c             51

<210> SEQ ID NO 6
<211> LENGTH: 72
<212> TYPE: DNA
<213> ORGANISM: Artificial Sequence
<220> FEATURE:
<223> OTHER INFORMATION: CD8a-5

<400> SEQUENCE: 6
atgcccatgg ggtctctgca accgctggcc accttgtacc tgctggggat gctggtcgct    60
tcctgcctcg ga                                                         72

<210> SEQ ID NO 7
<211> LENGTH: 63
<212> TYPE: DNA
<213> ORGANISM: Artificial Sequence
<220> FEATURE:
<223> OTHER INFORMATION: CD8a-6

<400> SEQUENCE: 7
atgcggccgc ggctgtggct cctcttggcc gcgcagctga cagttctcca tggcaactca    60
gtc                                                                   63

<210> SEQ ID NO 8
<211> LENGTH: 51
<212> TYPE: DNA
<213> ORGANISM: Artificial Sequence
<220> FEATURE:
<223> OTHER INFORMATION: CD8a-7

<400> SEQUENCE: 8
atgctgctgc tgccatttca actgttagct gttctctttc ctggtggtaa c             51

<210> SEQ ID NO 9
<211> LENGTH: 75
<212> TYPE: DNA
<213> ORGANISM: Artificial Sequence
<220> FEATURE:
<223> OTHER INFORMATION: CD8a-8

<400> SEQUENCE: 9
atggccgggc ctccgaggct cctgctgctg cccctgcttc tggcgctggc tcgcggcctg    60 cctgggggccc tggct                                                     75
```

```
<210> SEQ ID NO 10
<211> LENGTH: 75
<212> TYPE: DNA
<213> ORGANISM: Artificial Sequence
<220> FEATURE:
<223> OTHER INFORMATION: CD8a-9

<400> SEQUENCE: 10
atgaaccggg gagtcccttt taggcacttg cttctggtgc tgcaactggc gctcctccca      60
gcagccactc aggga                                                       75

<210> SEQ ID NO 11
<211> LENGTH: 62
<212> TYPE: DNA
<213> ORGANISM: Artificial Sequence
<220> FEATURE:
<223> OTHER INFORMATION: CD8a-10

<400> SEQUENCE: 11
atggccttac cagtgaccgc cttgctcctg ccgctggcct tgctgctcca cgccgccagc      60
cg                                                                     62

<210> SEQ ID NO 12
<211> LENGTH: 34
<212> TYPE: DNA
<213> ORGANISM: Artificial Sequence
<220> FEATURE:
<223> OTHER INFORMATION: LoxP  wild type

<400> SEQUENCE: 12
ataacttcgt atagcataca ttatacgaag ttat                                  34

<210> SEQ ID NO 13
<211> LENGTH: 34
<212> TYPE: DNA
<213> ORGANISM: Artificial Sequence
<220> FEATURE:
<223> OTHER INFORMATION: LoxP2722

<400> SEQUENCE: 13
ataacttcgt ataggatacc ttatacgaag ttat                                  34

<210> SEQ ID NO 14
<211> LENGTH: 34
<212> TYPE: DNA
<213> ORGANISM: Artificial Sequence
<220> FEATURE:
<223> OTHER INFORMATION: LoxP511

<400> SEQUENCE: 14
ataacttcgt atagtataca ttatacgaag ttat                                  34

<210> SEQ ID NO 15
<211> LENGTH: 34
<212> TYPE: DNA
<213> ORGANISM: Artificial Sequence
<220> FEATURE:
<223> OTHER INFORMATION: LoxP5271

<400> SEQUENCE: 15
ataacttcgt atagtaaaca ttatacgaag ttat                                  34

<210> SEQ ID NO 16
<211> LENGTH: 34
```

-continued

```
<212> TYPE: DNA
<213> ORGANISM: Artificial Sequence
<220> FEATURE:
<223> OTHER INFORMATION: LoxP3171

<400> SEQUENCE: 16
ataacttcgt atagtatata ttatacgaag ttat                            34

<210> SEQ ID NO 17
<211> LENGTH: 66
<212> TYPE: DNA
<213> ORGANISM: Artificial Sequence
<220> FEATURE:
<223> OTHER INFORMATION: cleavable peptide-1

<400> SEQUENCE: 17
ggaagcggag ctactaactt cagcctgctg aagcaggctg agacgtgga ggagaaccct    60 ggacct                                                          66

<210> SEQ ID NO 18
<211> LENGTH: 63
<212> TYPE: DNA
<213> ORGANISM: Artificial Sequence
<220> FEATURE:
<223> OTHER INFORMATION: cleavable peptide-2

<400> SEQUENCE: 18
ggaagcggag agggcagagg aagtctgcta acatgcggtg acgtcgagga gaatcctgga    60
cct                                                             63

<210> SEQ ID NO 19
<211> LENGTH: 69
<212> TYPE: DNA
<213> ORGANISM: Artificial Sequence
<220> FEATURE:
<223> OTHER INFORMATION: cleavable peptide-3

<400> SEQUENCE: 19
ggaagcggac agtgtactaa ttatgctctc ttgaaattgg ctggagatgt tgagagcaac    60
cctggacct                                                       69

<210> SEQ ID NO 20
<211> LENGTH: 75
<212> TYPE: DNA
<213> ORGANISM: Artificial Sequence
<220> FEATURE:
<223> OTHER INFORMATION: cleavable peptide-4

<400> SEQUENCE: 20
ggaagcggag tgaaacagac tttgaatttt gaccttctca agttggcggg agacgtggag    60
tccaaccctg gacct                                                75

<210> SEQ ID NO 21
<211> LENGTH: 9688
<212> TYPE: DNA
<213> ORGANISM: Artificial Sequence
<220> FEATURE:
<223> OTHER INFORMATION: HIV packaging vector

<400> SEQUENCE: 21
ttggaagggc taattcactc ccaaagaaga caagatatcc ttgatctgtg gatctaccac    60
acacaaggct acttccctga ttagcagaac tacacaccag ggccaggggt cagatatcca    120
```

-continued

```
ctgacctttg gatggtgcta caagctagta ccagttgagc cagataaggt agaagaggcc      180
aataaaggag agaacaccag cttgttacac cctgtgagcc tgcatgggat ggatgacccg      240
gagagagaag tgttagagtg gaggtttgac agccgcctag catttcatca cgtggcccga      300
gagctgcatc cggagtactt caagaactgc tgatatcgag cttgctacaa gggactttcc      360
gctggggact ttccagggag gcgtggcctg ggcgggactg gggagtggcg agccctcaga      420
tcctgcatat aagcagctgc tttttgcctg tactgggtct ctctggttag accagatctg      480
agcctgggag ctctctggct aactagggaa cccactgctt aagcctcaat aaagcttgcc      540
ttgagtgctt caagtagtgt gtgcccgtct gttgtgtgac tctggtaact agagatccct      600
cagacccttt tagtcagtgt ggaaaatctc tagcagtggc gcccgaacag ggacttgaaa      660
gcgaaaggga aaccagagga gctctctcga cgcaggactc ggcttgctga agcgcgcacg      720
gcaagaggcg aggggcggcg actggtgagt acgccaaaaa ttttgactag cggaggctag      780
aaggagagag atgggtgcga gagcgtcagt attaagcggg ggagaattag atcgcgatgg      840
gaaaaaattc ggttaaggcc agggggaaag aaaaaatata aattaaaaca tatagtatgg      900
gcaagcaggg agctagaacg attcgcagtt aatcctggcc tgttagaaac atcagaaggc      960
tgtagacaaa tactgggaca gctacaacca tcccttcaga caggatcaga agaacttaga     1020
tcattatata atacagtagc aaccctctat tgtgtgcatc aaaggataga gataaaagac     1080
accaaggaag ctttagacaa gatagaggaa gagcaaaaca aaagtaagac caccgcacag     1140
caagcggccg ctgatcttca gacctggagg aggagatatg agggacaatt ggagaagtga     1200
attatataaa tataaagtag taaaaattga accattagga gtagcaccca ccaaggcaaa     1260
gagaagagtg gtgcagagag aaaaaagagc agtgggaata ggagctttgt tccttgggtt     1320
cttgggagca gcaggaagca ctatgggcgc agcgtcaatg acgctgacgg tacaggccag     1380
acaattattg tctggtatag tgcagcagca gaacaatttg ctgagggcta ttgaggcgca     1440
acagcatctg ttgcaactca cagtctgggg catcaagcag ctccaggcaa gaatcctggc     1500
tgtggaaaga tacctaaagg atcaacagct cctggggatt tggggttgct ctggaaaact     1560
catttgcacc actgctgtgc cttggaatgc tagttggagt aataaatctc tggaacagat     1620
ttggaatcac acgacctgga tggagtggga cagagaaatt aacaattaca caagcttaat     1680
acactcctta attgaagaat cgcaaaacca gcaagaaaag aatgaacaag aattattgga     1740
attagataaa tgggcaagtt tgtggaattg gtttaacata caaaattggc tgtggtatat     1800
aaaattattc ataatgatag taggaggctt ggtaggttta agaatagttt ttgctgtact     1860
ttctatagtg aatagagtta ggcagggata ttcaccatta tcgtttcaga cccacctccc     1920
aaccccgagg ggacccgaca ggcccgaagg aatagaagaa gaaggtggag agagagacag     1980
agacagatcc attcgattag tgaacggatc tcgacggtat cgatgtcgac gataagcttt     2040
gcaaagatgg ataaagtttt aaacagagag gaatctttgc agctaatgga ccttctaggt     2100
cttgaaagga gtgggaattg gctccggtgc ccgtcagtgg gcagagcgca catcgcccac     2160
agtccccgag aagttggggg gaggggtcgg caattgaacc ggtgcctaga gaaggtggcg     2220
cggggtaaac tgggaaagtg atgtcgtgta ctggctccgc ctttttcccg agggtggggg     2280
agaaccgtat ataagtgcag tagtcgccgt gaacgttctt tttcgcaacg ggtttgccgc     2340
cagaacacag gtaagtgccg tgtgtggttc ccgcgggcct ggcctcttta cgggttatgg     2400
cccttgcgtg ccttgaatta cttccactgg ctgcagtacg tgattcttga tcccgagctt     2460 cggggttggaa gtgggtggga gagttcgagg ccttgcgctt aaggagcccc ttcgcctcgt     2520
```

-continued

```
gcttgagttg aggcctggcc tgggcgctgg ggccgccgcg tgcgaatctg gtggcacctt    2580
cgcgcctgtc tcgctgcttt cgataagtct ctagccattt aaaatttttg atgacctgct    2640
gcgacgcttt ttttctggca agatagtctt gtaaatgcgg gccaagatct gcacactggt    2700
atttcggttt ttggggccgc gggcggcgac ggggcccgtg cgtcccagcg cacatgttcg    2760
gcgaggcggg gcctgcgagc gcggccaccg agaatcggac gggggtagtc tcaagctggc    2820
cggcctgctc tggtgcctgg cctcgcgccg ccgtgtatcg ccccgccctg ggcggcaagg    2880
ctggcccggt cggcaccagt tgcgtgagcg gaaagatggc cgcttcccgg ccctgctgca    2940
gggagctcaa aatggaggac gcggcgctcg ggagagcggg cgggtgagtc acccacacaa    3000
aggaaaaggg cctttccgtc ctcagccgtc gcttcatgtg actccacgga gtaccgggcg    3060
ccgtccaggc acctcgatta gttctcgagc ttttggagta cgtcgtcttt aggttggggg    3120
gaggggtttt atgcgatgga gtttccccac actgagtggg tggagactga agttaggcca    3180
gcttggcact tgatgtaatt ctccttggaa tttgcccttt ttgagtttgg atcttggttc    3240
attctcaagc ctcagacagt ggttcaaagt ttttttcttc catttcaggt gtcgtgagga    3300
atttcgacat ttaaatttaa ttaatctcga cggtatcggt taactttaa aagaaaaggg     3360 gggattgggg ggtacagtgc aggggaaaga atagtagaca taatagcaac agacatacaa    3420
actaaagaat tacaaaaaca aattacaaaa attcaaaatt ttccgatcac gagactagcc    3480
tcgaggttta aactacggga tccactagtc atatgataat caacctctgg attacaaaat    3540
ttgtgaaaga ttgactggta ttcttaacta tgttgctcct tttacgctat gtggatacgc    3600
tgctttaatg cctttgtatc atgctattgc ttcccgtatg gctttcattt tctcctcctt    3660
gtataaatcc tggttgctgt ctctttatga ggagttgtgg cccgttgtca ggcaacgtgg    3720
cgtggtgtgc actgtgtttg ctgacgcaac ccccactggt tggggcattg ccaccacctg    3780
tcagctcctt tccgggactt tcgctttccc cctccctatt gccacggcgg aactcatcgc    3840
cgcctgcctt gcccgctgct ggacaggggc tcggctgttg ggcactgaca attccgtggt    3900
gttgtcgggg aagctgacgt cctttccatg gctgctcgcc tgtgttgcca cctggattct    3960
gcgcgggacg tccttctgct acgtcccttc ggccctcaat ccagcggacc ttccttcccg    4020
cggcctgctg ccggctctgc ggcctcttcc gcgtcttcgc cttcgccctc agacgagtcg    4080
gatctccctt tgggccgcct ccccgcatcg gtacgtatgg ccaggtacct ttaagaccaa    4140
tgacttacaa ggcagctgta gatcttagcc acttttttaaa agaaaagggg ggactggaag    4200
ggctaattca ctcccaacga agacaagatg ggatcaattc accatgggaa taacttcgta    4260
tagcatacat tatacgaagt tatgctgctt tttgcttgta ctgggtctct ctggttagac    4320
cagatctgag cctgggagct ctctggctaa ctagggaacc cactgcttaa gcctcaataa    4380
agcttgcctt gagtgcttca agtagtgtgt gcccgtctgt tgtgtgactc tggtaactag    4440
agatccctca gacccttttta gtcagtgtgg aaaatctcta gcagcatcta gaattaattc    4500
cgtgtattct atagtgtcac ctaaatcgta tgtgtatgat acataaggtt atgtattaat    4560
tgtagccgcg ttctaacgac aatatgtaca agcctaattg tgtagcatct ggcttactga    4620
agcagaccct atcatctctc tcgtaaactg ccgtcagagt cggtttggtt ggacgaacct    4680
tctgagtttc tggtaacgcc gtcccgcacc cggaaatggt cagcgaacca atcagcaggg    4740
tcatcgctag ccagatcctc tacgccggac gcatcgtggc cggcatcacc ggcgccacag    4800
gtgcggttgc tggcgcctat atcgccgaca tcaccgatgg ggaagatcgg gctcgccact    4860
```

-continued

```
tcgggctcat gagcgcttgt ttcggcgtgg gtatggtggc aggccccgtg gccgggggac    4920
tgttgggcgc catctccttg catgcaccat tccttgcggc ggcggtgctc aacggcctca    4980
acctactact gggctgcttc ctaatgcagg agtcgcataa gggagagcgt cgaatggtgc    5040
actctcagta caatctgctc tgatgccgca tagttaagcc agccccgaca cccgccaaca    5100
cccgctgacg cgccctgacg ggcttgtctg ctcccggcat ccgcttacag acaagctgtg    5160
accgtctccg ggagctgcat gtgtcagagg ttttcaccgt catcaccgaa acgcgcgaga    5220
cgaaagggcc tcgtgatacg cctattttta taggttaatg tcatgataat aatggtttct    5280
tagacgtcag gtggcacttt tcggggaaat gtgcgcggaa cccctatttg tttatttttc    5340
taaatacatt caaatatgta tccgctcatg agacaataac cctgataaat gcttcaataa    5400
tattgaaaaa ggaagagtat gagtattcaa catttccgtg tcgcccttat tccctttttt    5460
gcggcatttt gccttcctgt ttttgctcac ccagaaacgc tggtgaaagt aaaagatgct    5520
gaagatcagt tgggtgcacg agtgggttac atcgaactgg atctcaacag cggtaagatc    5580
cttgagagtt ttcgccccga agaacgtttt ccaatgatga gcacttttaa agttctgcta    5640
tgtggcgcgg tattatcccg tattgacgcc gggcaagagc aactcggtcg ccgcatacac    5700
tattctcaga atgacttggt tgagtactca ccagtcacag aaaagcatct tacggatggc    5760
atgacagtaa gagaattatg cagtgctgcc ataaccatga gtgataacac tgcggccaac    5820
ttacttctga caacgatcgg aggaccgaag gagctaaccg cttttttgca caacatgggg    5880
gatcatgtaa ctcgccttga tcgttgggaa ccggagctga atgaagccat accaaacgac    5940
gagcgtgaca ccacgatgcc tgtagcaatg gcaacaacgt tgcgcaaact attaactggc    6000
gaactactta ctctagcttc ccggcaacaa ttaatagact ggatggaggc ggataaagtt    6060
gcaggaccac ttctgcgctc ggcccttccg gctggctggt ttattgctga taaatctgga    6120
gccggtgagc gtgggtctcg cggtatcatt gcagcactgg ggccagatgg taagccctcc    6180
cgtatcgtag ttatctacac gacggggagt caggcaacta tggatgaacg aaatagacag    6240
atcgctgaga taggtgcctc actgattaag cattggtaac tgtcagacca gtttactca    6300 tatatacttt agattgattt aaaacttcat ttttaattta aaaggatcta ggtgaagatc    6360 cttttttgata atctcatgac caaaatccct taacgtgagt tttcgttcca ctgagcgtca    6420
gaccccgtag aaaagatcaa aggatcttct tgagatcctt ttttttctgcg cgtaatctgc    6480 tgcttgcaaa caaaaaaacc accgctacca gcggtggttt gtttgccgga tcaagagcta    6540
ccaactcttt ttccgaaggt aactggcttc agcagagcgc agataccaaa tactgtcctt    6600
ctagtgtagc cgtagttagg ccaccacttc aagaactctg tagcaccgcc tacatacctc    6660
gctctgctaa tcctgttacc agtggctgct gccagtggcg ataagtcgtg tcttaccggg    6720
ttggactcaa gacgatagtt accggataag gcgcagcggt cgggctgaac ggggggttcg    6780
tgcacacagc ccagcttgga gcgaacgacc tacaccgaac tgagatacct acagcgtgag    6840
cattgagaaa gcgccacgct tcccgaaggg agaaaggcgg acaggtatcc ggtaagcggc    6900
agggtcggaa caggagagcg cacgagggag cttccagggg gaaacgcctg gtatctttat    6960
agtcctgtcg ggtttcgcca cctctgactt gagcgtcgat ttttgtgatg ctcgtcaggg    7020
gggcggagcc tatggaaaaa cgccagcaac gcggcctttt tacggttcct ggccttttgc    7080
tggccttttg ctcacatgtt ctttcctgcg ttatcccctg attctgtgga taaccgtatt    7140
accgcctttg agtgagctga taccgctcgc cgcagccgaa cgaccgagcg cagcgagtca    7200
gtgagcgagg aagcggaaga gcgcccaata cgcaaaccgc ctctccccgc gcgttggccg    7260
```

-continued

```
attcattaat gcagctgtgg aatgtgtgtc agttagggtg tggaaagtcc ccaggctccc    7320
cagcaggcag aagtatgcaa agcatgcatc tcaattagtc agcaaccagg tgtggaaagt    7380
ccccaggctc cccagcaggc agaagtatgc aaagcatgca tctcaattag tcagcaacca    7440
tagtcccgcc cctaactccg cccatcccgc ccctaactcc gcccagttcc gcccattctc    7500
cgccccatgg ctgactaatt tttttattt atgcagaggc cgaggccgcc tcggcctctg    7560
agctattcca gaagtagtga ggaggctttt ttggaggcct aggcttttgc aaaaagcttg    7620
gacacaagac aggcttgcga gatatgtttg agaataccac tttatcccgc gtcagggaga    7680
ggcagtgcgt aaaaagacgc ggactcatgt gaaatactgg tttttagtgc gccagatctc    7740
tataatctcg cgcaacctat tttcccctcg aacacttttt aagccgtaga taaacaggct    7800
gggacacttc acatgagcga aaaatacatc gtcacctggg acatgttgca gatccatgca    7860
cgtaaactcg caagccgact gatgccttct gaacaatgga aaggcattat tgccgtaagc    7920
cgtggcggtc tgtaccgggt gcgttactgg cgcgtgaact gggtattcgt catgtcgata    7980
ccgtttgtat ttccagctac gatcacgaca accagcgcga gcttaaagtg ctgaaacgcg    8040
cagaaggcga tggcgaaggc ttcatcgtta ttgatgacct ggtggatacc ggtggtactg    8100
cggttgcgat tcgtgaaatg tatccaaaag cgcactttgt caccatcttc gcaaaaccgg    8160
ctggtcgtcc gctggttgat gactatgttg ttgatatccc gcaagatacc tggattgaac    8220
agccgtggga tatgggcgtc gtattcgtcc cgccaatctc cggtcgctaa tcttttcaac    8280
gcctggcact gccgggcgtt gttctttttta acttcaggcg ggttacaata gtttccagta    8340
agtattctgg aggctgcatc catgacacag gcaaacctga gcgaaaccct gttcaaaccc    8400
cgctttaaac atcctgaaac ctcgacgcta gtccgccgct ttaatcacgg cgcacaaccg    8460
cctgtgcagt cggcccttga tggtaaaacc atccctcact ggtatcgcat gattaaccgt    8520
ctgatgtgga tctggcgcgg cattgaccca cgcgaaatcc tcgacgtcca ggcacgtatt    8580
gtgatgagcg atgccgaacg taccgacgat gatttatacg atacggtgat tggctaccgt    8640
ggcggcaact ggatttatga gtgggc/cccg gatctttgtg aaggaacctt acttctgtgg    8700
tgtgacataa ttggacaaac tacctacaga gatttaaagc tctaaggtaa atataaaatt    8760
tttaagtgta taatgtgtta aactactgat tctaattgtt tgtgtatttt agattccaac    8820
ctatggaact gatgaatggg agcagtggtg gaatgccttt aatgaggaaa acctgttttg    8880
ctcagaagaa atgccatcta gtgatgatga ggctactgct gactctcaac attctactcc    8940
tccaaaaaag aagagaaagg tagaagaccc caaggacttt ccttcagaat tgctaagttt    9000
tttgagtcat gctgtgttta gtaatagaac tcttgcttgc tttgctattt acaccacaaa    9060
ggaaaaagct gcactgctat acaagaaaat tatggaaaaa tattctgtaa cctttataag    9120
taggcataac agttataatc ataacatact gttttttctt actccacaca ggcatagagt    9180
gtctgctatt aataactatg ctcaaaaatt gtgtaccttt agcttttttaa tttgtaaagg    9240 ggttaataag gaatatttga tgtatagtgc cttgactaga gatcataatc agccatacca    9300
catttgtaga ggttttactt gctttaaaaa acctcccaca cctccccctg aacctgaaac    9360
ataaaatgaa tgcaattgtt gttgttaact tgtttattgc agcttataat ggttacaaat    9420
aaagcaatag catcacaaat ttcacaaata aagcattttt ttcactgcat tctagttgtg    9480
gtttgtccaa actcatcaat gtatcttatc atgtctggat caactggata actcaagcta    9540
accaaaatca tcccaaactt cccaccccat accctattac cactgccaat tacctagtgg    9600
```
tttcatttac tctaaacctg tgattcctct gaattatttt cattttaaag aaattgtatt    9660
tgttaaatat gtactacaaa cttagtag                                        9688

<210> SEQ ID NO 22
<211> LENGTH: 181
<212> TYPE: DNA
<213> ORGANISM: Artificial Sequence
<220> FEATURE:
<223> OTHER INFORMATION: 5'LTR sequence or 3'LTR sequence

<400> SEQUENCE: 22
gggtctctct ggttagacca gatctgagcc tgggagctct ctggctaact agggaaccca      60
ctgcttaagc ctcaataaag cttgccttga gtgcttcaag tagtgtgtgc ccgtctgttg     120
tgtgactctg gtaactagag atccctcaga ccctttttagt cagtgtggaa aatctctagc    180
a                                                                      181

<210> SEQ ID NO 23
<211> LENGTH: 588
<212> TYPE: DNA
<213> ORGANISM: Artificial Sequence
<220> FEATURE:
<223> OTHER INFORMATION: WPRE nucleic sequence

<400> SEQUENCE: 23
tcaacctctg gattacaaaa tttgtgaaag attgactggt attcttaact atgttgctcc      60
ttttacgcta tgtggatacg ctgctttaat gcctttgtat catgctattg cttcccgtat     120
ggctttcatt ttctcctcct tgtataaatc ctggttgctg tctctttatg aggagttgtg     180
gcccgttgtc aggcaacgtg gcgtggtgtg cactgtgttt gctgacgcaa cccccactgg     240
ttggggcatt gccaccacct gtcagctcct ttccgggact ttcgctttcc ccctccctat     300
tgccacggcg gaactcatcg ccgcctgcct tgcccgctgc tggacagggg ctcggctgtt     360
gggcactgac aattccgtgg tgttgtcggg gaagctgacg tcctttccat ggctgctcgc     420
ctgtgttgcc acctggattc tgcgcgggac gtccttctgc tacgtccctt cggccctcaa     480
tccagcggac cttccttccc gcggcctgct gccggctctg cggcctcttc cgcgtcttcg     540
ccttcgccct cagacgagtc ggatctccct ttgggccgcc tccccgca                  588

<210> SEQ ID NO 24
<211> LENGTH: 336
<212> TYPE: DNA
<213> ORGANISM: Artificial Sequence
<220> FEATURE:
<223> OTHER INFORMATION: CD19 VL (1907)

<400> SEQUENCE: 24
gacatccagc tgacccagtc tccatcatct ctgagcgcat ctgttggaga tagggtcact      60
atcacttgta aggccagcca aagtgttgat tatgatggtg atagttattt gaactggtac     120
cagcagattc cagggaaagc acctaaattg ttgatctacg atgcttcgaa tctagtttct     180
ggtatccctc ctcgattctc tggcagcgga tctgggacag attacacttt caccatcagc     240
tctcttcaac cagaagacat tgcaacatat cactgtcagc aaagtactga agatccgtgg     300
acgttcggtg gagggaccaa gctacagatc aaacgt                               336

<210> SEQ ID NO 25
<211> LENGTH: 336
<212> TYPE: DNA
<213> ORGANISM: Artificial Sequence

<220> FEATURE:
<223> OTHER INFORMATION: CD19 VL (1902)

<400> SEQUENCE: 25
gacattgtgc tgacgcagtc tccaacctct ttggctgtgt ctctagggca gagggccacc        60
atctcctgca gagccagcga aagtgttgat acttttggca ttagtttat gaactggttc        120 caacagaaac caggacagcc acccaaactc ctcatccatg ctgcatccaa tcaaggatca        180
ggggtccctg ccaggtttag tggtagtggg tctgggacgg acttcagcct caacatccat        240
cctatggagg aggatgatag tgcaatgtat ttctgtcagc aaagtaagga ggttccattc        300
acgttcggct cggggacaaa gttggaaata aaacgg                                  336

<210> SEQ ID NO 26
<211> LENGTH: 333
<212> TYPE: DNA
<213> ORGANISM: Artificial Sequence
<220> FEATURE:
<223> OTHER INFORMATION: CD19 VL (1903)

<400> SEQUENCE: 26
gatatccagc tgacccagtc tccagcttct ttggctgtgt ctctagggca gagggccacc        60
atctcctgca aggccagcca aagtgttgat tatgatggtg atagttattt gaactggtac        120
caacagattc caggacagcc acccaaactc ctcatctatg atgcatccaa tctagtttct        180
gggatcccac ccaggtttag tggcagtggg tctgggacag acttcaccct caacatccat        240
cctgtggaga aggtggatgc tgcaacctat cactgtcagc aaagtactga ggatccgtgg        300
acgttcggtg agggaccaa gctcgagatc aaa                                      333

<210> SEQ ID NO 27
<211> LENGTH: 309
<212> TYPE: DNA
<213> ORGANISM: Artificial Sequence
<220> FEATURE:
<223> OTHER INFORMATION: CD19 VL (1904)

<400> SEQUENCE: 27
gacattcaga tgacccagtc ttctgcctac ctgtctgtat ctctaggagg cagggtcacc        60
attacttgca aggcaagtga ccacattaat aattggttag cctggtatca acataaacca        120
ggaaatgctc ctaggctctt aatatctggt gcaaccactt ggaaactgg ggttccttca        180 agattcagtg gcagtggatc tggaaaggat tacactctca gcattaccag tcttcagact        240
gaagatgttg ctacttatta ctgtcaacag tcttggaata ctccgtggac gttcggtgga        300
ggcaccaag                                                                309

<210> SEQ ID NO 28
<211> LENGTH: 324
<212> TYPE: DNA
<213> ORGANISM: Artificial Sequence
<220> FEATURE:
<223> OTHER INFORMATION: CD19 VL (1905)

<400> SEQUENCE: 28
gacgctgtga tgacccaaac tccactctcc ctgcctgtca gtcttggaga tcaagcctcc        60
atctcttgca ggtctagtca gagccttgaa aacagtaatg gaaacaccta tttgaactgg        120
tacctccaga aaccaggcca gtctccacag ctcctgatct acagggtttc caaccgattt        180
tctggggtcc tagacaggtt cagtggtagt ggatcaggga cagatttcac actgaaaatc        240

-continued

```
agcagagtgg aggctgagga tttgggagtt tatttctgcc tccaagttac acatgtccct    300
cccacgttcg gtgctgggac caag                                           324

<210> SEQ ID NO 29
<211> LENGTH: 336
<212> TYPE: DNA
<213> ORGANISM: Artificial Sequence
<220> FEATURE:
<223> OTHER INFORMATION: CD19 VL (1906)

<400> SEQUENCE: 29
gacatccagc tgacccagtc tccagcttct ttggctgtgt ctctagggca gagggccacc     60
atctcctgca aggccagcca aagtgttgat tatgatggtg atagttattt gaactggtac    120
caacagattc caggacagcc acccaaactc ctcatctatg atgcatccaa tctagtttct    180
ggcatcccac ccaggtttag tggcagtggg tctgggacag acttcaccct caacatccat    240
cctgtggaga aggtggatgc tgcaacctat cactgtcagc aaagtactga agatccgtgg    300
acgttcggtg agggaccaa gctggagatc aaacgt                               336

<210> SEQ ID NO 30
<211> LENGTH: 321
<212> TYPE: DNA
<213> ORGANISM: Artificial Sequence
<220> FEATURE:
<223> OTHER INFORMATION: CD19 VL (1901)

<400> SEQUENCE: 30
gacatccaga tgacacagac tacatcctcc ctgtctgcct ctctgggaga cagagtcacc     60
atcagttgca gggcaagtca ggacattagt aaatatttaa attggtatca gcagaaacca    120
gatggaactg ttaaactcct gatctaccat acatcaagat acactcagg agtcccatca     180 aggttcagtg gcagtgggtc tggaacagat tattctctca ccattagcaa cctggagcaa    240
gaagatattg ccacttactt ttgccaacag ggtaatacgc ttccgtacac gttcggaggg    300
gggaccaagc tggagatcac a                                              321

<210> SEQ ID NO 31
<211> LENGTH: 336
<212> TYPE: DNA
<213> ORGANISM: Artificial Sequence
<220> FEATURE:
<223> OTHER INFORMATION: CD19 VL (1908)

<400> SEQUENCE: 31
gatgttggga tgacccagac tccactcact ttgtcggtca ccattggaca accagcctct     60
ttctcttgca agtcaagtca gagcctctta tatagtaatg gaaaaaccta tttgaattgg    120
ttattacaga ggccaggcca gtctccaaag cgcctaatcc atctggtgtc taaactggac    180
tctggagtcc ctgacaggtt cactggcagt ggatcaggaa cagattttac actgaaaatc    240
ggcagagtgg aggctgagga tttgggagtt tattactgcg tgcaaggtac acattttccg    300
tacacgttcg gaggggggac caaactagaa ataaaa                              336

<210> SEQ ID NO 32
<211> LENGTH: 333
<212> TYPE: DNA
<213> ORGANISM: Artificial Sequence
<220> FEATURE:
<223> OTHER INFORMATION: CD19 VL (1909)

<400> SEQUENCE: 32
```

```
gacattgtgc tgacgcagtc tccaacctct ttggctgtgt ctctagggca gagggccacc      60
atctcctgca gagccagcga aagtgttgat acttttggca ttagtttat gaactggttc      120 caacagaaac caggacagcc acccaaactc ctcatccatg ctgcatccaa tcaaggatcc      180
ggggtccctg ccaggtttag tggtagtggg tctgggacgg acttcagcct caacatccat      240
cctatggagg aggatgatag tgcaatgtat ttctgtcagc aaagtaagga ggttccattc      300
acgttcggct cggggacaaa gttggaaata aaa      333
```

```
<210> SEQ ID NO 33
<211> LENGTH: 321
<212> TYPE: DNA
<213> ORGANISM: Artificial Sequence
<220> FEATURE:
<223> OTHER INFORMATION: CD19 VL (1914)

<400> SEQUENCE: 33
gatatacaga tgacgcagac aacgtcaagt ctttccgcca gcttgggaga ccgagtgact      60
atatcttgta gagcaagcca ggatatttct aagtatctta actggtacca acaaaagccc      120
gatggaacgg ttaagctgct tatataccat accagtagac tccactccgg cgtaccatca      180 cggtttctg gcagtggctc cgggaccgac tattctttga cgatctctaa tctcgaacaa      240
gaggatattg caacatactt ttgtcagcaa ggcaatacct tgccatatac gtttgggggc      300
gggacaaaac ttgagataac c      321
```

```
<210> SEQ ID NO 34
<211> LENGTH: 372
<212> TYPE: DNA
<213> ORGANISM: Artificial Sequence
<220> FEATURE:
<223> OTHER INFORMATION: CD19 VH (1907)

<400> SEQUENCE: 34
caggtccaac tgcagcaatc aggggctgaa gtcaagaaac ctgggtcatc ggtgaaggtc      60
tcctgcaagg cttctggcta cgctttcagt agctactgga tgaactgggt gaggcagagg      120
cctggacagg gtcttgagtg gattggacag atttggcctg agatggtgga tactaactac      180
aatggaaagt tcaaggggcg cgccactatt actgccgacg aatccactaa tacagcctac      240
atggaactca gcagcctacg atctgaggac acagcgttct attcttgtgc aagacgggag      300
actacgacgg taggccgtta ttactatgct atggactact ggggccaagg gaccacggtc      360
accgtctcct ca      372
```

```
<210> SEQ ID NO 35
<211> LENGTH: 363
<212> TYPE: DNA
<213> ORGANISM: Artificial Sequence
<220> FEATURE:
<223> OTHER INFORMATION: CD19 VH (1902)

<400> SEQUENCE: 35
gaggtgcagc tgcaggagtc tggacctgag ctggtgaagc ctggggcctc agtgaagatt      60
tcctgcaaag catctggcta cgcattcagt agctcttgga tgaactgggt gatacagagg      120
cctggacagg gtcttgagtg gattggacgg atttatcctg agatggagga tactaactac      180
aatgggaagt tcaagggcaa ggccacactg actgcagaca atcctccag tacagcctac      240 atgcagctca gcagcctgac ctctgtggac tctgcggtct atttctgtgc aagatcagga      300
```

-continued

```
tttattacta cggtttttaga ctttgactac tggggccacg gcaccactct cacagtctcc        360
tca                                                                        363

<210> SEQ ID NO 36
<211> LENGTH: 372
<212> TYPE: DNA
<213> ORGANISM: Artificial Sequence
<220> FEATURE:
<223> OTHER INFORMATION: CD19 VH (1903)

<400> SEQUENCE: 36
caggtgcagc tgcagcagtc tggggctgag ctggtgaggc ctgggtcctc agtgaagatt         60
tcctgcaagg cttctggcta tgcattcagt agctactgga tgaactgggt gaagcagagg        120
cctggacagg gtcttgagtg gattggacag atttggcctg agatggtgga tactaactac        180
aatggaaagt tcaagggtaa agccactctg actgcagacg aatcctccag cacagcctac        240
atgcaactca gcagcctagc atctgaggac tctgcggtct atttctgtgc aagacgggag        300
actacgacgg taggccgtta ttactatgct atggactact ggggccaagg gaccacggtc        360
accgtctcct cc                                                            372

<210> SEQ ID NO 37
<211> LENGTH: 363
<212> TYPE: DNA
<213> ORGANISM: Artificial Sequence
<220> FEATURE:
<223> OTHER INFORMATION: CD19 VH (1904)

<400> SEQUENCE: 37
caggtccagc tgcagcagtc tggggctgaa ctggtgaggc ctgggtcctc agtgaagatt         60
tcctgtaagg cttctggcta tgcattcagt agctactggg tgaactggat gaagcagagg        120
cctggacagg gacttgagtg gattggacag atttaccctg agatggtgga tactaattac        180
aatggaaagt tcaagggtcg agccacagtg actgcagaca aatcctccag cacatcctac        240
atgcagttca gcagcctaac atctgaggac tctgcggtct atttctgtgc aagatctatt        300
actacggtgg taggctgtgc tatggactac tggggtcaag gaacctcggt caccgtctcc        360
tca                                                                        363

<210> SEQ ID NO 38
<211> LENGTH: 360
<212> TYPE: DNA
<213> ORGANISM: Artificial Sequence
<220> FEATURE:
<223> OTHER INFORMATION: CD19 VH (1905)

<400> SEQUENCE: 38
gaggttcagc tgcaacagtc tggacctgag ctggtaaagc ctggggcttc agtgaagatg         60
tcctgcaagg cttctggata cacattcact agctatgtta tgcactgggt gaagcagaag        120
cctgggcagg gccttgagtg gattggatat gttaatcctt acaatgatgg tactaagtac        180
aatgagaagt tcaaaggcaa ggccacactg acttcagaca aatcctccag cacagcctac        240
atggagctca gcagcctgac ctctgaggac tctgcggtct attactgtgc aagagggcct        300
tattactacg gtagtagccc ctttgactac tggggccaag gccaggtcac cgtctcctca        360

<210> SEQ ID NO 39
<211> LENGTH: 372
<212> TYPE: DNA
<213> ORGANISM: Artificial Sequence
```

-continued

<220> FEATURE:
<223> OTHER INFORMATION: CD19 VH (1906)

<400> SEQUENCE: 39
caggtccaac tgcaggagtc tggggctgag ctggtgaggc ctgggtcctc agtgaagatt      60
tcctgcaagg cttctggtta tgcattcagt agctactgga tgaactgggt gaagcagagg     120
cctggacagg gtcttgagtg gattggacag atttggcctg agatggtga tactaactac      180 aatgaaaagt tcaagggtaa agccactctg actgccgacg aatcctccag cacagcctac     240
atgcaactca gcagcctacg atctgaggac tctgcggtct attcttgtgc aagacgggag     300
actacgacgg taggccgtta ttactatgct atggactact ggggccaagg gaccacggtc     360
accgtctcct ca                                                        372

<210> SEQ ID NO 40
<211> LENGTH: 360
<212> TYPE: DNA
<213> ORGANISM: Artificial Sequence
<220> FEATURE:
<223> OTHER INFORMATION: CD19 VH (1901)

<400> SEQUENCE: 40
gaggtgaaac tgcaggagtc aggacctggc ctggtggcgc cctcacagag cctgtccgtc      60
acatgcactg tctcagggt ctcattaccc gactatggtg taagtggat cgccagcct      120 ccacgaaagg gtctggagtg gctgggagta atatggggta gtgaaaccac atactataat     180
tcagctctca aatccagact gaccatcatc aaggacaact ccaagagcca gttttctta      240 aaaatgaaca gtctgcaaac tgatgacaca gccatttact actgtgccaa acattattac     300
tacggtggta gctatgctat ggactactgg ggtcaaggaa cctcagtcac cgtctcctca     360

<210> SEQ ID NO 41
<211> LENGTH: 366
<212> TYPE: DNA
<213> ORGANISM: Artificial Sequence
<220> FEATURE:
<223> OTHER INFORMATION: CD19 VH (1908)

<400> SEQUENCE: 41
gaggtgcagc tgcaggagtc tggacctgag ctggtaaagc ctggggcttc agtgaagatg      60
tcctgcaagg cttctggata cacattcact agctatgtta tgcactgggt gaagcagaag     120
cctgggcagg gccttgagtg gattggatat tttaatcctt acaatgatgg tactgattac      180
tatgagaagt tcaaaggcaa ggccacactg acttcagaca aatcctccag cacagcctac     240
atggcgctca gcagcctgac ctctgaggac tctgcggtct attactgtgc aagagggacc     300
tattactacg gtagtagcta cccctttgac tactggggcc aaggcaccac tctcacagtc     360
tcctca                                                               366

<210> SEQ ID NO 42
<211> LENGTH: 363
<212> TYPE: DNA
<213> ORGANISM: Artificial Sequence
<220> FEATURE:
<223> OTHER INFORMATION: CD19 VH (1909)

<400> SEQUENCE: 42
gaggtgcagc tgcaggagtc tggacctgag ctggtgaagc ctggggcctc agtgaagatt      60
tcctgcaaag cttctggcta cgcattcagt agctcttgga tgaactgggt gatacagagg     120

-continued

```
cctggacagg gtcttgagtg gattggacgg atttatcctg gagatggaga tactaactac      180
aatgggaagt tcaagggcaa ggccacactg actgcagaca atcctccag  tacagcctac      240 atgcagctca gcagcctgac ctctgtggac tctgcggtct atttctgtgc aagatcagga      300
tttattacta cggttttaga ctttgactac tggggccacg gcaccactct cacagtctcc      360
tca                                                                   363
```

```
<210> SEQ ID NO 43
<211> LENGTH: 360
<212> TYPE: DNA
<213> ORGANISM: Artificial Sequence
<220> FEATURE:
<223> OTHER INFORMATION: CD19 VH (1914)

<400> SEQUENCE: 43
gaggttaagc ttcaggaatc cggaccaggt ttggttgccc ccagccaatc tctcagcgtt       60
acatgcacgg tttcaggcgt cagtctcccc gattacggtg taagttggat tcggcaacct      120
ccgcgaaagg gtctggaatg gctgggggtt atttggggga gtgagacaac ttattacaac      180
tctgcactta agagtcggct taccatcatc aaggataatt caaaatcaca agtattcctg      240
aagatgaact cattgcaaac agatgataca gctatatat  attgtgccaa gcattactat      300
tatggtggtt cttatgcaat ggattactgg gggcaaggca cgtcagtgac agtgagttca      360
```

```
<210> SEQ ID NO 44
<211> LENGTH: 339
<212> TYPE: DNA
<213> ORGANISM: Artificial Sequence
<220> FEATURE:
<223> OTHER INFORMATION: GD 1418VL

<400> SEQUENCE: 44
gacgtggtga tgacccagac cccctgtcc  ctgcccgtga cccccggcga gccgcctcc       60 atctcctgca gatctagtca gagtcttgta caccgtaatg aaacaccta  tttacattgg      120 tacctgcaga agccaggcca gtctccaaag ctcctgattc acaaagtttc caaccgattt      180
tctggggtcc cagacaggtt cagtggcagt ggatcaggga cagatttcac actcaagatc      240
agcagagtgg aggctgagga tctgggagtt tatttctgtt ctcaaagtac acatgttcct      300
ccgctcacgt tcggtgctgg gaccaagctg gagctgaaa                            339
```

```
<210> SEQ ID NO 45
<211> LENGTH: 321
<212> TYPE: DNA
<213> ORGANISM: Artificial Sequence
<220> FEATURE:
<223> OTHER INFORMATION: GD TP5F11mVL

<400> SEQUENCE: 45
gacatcgagc tcactcagtc tccagcaatc atgtctgcat ctccagggga gaaggtcacc       60
atgacctgca gtggcagctc aagtataagt tacatgcact ggtaccagca gaagcctgtc      120
acctccccca aaagatggat ttatgacaca tccaaactgg cttctggagt ccctgctcgc      180
ttcagtggca gtgggtctgg gacctcttat tctctcacaa tcagcagcat ggaggctgta      240
gatgctgcca cttattactg ccatcagcgg agtagttacc cgctcacgtt cggtgctggg      300
acacagttgg aaataaaacg g                                               321
```

```
<210> SEQ ID NO 46
<211> LENGTH: 315
```

```
<212> TYPE: DNA
<213> ORGANISM: Artificial Sequence
<220> FEATURE:
<223> OTHER INFORMATION: GD TPGK8mVL

<400> SEQUENCE: 46
gagctcaccc agtctccatc ctccctgtct gcatctgtag gagacagagt caccatcact        60
tgccgggcaa gtcagagcat tagcaagtat ttaaattggt atcagcagaa accagggaaa       120
gcccctaagc tcctgatcta tgctgcatcc agtttgcaaa gtggggtccc atcaaggttc       180
agtggcagta gatctgggac agatttcact ctcaccatca gcagtctgca acctgaagat       240
tttgcaactt actactgtca acagagttac agtaccccgt ggacgttcgg ccaagagacc       300
aaggtggaaa tcaaa                                                       315

<210> SEQ ID NO 47
<211> LENGTH: 357
<212> TYPE: DNA
<213> ORGANISM: Artificial Sequence
<220> FEATURE:
<223> OTHER INFORMATION: 8H9modified VL

<400> SEQUENCE: 47
caggtcaaac tgcagcagtc tggggctgaa ctggtagaac ctggggcttc agtgaaattg        60
tcctgcaagg cttctggcta caccttcaca aactatgata taaactgggt gaggcagagg       120
cctgaacagg gacttgagtg gattggatgg attttttcctg gagatggtag tactcaatac      180
aatgagaagt tcaagggcaa ggccacactg actacagaca tcctccag cacagcctac         240 atgcagctca gcaggctgac atctgaggac tctgctgtct atttctgtgc aagacagact       300
acggctacct ggtttgctta ctggggccaa gggaccacgg tcaccgtctc ctcagat         357

<210> SEQ ID NO 48
<211> LENGTH: 339
<212> TYPE: DNA
<213> ORGANISM: Artificial Sequence
<220> FEATURE:
<223> OTHER INFORMATION: GD 2beitaVL

<400> SEQUENCE: 48
gaaatagtga tgacgcagtc tccagccacc ctgtctgtgt ctccagggga aagagccacc        60
ctctcctgca gatctagtca gagtcttgta caccgtaatg gaaacaccta tttacattgg       120
tacctgcaga agccaggcca gtctccaaag ctcctgattc acaaagtttc caaccgattt       180
tctggggtcc cagacaggtt cagtggcagt ggatcaggga cagatttcac actcaagatc       240
agcagagtgg aggctgagga tctgggagtt tatttctgtt ctcaaagtac acatgttcct       300
ccgctcacgt tcggtgctgg gaccaagctg gagctgaaa                             339

<210> SEQ ID NO 49
<211> LENGTH: 339
<212> TYPE: DNA
<213> ORGANISM: Artificial Sequence
<220> FEATURE:
<223> OTHER INFORMATION: GD 1418VH

<400> SEQUENCE: 49
gaggtgcagc tggtgcagtc cggcgccgag gtggagaagc ccggcgcctc cgtgaagatc        60
tcctgcaagg cctccggctc ctccttcacc ggctacaaca tgaactgggt gcgccagaac       120
atcggcaagt ccctggagtg gatcggcgcc atcgacccct actacggcgg cacctcctac       180
```
aaccagaagt tcaagggccg cgccaccctg accgtggaca agtccacctc caccgcctac      240
atgcacctga agtccctgcg ctccgaggac accgccgtgt actactgcgt gtccggcatg      300
gagtactggg gccagggcac ctccgtgacc gtgtcctcc      339

<210> SEQ ID NO 50
<211> LENGTH: 351
<212> TYPE: DNA
<213> ORGANISM: Artificial Sequence
<220> FEATURE:
<223> OTHER INFORMATION: GD TP5F11mVH

<400> SEQUENCE: 50
caggtgaaac tgcagcagtc aggacctgaa ctggtgaagc ctggggcttc agtgaagata      60
tcctgcaaga cttctggata caaattcact gaatacacca tgcactgggt gaagcagagc      120
catggaaaga gccttgagtg gattggaggt attaatccta caatggtgg tactaactac      180 aagcagaagt tcaagggcaa ggccacattg actgtagaca agtcctccag cacagcctac      240
atggagctcc gcagcctgac atctgaggat tctgcagtct attactgtgc aagagatact      300
acggtcccgt ttgcttactg ggtccaaggg accacggtca ccgtctcctc a      351

<210> SEQ ID NO 51
<211> LENGTH: 366
<212> TYPE: DNA
<213> ORGANISM: Artificial Sequence
<220> FEATURE:
<223> OTHER INFORMATION: GD TPGK8mVH

<400> SEQUENCE: 51
gaggtgcagc tgctcgagtc gggcccagga ctggtgaagc cttcggggac cctgtccctc      60
acctgcgctg tctctggtgg ctccatcagc agtagtaact ggtggagttg ggtccgccag      120
cccccaggga aggggctgga gtggcttggg aactcgatc atattgggag caccaactac      180
aacccgtccc tcaagagtcg agtcacaatg tcagtagaca agtccaagaa ccagttctcc      240
ctgaagctga gctctgtgag tgccgcggac tcggccgtgt attactgtgc gagacatcac      300
gacccaatac ttggactcga tgcttttgat atctggggcc aagggacaac ggtcaccgtc      360
tcttca      366

<210> SEQ ID NO 52
<211> LENGTH: 330
<212> TYPE: DNA
<213> ORGANISM: Artificial Sequence
<220> FEATURE:
<223> OTHER INFORMATION: 8H9modified VH

<400> SEQUENCE: 52
gacatcgagc tcactcagtc tccaaccacc ctgtctgtga ctccaggaga tcaagtctct      60
ctttcctgca gggccagcca gagtattagc gactacttac actggtacca acaaaaatca      120
catgagtctc cacaacttct catcaaatat gcttcccaat ccatctctgg gatcccctcc      180
aggttcagtg gcagtggatc agggtcagat ttcactctca gtatcaacag tgtggaacct      240
gaagatgttg gagtgtatta ctgtcaaaat ggtcacagct ttccgctcac gttcggtgct      300
gggaccgaac tggagctgga acaggcggcc      330

<210> SEQ ID NO 53
<211> LENGTH: 339
<212> TYPE: DNA
<213> ORGANISM: Artificial Sequence
<220> FEATURE:
<223> OTHER INFORMATION: GD 2beitaVH

<400> SEQUENCE: 53
gaggtccaac tgctgcagtc tggacctgag ctggagaagc ctggcgcttc agtgatgata      60
tcctgcaagg cttctggttc ctcattcact ggctacaaca tgaactgggt gaggcagaac     120
attggaaaga gccttgaatg gattggagct attgatcctt actatggtgg aactagctac     180
aaccagaagt tcaagggcag ggccacattg actgtagaca aatcgtccag cacagcctac     240
atgcacctca gagcctgac atctgaggac tctgcagtct attactgtgt aagcggaatg      300
gagtactggg gtcaaggaac ctcagtcacc gtctcctca                           339

<210> SEQ ID NO 54
<211> LENGTH: 357
<212> TYPE: DNA
<213> ORGANISM: Artificial Sequence
<220> FEATURE:
<223> OTHER INFORMATION: B7H3 VL

<400> SEQUENCE: 54
caggtcaaac tgcagcagtc tggggctgaa ctggtaaagc ctggggcttc agtgaaattg      60
tcctgcaagg cttctggcta caccttcaca aactatgata taaactgggt gaggcagagg     120
cctgaacagg gacttgagtg gattggatgg attttttcctg gagatggtag tactcaatac    180
aatgagaagt tcaagggcaa ggccacactg actacagaca tcctccag cacagcctac       240 atgcagctca gcaggctgac atctgaggac tctgctgtct atttctgtgc aagacagact     300
acggctacct ggtttgctta ctgggggccaa gggaccacgg tcaccgtctc ctcagat       357

<210> SEQ ID NO 55
<211> LENGTH: 330
<212> TYPE: DNA
<213> ORGANISM: Artificial Sequence
<220> FEATURE:
<223> OTHER INFORMATION: B7H3 VH

<400> SEQUENCE: 55
gacatcgagc tcactcagtc tccaaccacc ctgtctgtga ctccaggaga tagagtctct      60
ctttcctgca gggccagcca gagtattagc gactacttac actggtacca acaaaaatca     120
catgagtctc caaggcttct catcaaatat gcttcccaat ccatctctgg gatcccctcc     180
aggttcagtg gcagtggatc agggtcagat ttcactctca gtatcaacag tgtggaacct     240
gaagatgttg gagtgtatta ctgtcaaaat ggtcacagct ttccgctcac gttcggtgct     300
gggaccaagc tggagctgaa acaggcggcc                                     330

<210> SEQ ID NO 56
<211> LENGTH: 321
<212> TYPE: DNA
<213> ORGANISM: Artificial Sequence
<220> FEATURE:
<223> OTHER INFORMATION: CD20 VL (2001)

<400> SEQUENCE: 56
cagatcgtgc tgtcccagag ccccgccata ctttctgcta gtccaggcga aaaggttacc      60
atgacttgta gggcctcaag ctccgtctca tacattcact ggtttcagca aaaacccggg     120
agtagcccta agcatggat ctatgctacc tccaatctcg cctctggcgt gcctgtacgg      180
ttctcggggt caggtagcgg caccagctac agtctgacta tctctcgcgt ggaggctgaa     240

```
gacgcagcga catattactg ccaacagtgg acctccaacc cgcccacatt cggcggcgga      300
acgaaattgg agattaagag a                                                 321

<210> SEQ ID NO 57
<211> LENGTH: 354
<212> TYPE: DNA
<213> ORGANISM: Artificial Sequence
<220> FEATURE:
<223> OTHER INFORMATION: CD20 VL (2002)

<400> SEQUENCE: 57
agaggacaaa ttgttctctc ccagtctcca acaatcctgt ctgcatctcc aggggagaag       60
gtcacaatga cttgcagggc cagctcaagt gtaagttaca tggactggta ccagcagaag      120
ccaggttcct cccccaaacc ctggatttat gccacatcca acctggcttc tggagtccct      180
gctcgcttca gtggcagtgg gtctgggacc tcttactctc tcacaatcag cagagtggag      240
gctgaggatg ctgccactta ttactgccag cagtggatta gtaacccacc cacgttcggt      300
gctgggacca agctggagct gaaacgggct gatgctgcac caactgtatc catc            354

<210> SEQ ID NO 58
<211> LENGTH: 318
<212> TYPE: DNA
<213> ORGANISM: Artificial Sequence
<220> FEATURE:
<223> OTHER INFORMATION: CD20 VL (2003)

<400> SEQUENCE: 58
gacattcagc tgacccagtc tccagcaatc ctgtctgcat ctccagggga gaaggtcaca       60
atgacttgca gggccagctc aagtgtaagt tacatccact ggttccagca gaagccagga      120
tcctccccca aaccctggat ttatgccaca tccaacctgg cttctggagt ccctgttcgc      180
ttcagtggca gtgggtctgg gacttcttac tctctcacaa tcagcagagt ggaggctgaa      240
gatgctgcca cttattactg ccagcagtgg actagtaacc cacccacgtt cggagggggg      300
accaagctgg agatcaaa                                                    318

<210> SEQ ID NO 59
<211> LENGTH: 363
<212> TYPE: DNA
<213> ORGANISM: Artificial Sequence
<220> FEATURE:
<223> OTHER INFORMATION: CD20 VH (2001)

<400> SEQUENCE: 59
caggtgcaac tgcagcaacc cggcgccgag ttggttaagc ccggcgcttc tgtcaagatg       60
tcatgtaaag cctcgggcta cactttaca tcctataata tgcactgggt gaagcagacc      120
cctggacggg gtctggaatg gattggcgct atctacccag aaacggcga tacttcttac      180 aaccagaagt tcaaaggtaa agccacgctc accgcggaca gtcatccag cacagcatat      240 atgcagctta gctcgctgac tagtgaggac agcgcagtgt attactgcgc aagatccaca      300
tactatggcg gtgattggta cttcaatgta tggggggccg ggaccacggt gaccgtcagt      360
gca                                                                    363

<210> SEQ ID NO 60
<211> LENGTH: 369
<212> TYPE: DNA
<213> ORGANISM: Artificial Sequence
<220> FEATURE:
<223> OTHER INFORMATION: CD20 VH (2002)
```

<400> SEQUENCE: 60
caggtgcaac tgcagcagcc tggggctgag ctggtgaagc ctggggcctc agtgaagatg      60
tcctgcaaga cttctggcta cacatttacc agttacaatg tgcactgggt aaagcagaca     120
cctggacagg gcctggaatg gattggagct atttatccag gaaatggcga tacttccttc     180
aatcagaagt tcaaaggcaa ggccacattg actgcagaca atcctccag cacagtctac       240 atgcaactca gcagcctgac atctgaggac tctgcggtct attactgtgc aagatcgaat     300
tactacggta gtagctacgt ttggttcttc gatgtctggg gcgcagggac cacggtcacc     360
gtctcctca                                                            369

<210> SEQ ID NO 61
<211> LENGTH: 363
<212> TYPE: DNA
<213> ORGANISM: Artificial Sequence
<220> FEATURE:
<223> OTHER INFORMATION: CD20 VH (2003)

<400> SEQUENCE: 61
caggtccaac tgcagcagcc tggggctgag ctggtgaagc ctggggcctc agtgaagatg      60
tcctgcaagg cttctggcta cacatttacc agttacaata tgcactgggt aaaacagaca      120
cctggtcggg gcctggaatg gattggagct atttatcccg gaaatggtga tacttcctac      180
aatcagaagt tcaaaggcaa ggccacattg actgcagaca atcctccag cacagcctac       240 atgcagctca gcagcctgac atctgaggac tctgcggtct attactgtgc aagatcgact     300
tactacggcg gtgactggta cttcgatgtc tggggccaag ggaccacggt caccgtctcc      360
tca                                                                  363

<210> SEQ ID NO 62
<211> LENGTH: 357
<212> TYPE: DNA
<213> ORGANISM: Artificial Sequence
<220> FEATURE:
<223> OTHER INFORMATION: CD22 VL (2201)

<400> SEQUENCE: 62
gacatccagc tgactcagtc cccttcctct ctttcagcga gcgtgggcga tcgggttaca      60
atgagttgca agtcgtccca atccgtgcta tactctgcta accacaagaa ttacttggcc      120
tggtatcagc agaaaccggg gaaagccccc aagctcctga tttattgggc aagtactaga     180
gagtcaggcg taccatctcg cttctctggt agtggcagcg gaaccgactt tacgttcaca      240
ataagcagcc tccaacccga agatattgcc acctattatt gtcatcagta cctgagctct     300 tggactttg ggggaggcac gaaagtccaa atcaagagga ccgtggctgc gccttcc         357

<210> SEQ ID NO 63
<211> LENGTH: 321
<212> TYPE: DNA
<213> ORGANISM: Artificial Sequence
<220> FEATURE:
<223> OTHER INFORMATION: CD22 VL (2202)

<400> SEQUENCE: 63
gacatccaga tgacacagag ccccagctcc ctgagcgcca gcgtgggaga cagagtgacc      60
atcacctgtc gggccagcca gaccatctgg tcctacctga actggtatca gcagcggcct     120
ggcaaggccc ccaacctgct gatctatgcc gccagctcac tgcagagcgg cgtgcccagc     180

-continued

```
agattttccg gcagaggcag cggcaccgac ttcaccctga caatcagttc cctgcaggcc        240
gaggacttcg ccacctacta ctgccagcag agctacagca tcccccagac cttcggccag        300
gggaccaagc tggaaatcaa g                                                   321
```

<210> SEQ ID NO 64
<211> LENGTH: 321
<212> TYPE: DNA
<213> ORGANISM: Artificial Sequence
<220> FEATURE:
<223> OTHER INFORMATION: CD22 VL (2203)

<400> SEQUENCE: 64

```
gatatccaga tgacccagac tacatcctcc ctgtctgcct ctctgggaga cagagtcacc         60
attagttgca gggcaagtca ggacattagc aattatttaa actggtatca gcagaaacca        120
gatggaactg ttaaactcct gatctactac acatcaatat tacactcagg agtcccatca        180
aggttcagtg gcagtgggtc tggaacagat tattctctca ccattagcaa cctggagcaa        240
gaagattttg ccacttactt ttgccaacag ggtaatacgc ttccgtggac gttcggtgga        300
ggcaccaagc tggaaatcaa a                                                  321
```

<210> SEQ ID NO 65
<211> LENGTH: 339
<212> TYPE: DNA
<213> ORGANISM: Artificial Sequence
<220> FEATURE:
<223> OTHER INFORMATION: CD22 VL (2204)

<400> SEQUENCE: 65

```
gatgttgtgg tgactcaaac tccactctcc ctgcctgtca gctttggaga tcaagtttct         60
atctcttgca ggtctagtca gagtcttgca aacagttatg ggaacacctt tttgtcttgg        120
tacctgcaca gcctggcca gtctccacag ctcctcatct atgggatttc caacagattt        180
tctggggtgc cagacaggtt cactggcagt ggttcaggga cagatttcac actcaagatc        240
agcacaataa agcctgagga cttgggaatg tattactgct tacaaggtac acatcagccg        300
tacacgttcg gaggggggac caagctggaa ataaaacgt                               339
```

<210> SEQ ID NO 66
<211> LENGTH: 510
<212> TYPE: DNA
<213> ORGANISM: Artificial Sequence
<220> FEATURE:
<223> OTHER INFORMATION: CD22 VH (2201)

<400> SEQUENCE: 66

```
caggtgcagc ttgtccagtc tggcgccgaa gtgaagaaac ctgggagcag tgttaaggtg         60
agctgtaagg cttctgggta cacttttacc tcctattggt tgcactgggt ccggcaggca        120
cccggccaag gctggagtg gattggatat atcaacccgc gcaacgatta caccgagtac        180
aatcagaatt tcaaagacaa ggccactata acggctgatg aatcgactaa cacggcgtat        240
atggagcttt cttccctgag gtccgaagac acagcatttt acttctgcgc ccggagggat        300
atcacaactt tttattgggg ccaaggaaca accgtcacag tgagtagcgc tagtaccaaa        360
ggcccatctg tgttcccttt ggctcccagc agcaaatcta caagcggagg tacggcagcc        420
ttaggctgct tggtcaagga ttacttccct gagccagtta ccgtgtcttg gaactccggt        480
gcgcttacct ctggggtaca cacatttccc                                         510
```

-continued

```
<210> SEQ ID NO 67
<211> LENGTH: 372
<212> TYPE: DNA
<213> ORGANISM: Artificial Sequence
<220> FEATURE:
<223> OTHER INFORMATION: CD22 VH (2202)

<400> SEQUENCE: 67
caggtgcagc tgcagcagtc tggccctggc ctcgtgaagc ctagccagac cctgagcctg      60
acctgtgcca tcagcggcga tagcgtgtcc agcaatagcg ccgcctggaa ctggatcaga     120
cagagcccta gcagaggcct ggaatggctg ggccggacct actaccggtc caagtggtac     180
aacgactacg ccgtgtccgt gaagtcccgg atcaccatca accccgacac cagcaagaac     240
cagttctccc tgcagctgaa cagcgtgacc cccgaggata ccgccgtgta ctactgcgcc     300
agagaagtga ccggcgacct ggaagatgcc ttcgacatct ggggccaggg cacaatggtc     360
accgtgtcta gc                                                         372

<210> SEQ ID NO 68
<211> LENGTH: 369
<212> TYPE: DNA
<213> ORGANISM: Artificial Sequence
<220> FEATURE:
<223> OTHER INFORMATION: CD22 VH (2203)

<400> SEQUENCE: 68
gaagtgcagc tggtggagtc tgggggaggc ttagtgaagc ctggagggtc cctgaaactc      60
tcctgtgcag cctctggatt cgctttcagt atctatgaca tgtcttgggt tcgccagact     120
ccggagaaga ggctggagtg ggtcgcatac attagtagtg gtggtggtac cacctactat     180
ccagacactg tgaagggccg attcaccatc tccagagaca tgccaagaa caccctgtac      240 ctgcaaatga gcagtctgaa gtctgaggac acagccatgt attactgtgc aagacatagt     300
ggctacggta gtagctacgg ggttttgttt gcttactggg gccaagggac tctggtcact     360
gtctctgca                                                             369

<210> SEQ ID NO 69
<211> LENGTH: 363
<212> TYPE: DNA
<213> ORGANISM: Artificial Sequence
<220> FEATURE:
<223> OTHER INFORMATION: CD22 VH (2204)

<400> SEQUENCE: 69
gaggtccaac tgcagcagtc tgggactgta ctggcaaggc ctggggcttc cgtgaagatg      60
tcctgcaagg cttctggcta caggtttacc aactactgga ttcactgggt aaaacagagg     120
cctgggcagg tctagaatg gattggtggt attaatcctg aaataatta tactacgtat       180 aagaggaact tgaagggcaa ggccacactg actgcagtca catccgccag cactgcctac     240
atggacctca gcagcctgac aagtgaggac tctgcggtct attactgtac aagagagggc     300
tatggtaact acggggcctg gtttgcttac tggggccagg ggactctggt caccgtctcc     360
tca                                                                   363

<210> SEQ ID NO 70
<211> LENGTH: 141
<212> TYPE: DNA
<213> ORGANISM: Artificial Sequence
<220> FEATURE:
<223> OTHER INFORMATION: hinge region
```

<400> SEQUENCE: 70
accacgacgc cagcgccgcg accaccaaca ccggcgccca ccatcgcgtc gcagccctg          60 tccctgcgcc cagaggcgtg ccggccagcg gcggggggcg cagtgcacac gagggggctg         120
gacttcgcct gtgatatcta c                                                   141

<210> SEQ ID NO 71
<211> LENGTH: 66
<212> TYPE: DNA
<213> ORGANISM: Artificial Sequence
<220> FEATURE:
<223> OTHER INFORMATION: transmembrane region

<400> SEQUENCE: 71
atctgggcgc ccttggccgg gacttgtggg gtccttctcc tgtcactggt tatcaccctt          60
tactgc                                                                     66

<210> SEQ ID NO 72
<211> LENGTH: 126
<212> TYPE: DNA
<213> ORGANISM: Artificial Sequence
<220> FEATURE:
<223> OTHER INFORMATION: 4-1BB

<400> SEQUENCE: 72
aaacggggca gaaagaaact cctgtatata ttcaaacaac catttatgag accagtacaa          60
actactcaag aggaagatgg ctgtagctgc cgatttccag aagaagaaga aggaggatgt         120
gaactg                                                                    126

<210> SEQ ID NO 73
<211> LENGTH: 336
<212> TYPE: DNA
<213> ORGANISM: Artificial Sequence
<220> FEATURE:
<223> OTHER INFORMATION: CD3zeta

<400> SEQUENCE: 73
agagtgaagt tcagcaggag cgcagacgcc cccgcgtaca gcagggcca gaaccagctc           60 tataacgagc tcaatctagg acgaagagag gagtacgatg tttttggaca agagacgtggc        120 cgggaccctg agatgggggg aaagccgaga aggaagaacc ctcaggaagg cctgtacaat        180
gaactgcaga aagataagat ggcggaggcc tacagtgaga ttgggatgaa aggcgagcgc        240
cggaggggca gggggcacga tggcctttac caggtctca gtacagccac caaggacacc         300
tacgacgccc ttcacatgca ggccctgccc cctcgc                                   336

<210> SEQ ID NO 74
<211> LENGTH: 1029
<212> TYPE: DNA
<213> ORGANISM: Artificial Sequence
<220> FEATURE:
<223> OTHER INFORMATION: CRE

<400> SEQUENCE: 74
atgtccaatt tactgaccgt acaccaaaat ttgcctgcat taccggtcga tgcaacgagt          60
gatgaggttc gcaagaacct gatggacatg ttcagggatc gccaggcgtt ttctgagcat         120
acctggaaaa tgcttctgtc cgtttgccgg tcgtgggcgg catggtgcaa gttgaataac        180
cggaaatggt ttcccgcaga acctgaagat gttcgcgatt atcttctata tcttcaggcg        240
cgcggtctgg cagtaaaaac tatccagcaa catttgggcc agctaaacat gcttcatcgt        300

-continued

```
cggtccgggc tgccacgacc aagtgacagc aatgctgttt cactggttat gcggcgtatc      360
cgaaaagaaa acgttgatgc cggtgaacgt gcaaaacagg ctctagcgtt cgaacgcact      420
gatttcgacc aggttcgttc actcatggaa aatagcgatc gctgccagga tatacgtaat      480
ctggcatttc tggggattgc ttataacacc ctgttacgta tagccgaaat tgccaggatc      540
agggttaaag atatctcacg tactgacggt gggagaatgt taatccatat tggcagaacg      600
aaaacgctgg ttagcaccgc aggtgtagag aaggcactta gcctgggggt aactaaactg      660
gtcgagcgat ggatttccgt ctctggtgta gctgatgatc cgaataacta cctgtttttgc     720 cgggtcagaa aaaatggtgt tgccgcgcca tctgccacca gccagctatc aactcgcgcc      780
ctggaaggga ttttttgaagc aactcatcga ttgatttacg gcgctaagga tgactctggt     840
cagagatacc tggcctggtc tggacacagt gcccgtgtcg gagccgcgcg agatatggcc      900
cgcgctggag tttcaatacc ggagatcatg caagctggtg gctggaccaa tgtaaatatt      960
gtcatgaact atatccgtaa cctggatagt gaaacagggg caatggtgcg cctgctggaa     1020
gatggcgat                                                              1029
```

```
<210> SEQ ID NO 75
<211> LENGTH: 3603
<212> TYPE: DNA
<213> ORGANISM: Artificial Sequence
<220> FEATURE:
<223> OTHER INFORMATION: CD19/CD22 duoCAR New19CRE22-CAR v3

<400> SEQUENCE: 75
```

```
ggatccacac gtgccaccat ggccttacca gtgaccgcct tgctcctgcc gctggccttg       60
ctgtcccacg ccgccaggcc gataacttcg tataggatac cttatacgaa gttatcggag      120
caaaaactta tctctgaaga ggacctcgac atccagatga cacagactac atcctccctg      180
tctgcctctc tgggagacag agtcaccatc agttgcaggg caagtcagga cattagtaaa      240
tatttaaatt ggtatcagca gaaaccagat ggaactgtta aactcctgat ctaccataca      300
tcaagattac actcaggagt cccatcaagg ttcagtggca gtgggtctgg aacagattat      360
tctctcacca ttagcaacct ggagcaagaa gatattgcca cttacttttg ccaacagggt      420
aatacgcttc cgtacacgtt cggagggggg accaagctgg agatcacagg tggcggtggc      480
tcgggcggtg gtgggtcggg tggcggcgga tctgaggtga aactgcagga gtcaggacct      540
ggcctggtgg cgccctcaca gagcctgtcc gtcacatgca ctgtctcagg ggtctcatta      600
cccgactatg gtgtaagctg gattcgccag cctccacgaa agggtctgga gtggctggga      660
gtaatatggg gtagtgaaac acatactat aattcagctc tcaaatccag actgaccatc        720
atcaaggaca actccaagag ccaagttttc ttaaaaatga cagtctgca aactgatgac        780 acagccattt actactgtgc caaacattat tactacggtg gtagctatgc tatggactac      840
tggggccaag aacctcagt caccgtctcc tcagaattca aacttcgta tagtatacat         900 tatacgaagt tatccggaag cggagctact aacttcagcc tgctgaagca ggctggagac      960
gtggaggaga accctggacc tatgtccaat ttactgaccg tacaccaaaa tttgcctgca     1020
ttaccggtcg atgcaacgag tgatgaggtt cgcaagaacc tgatggacat gttcagggat     1080
cgccaggcgt tttctgagca tacctggaaa atgcttctgt ccgtttgccg gtcgtgggcg     1140
gcatggtgca agttgaataa ccggaaatgg tttcccgcag aacctgaaga tgttcgcgat     1200
tatcttctat atcttcaggc gcgcggtctg gcagtaaaaa ctatccagca acatttgggc     1260
```

-continued

```
cagctaaaca tgcttcatcg tcggtccggg ctgccacgac caagtgacag caatgctgtt      1320
tcactggtta tgcggcgtat ccgaaaagaa aacgttgatg ccggtgaacg tgcaaaacag      1380
gctctagcgt tcgaacgcac tgatttcgac caggttcgtt cactcatgga aaatagcgat      1440
cgctgccagg atatacgtaa tctggcattt ctggggattg cttataacac cctgttacgt      1500
atagccgaaa ttgccaggat cagggttaaa gatatctcac gtactgacgg tgggagaatg      1560
ttaatccata ttggcagaac gaaaacgctg gttagcaccg caggtgtaga gaaggcactt      1620
agcctggggg taactaaact ggtcgagcga tggatttccg tctctggtgt agctgatgat      1680
ccgaataact acctgttttg ccgggtcaga aaaaatggtg ttgccgcgcc atctgccacc      1740
agccagctat caactcgcgc cctggaaggg attttttgaag caactcatcg attgatttac      1800
ggcgctaagg atgactctgg tcagagatac ctggcctggt ctggacacag tgcccgtgtc      1860
ggagccgcgc gagatatggc ccgcgctgga gtttcaatac cggagatcat gcaagctggt      1920
ggctggacca atgtaaatat tgtcatgaac tatatccgta acctggatag tgaaacaggg      1980
gcaatggtgc gcctgctgga agatggcgat ggaagcggag agggcagagg aagtctgcta      2040
acatgcggtg acgtcgagga gaatcctgga cctataactt cgtataggat accttatacg      2100
aagttatcgt acccatacga cgtcccagac tacgctacgc gtgatgttgt ggtgactcaa      2160
actccactct ccctgcctgt cagctttgga gatcaagttt ctatctcttg caggtctagt      2220
cagagtcttg caaacagtta tgggaacacc tttttgtctt ggtacctgca caagcctggc      2280
cagtctccac agctcctcat ctatgggatt ccaacagat tttctggggt gccagacagg      2340
ttcactggca gtggttcagg gacagatttc acactcaaga tcagcacaat aaagcctgag      2400
gacttgggaa tgtattactg cttacaaggt acacatcagc cgtacacgtt cggagggggg      2460
accaagctgg aaataaaacg tggcggtggc ggttctggtg gcggtggctc gggcggtggt      2520
ggctcggagg tccaactgca gcagtctggg actgtactgg caaggcctgg ggcttccgtg      2580
aagatgtcct gcaaggcttc tggctacagg tttaccaact actggattca ctgggtaaaa      2640
cagaggcctg ggcagggtct agaatggatt ggtggtatta atcctggaaa taattatact      2700
acgtataaga ggaacttgaa gggcaaggcc acactgactg cagtcacatc cgccagcact      2760
gcctacatgg acctcagcag cctgacaagt gaggactctg cggtctatta ctgtacaaga      2820
gagggctatg gtaactacgg ggcctggttt gcttactggg gccaggggac tctggtcacc      2880
gtctcctcac ccgggataac ttcgtatagt atacattata cgaagttatg caccacgacg      2940
ccagcgccgc gaccaccaac accggcgccc accatcgcgt cgcagcccct gtccctgcgc      3000
ccagaggcgt gccggccagc ggcgggggggc gcagtgcaca cgaggggggct ggacttcgcc      3060 tgtgatatct acatctgggc gcccttggcc gggacttgtg gggtccttct cctgtcactg      3120
gttatcaccc tttactgcaa acggggcaga aagaaactcc tgtatatatt caaacaacca      3180
tttatgagac cagtacaaac tactcaagag gaagatggct gtagctgccg atttccagaa      3240
gaagaagaag gaggatgtga actgagagtg aagttcagca ggagcgcaga cgccccgcg      3300 tacaagcagg gccagaacca gctctataac gagctcaatc taggacgaag agaggagtac      3360
gatgttttgg acaagagacg tggccgggac cctgagatgg ggggaaagcc gagaaggaag      3420
aaccctcagg aaggcctgta caatgaactg cagaaagata agatggcgga ggcctacagt      3480
gagattggga tgaaaggcga gcgccggagg ggcaagggggc acgatggcct ttaccagggt      3540
ctcagtacag ccaccaagga cacctacgac gcccttcaca tgcaggccct gccccctcgc      3600
taa                                                                    3603
```

```
<210> SEQ ID NO 76
<211> LENGTH: 3585
<212> TYPE: DNA
<213> ORGANISM: Artificial Sequence
<220> FEATURE:
<223> OTHER INFORMATION: GD2/B7H3 duoCAR

<400> SEQUENCE: 76
ggatccacac gtgccaccat ggccttacca gtgaccgcct tgctcctgcc gctggccttg       60
ctgctccacg ccgccaggcc gataacttcg tataggatac cttatacgaa gttatcggag      120
caaaaactta tctctgaaga ggacctccag gtcaaactgc agcagtctgg ggctgaactg      180
gtagaacctg gggcttcagt gaaattgtcc tgcaaggctt ctggctacac cttcacaaac      240
tatgatataa actgggtgag gcagaggcct aacagggac ttgagtggat tggatggatt        300
tttcctggag atggtagtac tcaatacaat gagaagttca agggcaaggc cacactgact      360
acagacacat cctccagcac agcctacatg cagctcagca ggctgacatc tgaggactct      420
gctgtctatt tctgtgcaag acagactacg gctacctggt ttgcttactg gggccaaggg      480
accacggtca ccgtctcctc agatggtggc ggtggctcgg gcggtggtgg tcgggtggc       540 ggcggatctg acatcgagct cactcagtct ccaaccaccc tgtctgtgac tccaggagat      600
caagtctctc tttcctgcag ggccagccag agtattagcg actacttaca ctggtaccaa      660
caaaaatcac atgagtctcc acaacttctc atcaaatatg cttcccaatc catctctggg      720
atcccctcca ggttcagtgg cagtggatca gggtcagatt tcactctcag tatcaacagt      780
gtggaacctg aagatgttgg agtgtattac tgtcaaaatg gtcacagctt ccgctcacg       840 ttcggtgctg ggaccgaact ggagctggaa caggcggccg aattcataac ttcgtatagt      900
atacattata cgaagttatc cggaagcgga gctactaact tcagcctgct gaagcaggct      960
ggagacgtgg aggagaaccc tggacctatg tccaatttac tgaccgtaca ccaaaatttg     1020
cctgcattac cggtcgatgc aacgagtgat gaggttcgca agaacctgat ggacatgttc     1080
agggatcgcc aggcgttttc tgagcatacc tggaaaatgc ttctgtccgt ttgccggtcg     1140
tgggcggcat ggtgcaagtt gaataaccgg aaatggtttc ccgcagaacc tgaagatgtt     1200
cgcgattatc ttctatatct tcaggcgcgc ggtctggcag taaaaactat ccagcaacat     1260
ttgggccagc taaacatgct tcatcgtcgg tccgggctgc cacgaccaag tgacagcaat     1320
gctgtttcac tggttatgcg gcgtatccga aagaaaacg ttgatgccgg tgaacgtgca       1380
aaacaggctc tagcgttcga cgcactgat ttcgaccagg ttcgttcact catggaaaat       1440
agcgatcgct gccaggatat acgtaatctg gcatttctgg ggattgctta taacaccctg     1500
ttacgtatag ccgaaattgc caggatcagg gttaaagata tctcacgtac tgacggtggg     1560
agaatgttaa tccatattgg cagaacgaaa acgctggtta gcaccgcagg tgtagagaag     1620
gcacttagcc tggggggtaac taaactggtc gagcgatgga tttccgtctc tggtgtagct     1680
gatgatccga ataactacct gttttgccgg gtcagaaaaa atggtgttgc cgcgccatct     1740
gccaccagcc agctatcaac tcgcgccctg gaagggattt ttgaagcaac tcatcgattg     1800
atttacggcg ctaaggatga ctctggtcag agatacctgg cctggtctgg acacagtgcc     1860
cgtgtcggag ccgcgcgaga tatggcccgc gctggagttt caataccgga gatcatgcaa     1920
gctggtggct ggaccaatgt aaatattgtc atgaactata tccgtaacct ggatagtgaa     1980
acaggggcaa tggtgcgcct gctggaagat ggcgatggaa gcggagaggg cagaggaagt     2040
```

-continued

```
ctgctaacat gcggtgacgt cgaggagaat cctggaccta taacttcgta taggatacct    2100
tatacgaagt tatcgtaccc atacgacgtc ccagactacg ctacgcgtga aatagtgatg    2160
acgcagtctc cagccaccct gtctgtgtct ccaggggaaa gagccaccct ctcctgcaga    2220
tctagtcaga gtcttgtaca ccgtaatgga aacacctatt tacattggta cctgcagaag    2280
ccaggccagt ctccaaagct cctgattcac aaagtttcca accgattttc tggggtccca    2340
gacaggttca gtggcagtgg atcagggaca gatttcacac tcaagatcag cagagtggag    2400
gctgaggatc tgggagttta tttctgttct caaagtacac atgttcctcc gctcacgttc    2460
ggtgctggga ccaagctgga gctgaaaggc ggtggcggtt ctggtggcgg tggctcgggc    2520
ggtggtggct cggaggtcca actgctgcag tctggacctg agctggagaa gcctggcgct    2580
tcagtgatga tatcctgcaa ggcttctggt tcctcattca ctggctacaa catgaactgg    2640
gtgaggcaga acattggaaa gagccttgaa tggattggag ctattgatcc ttactatggt    2700
ggaactagct acaaccagaa gttcaagggc agggccacat tgactgtaga caaatcgtcc    2760
agcacagcct acatgcacct caagagcctg acatctgagg actctgcagt ctattactgt    2820
gtaagcggaa tggagtactg gggtcaagga acctcagtca ccgtctcctc acccgggata    2880
acttcgtata gtatacatta tacgaagtta tgcaccacga cgccagcgcc gcgaccacca    2940
acaccggcgc ccaccatcgc gtcgcagccc ctgtccctgc cccagaggc gtgccggcca    3000 gcggcggggg gcgcagtgca cacgaggggg ctggacttcg cctgtgatat ctacatctgg    3060
gcgcccttgg ccgggacttg tggggtcctt ctcctgtcac tggttatcac cctttactgc    3120
aaacggggca gaaagaaact cctgtatata ttcaaacaac catttatgag accagtacaa    3180
actactcaag aggaagatgg ctgtagctgc cgatttccag aagaagaaga aggaggatgt    3240
gaactgagag tgaagttcag caggagcgca gacgcccccg cgtacaagca gggccagaac    3300
cagctctata cgagctcaa tctaggacga agagaggagt acgatgtttt ggacaagaga    3360
cgtggccggg accctgagat ggggggaaag ccgagaagga agaaccctca ggaaggcctg    3420
tacaatgaac tgcagaaaga taagatggcg gaggcctaca gtgagattgg gatgaaaggc    3480
gagcgccgga ggggcaaggg gcacgatggc ctttaccagg gtctcagtac agccaccaag    3540
gacacctacg acgcccttca catgcaggcc ctgccccctc gctaa                     3585
```

<210> SEQ ID NO 77
<211> LENGTH: 4482
<212> TYPE: DNA
<213> ORGANISM: Artificial Sequence
<220> FEATURE:
<223> OTHER INFORMATION: CD19/CD22/CD20 triCAR

<400> SEQUENCE: 77

```
ggatccacac gtgccaccat ggccttacca gtgaccgcct tgctcctgcc gctggccttg     60
ctgctccacg ccgccaggcc gataacttcg tataggatac cttatacgaa gttatcaata    120
acttcgtata gtaaacatta tacgaagtta tccgagcaaa aacttatctc tgaagaggac    180
ctcgacatcc agatgacaca gactacatcc tccctgtctg cctctctggg agacagagtc    240
accatcagtt gcagggcaag tcaggacatt agtaaatatt taaattggta tcagcagaaa    300
ccagatggaa ctgttaaact cctgatctac catacatcaa gattacactc aggagtccca    360
tcaaggttca gtggcagtgg gtctggaaca gattattctc tcaccattag caacctggag    420
caagaagata ttgccactta cttttgccaa caggtaata cgcttccgta cacgttcgga    480
ggggggacca agctggagat cacaggtggc ggtggctcgg gcggtggtgg gtcgggtggc    540
```

-continued

```
ggcggatctg aggtgaaact gcaggagtca ggacctggcc tggtggcgcc ctcacagagc      600
ctgtccgtca catgcactgt ctcaggggtc tcattacccg actatggtgt aagctggatt      660
cgccagcctc cacgaaaggg tctggagtgg ctgggagtaa tatggggtag tgaaaccaca      720
tactataatt cagctctcaa atccagactg accatcatca aggacaactc caagagccaa      780
gttttcttaa aaatgaacag tctgcaaact gatgacacag ccatttacta ctgtgccaaa      840
cattattact acggtggtag ctatgctatg gactactggg gccaaggaac ctcagtcacc      900
gtctcctcag aattcataac ttcgtatagt atacattata cgaagttatc cggaagcgga      960
gctactaact tcagcctgct gaagcaggct ggagacgtgg aggagaaccc tggacctatg     1020
tccaatttac tgaccgtaca ccaaaatttg cctgcattac cggtcgatgc aacgagtgat     1080
gaggttcgca agaacctgat ggacatgttc agggatcgcc aggcgttttc tgagcatacc     1140
tggaaaatgc ttctgtccgt ttgccggtcg tgggcggcat ggtgcaagtt gaataaccgg     1200
aaatggtttc ccgcagaacc tgaagatgtt cgcgattatc ttctatatct tcaggcgcgc     1260
ggtctggcag taaaaactat ccagcaacat ttgggccagc taaacatgct tcatcgtcgg     1320
tccgggctgc cacgaccaag tgacagcaat gctgtttcac tggttatgcg gcgtatccga     1380
aaagaaaacg ttgatgccgg tgaacgtgca aaacaggctc tagcgttcga acgcactgat     1440
ttcgaccagg ttcgttcact catggaaaat agcgatcgct gccaggatat acgtaatctg     1500
gcatttctgg ggattgctta taacaccctg ttacgtatag ccgaaattgc caggatcagg     1560
gttaaagata tctcacgtac tgacggtggg agaatgttaa tccatattgg cagaacgaaa     1620
acgctggtta gcaccgcagg tgtagagaag gcacttagcc tgggggtaac taaactggtc     1680
gagcgatgga tttccgtctc tggtgtagct gatgatccga ataactacct gttttgccgg     1740
gtcagaaaaa atggtgttgc cgcgccatct gccaccagcc agctatcaac tcgcgccctg     1800
gaagggattt ttgaagcaac tcatcgattg atttacggcg ctaaggatga ctctggtcag     1860
agatacctgg cctggtctgg acacagtgcc cgtgtcggag ccgcgcgaga tatggcccgc     1920
gctggagttt caataccgga gatcatgcaa gctggtggct ggaccaatgt aaatattgtc     1980
atgaactata tccgtaacct ggatagtgaa acaggggcaa tggtgcgcct gctggaagat     2040
ggcgatggaa gcggagaggg cagaggaagt ctgctaacat gcggtgacgt cgaggagaat     2100
cctggaccta taacttcgta tagtaaacat tatacgaagt tatacgcgtc ccagatcgtg     2160
ctgtcccaga gccccgccat actttctgct agtccaggcg aaaaggttac catgacttgt     2220
agggcctcaa gctccgtctc atacattcac tggtttcagc aaaaacccgg gagtagccct     2280
aagccatgga tctatgctac ctccaatctc gcctctggcg tgcctgtacg gttctcgggg     2340
tcaggtagcg gcaccagcta cagtctgact atctctcgcg tggaggctga agacgcagcg     2400
acatattact gccaacagtg gacctccaac ccgcccacat tcggcggcgg aacgaaattg     2460
gagattaaga gaggtggcgg tggctcgggc ggtggtgggt cgggtggcgg cggatctcag     2520
gtgcaactgc agcaacccgg cgccgagttg gttaagcccg gcgcttctgt caagatgtca     2580
tgtaaagcct cgggctacac ttttacatcc tataatatgc actgggtgaa gcagacccct     2640
ggacggggtc tggaatggat tggcgctatc tacccaggaa acggcgatac ttcttacaac     2700
cagaagttca aggtaaagc cacgctcacc gcggacaagt catccagcac agcatatatg     2760
cagcttagct cgctgacaag tgaggacagc gcagtgtatt actgcgcaag atccacatac     2820
tatggcggtg attggtactt caatgtatgg ggggccggga ccacggtgac cgtcagtgca     2880
```

```
agatctataa cttcgtatag tatatattat acgaagttat ccataacttc gtataggata    2940
ccttatacga agttatccta cccatacgac gtcccagact acgctgatgt tgtggtgact    3000
caaactccac tctccctgcc tgtcagcttt ggagatcaag tttctatctc ttgcaggtct    3060
agtcagagtc ttgcaaacag ttatgggaac acctttttgt cttggtacct gcacaagcct    3120
ggccagtctc cacagctcct catctatggg atttccaaca gattttctgg ggtgccagac    3180
aggttcactg gcagtggttc agggacagat ttcacactca agatcagcac aataaagcct    3240
gaggacttgg gaatgtatta ctgcttacaa ggtacacatc agccgtacac gttcggaggg    3300
gggaccaagc tggaaataaa acgtggcggt ggcggttctg gtggcggtgg ctcgggcggt    3360
ggtggctcgg aggtccaact gcagcagtct gggactgtac tggcaaggcc tggggcttcc    3420
gtgaagatgt cctgcaaggc ttctggctac aggtttacca actactggat tcactgggta    3480
aaacagaggc ctgggcaggg tctagaatgg attggtggta ttaatcctgg aaataattat    3540
actacgtata gagaggactt gaagggcaag gccacactga ctgcagtcac atccgccagc    3600
actgcctaca tggacctcag cagcctgaca agtgaggact ctgcggtcta ttactgtaca    3660
agagagggct atggtaacta cggggcctgg tttgcttact ggggccaggg gactctggtc    3720
accgtctcct caaagcttat aacttcgtat agtatacatt atacgaagtt atccataact    3780
tcgtatagta tatattatac gaagttatcc accacgacgc cagcgccgcg accaccaaca    3840
ccggcgccca ccatcgcgtc gcagcccctg tccctgcgcc cagaggcgtg ccggccagcg    3900
gcggggggcg cagtgcacac gagggggctg gacttcgcct gtgatatcta catctgggcg    3960
cccttggccg ggacttgtgg ggtccttctc ctgtcactgg ttatcaccct ttactgcaaa    4020
cggggcagaa agaaactcct gtatatattc aaacaaccat ttatgagacc agtacaaact    4080
actcaagagg aagatggctg tagctgccga tttccagaag aagaagaagg aggatgtgaa    4140
ctgagagtga agttcagcag gagcgcagac gccccgcgt acaagcaggg ccagaaccag    4200
ctctataacg agctcaatct aggacgaaga gaggagtacg atgtttttgga caagagacgt    4260 ggccgggacc ctgagatggg gggaaagccg agaaggaaga accctcagga aggcctgtac    4320
aatgaactgc agaaagataa gatggcggag gcctacagtg agattgggat gaaaggcgag    4380
cgccggaggg gcaagggggca cgatggcctt taccagggtc tcagtacagc caccaaggac    4440
acctacgacg cccttcacat gcaggccctg cccctcgct aa                        4482
```

```
<210> SEQ ID NO 78
<211> LENGTH: 63
<212> TYPE: DNA
<213> ORGANISM: Artificial Sequence
<220> FEATURE:
<223> OTHER INFORMATION: CD8a-11

<400> SEQUENCE: 78
atggcactac ctgtcacggc gttactgctc cccttggcgt tactcctgca tgcggcgaga    60
ccc                                                                  63
```

```
<210> SEQ ID NO 79
<211> LENGTH: 117
<212> TYPE: DNA
<213> ORGANISM: Artificial Sequence
<220> FEATURE:
<223> OTHER INFORMATION: hinge region (2)

<400> SEQUENCE: 79
attgaagtta tgtatcctcc tccttaccta gacaatgaga gagcaatgg aaccattatc    60
```

-continued catgtgaaag ggaaacacct ttgtccaagt cccctatttc ccggaccttc taagccc        117

<210> SEQ ID NO 80
<211> LENGTH: 84
<212> TYPE: DNA
<213> ORGANISM: Artificial Sequence
<220> FEATURE:
<223> OTHER INFORMATION: transmenbrane region (2)

<400> SEQUENCE: 80
ttttgggtgc tggtggtggt tggtggagtc ctggcttgct atagcttgct agtaacagtg        60
gcctttatta ttttctgggt gagg                                               84

<210> SEQ ID NO 81
<211> LENGTH: 126
<212> TYPE: DNA
<213> ORGANISM: Artificial Sequence
<220> FEATURE:
<223> OTHER INFORMATION: 4-1BB (2)

<400> SEQUENCE: 81
aagagaggca ggaagaagct gctgtacatc ttcaagcagc ccttcatgag acccgtgcag        60
accacacagg aggaggacgg ctgcagctgt aggttcccag aggaggagga gggaggatgc       120
gagctg                                                                  126

<210> SEQ ID NO 82
<211> LENGTH: 336
<212> TYPE: DNA
<213> ORGANISM: Artificial Sequence
<220> FEATURE:
<223> OTHER INFORMATION: CD3zeta (2)

<400> SEQUENCE: 82
cgcgtgaagt ttagccggtc cgccgatgca cctgcataca agcagggaca gaaccagctg        60
tataacgagc tgaatctggg ccggagagag gagtatgacg tgctggataa gaggaggggga       120 cgcgaccccg agatgggagg caagcctcgg agaaagaacc cacaggaggg cctgtacaat       180
gagctgcaga aggacaagat ggccgaggcc tattctgaga tcggcatgaa gggagagagg       240 cgccgggggca agggacacga tggcctgtac cagggcctga gcaccgccac aaaggacacc       300
tatgatgccc tgcacatgca ggccctgccc cctcgc                                 336

<210> SEQ ID NO 83
<211> LENGTH: 3018
<212> TYPE: DNA
<213> ORGANISM: Artificial Sequence
<220> FEATURE:
<223> OTHER INFORMATION: CD19/CD22 duoCAR

<400> SEQUENCE: 83
ggatccgcca ccatggcact acctgtcacg gcgttactgc tccccttggc gttactcctg        60
catgcggcga gaccccgacat ccagatgaca cagactacat cctccctgtc tgcctctctg       120
ggagacagag tcaccatcag ttgcagggca agtcaggaca ttagtaaata tttaaattgg       180
tatcagcaga aaccagatgg aactgttaaa ctcctgatct accatacatc aagattacac       240
tcaggagtcc catcaaggtt cagtggcagt gggtctggaa cagattattc tctcaccatt       300
agcaacctgg agcaagaaga tattgccact tacttttgcc aacagggtaa tacgcttccg       360
tacacgttcg gaggggggac caagctggag atcacaggcg gtggcggttc tggtggcggt       420

-continued

```
ggctcgggcg gtggtggctc ggaggtgaaa ctgcaggagt caggacctgg cctggtggcg      480
ccctcacaga gcctgtccgt cacatgcact gtctcagggg tctcattacc cgactatggt      540
gtaagctgga ttcgccagcc tccacgaaag ggtctggagt ggctgggagt aatatggggt      600
agtgaaacca catactataa ttcagctctc aaatccagac tgaccatcat caaggacaac      660
tccaagagcc aagttttctt aaaaatgaac agtctgcaaa ctgatgacac agccatttac      720
tactgtgcca acattatta ctacggtggt agctatgcta tggactactg gggccaagga      780
acctcagtca ccgtctcctc aattgaagtt atgtatcctc ctccttacct agacaatgag      840
aagagcaatg gaaccattat ccatgtgaaa gggaaacacc tttgtccaag tcccctattt      900
cccggacctt ctaagccctt ttgggtgctg gtggtggttg gtggagtcct ggcttgctat      960
agcttgctag taacagtggc ctttattatt ttctgggtga ggaagagagg caggaagaag     1020
ctgctgtaca tcttcaagca gcccttcatg agacccgtgc agaccacaca ggaggaggac     1080
ggctgcagct gtaggttccc agaggaggag gagggaggat gcgagctgcg cgtgaagttt     1140
agccggtccg ccgatgcacc tgcatacaag cagggacaga accagctgta taacgagctg     1200
aatctgggcc ggagagagga gtatgacgtg ctggataaga ggaggggacg cgaccccgag     1260
atgggaggca agcctcggag aaagaaccca caggagggcc tgtacaatga gctgcagaag     1320
gacaagatgg ccgaggccta ttctgagatc ggcatgaagg gagagaggcg ccggggcaag     1380
ggacacgatg gcctgtacca gggcctgagc accgccacaa aggacaccta tgatgccctg     1440
cacatgcagg ccctgccccc tcgcgaattc ggaagcggag ctactaactt cagcctgctg     1500
aagcaggctg agacgtggga ggagaaccct ggacctatgg ccttaccagt gaccgccttg     1560
ctcctgccgc tggccttgct gctccacgcc gccaggccgg atgttgtggt gactcaaact     1620
ccactctccc tgcctgtcag ctttggagat caagtttcta tctcttgcag gtctagtcag     1680
agtcttgcaa acagttatgg gaacaccttt ttgtcttggt acctgcacaa gcctggccag     1740
tctccacagc tcctcatcta tgggatttcc aacagatttt ctggggtgcc agacaggttc     1800
actggcagtg gttcagggac agatttcaca ctcaagatca gcacaataaa gcctgaggac     1860
ttgggaatgt attactgctt acaaggtaca catcagccgt acacgttcgg aggggggacc     1920
aagctggaaa taaaacgtgg tggcggtggc tcgggcggtg gtgggtcggg tggcggcgga     1980
tctgaggtcc aactgcagca gtctgggact gtactggcaa ggcctggggc ttccgtgaag     2040
atgtcctgca aggcttctgg ctacaggttt accaactact ggattcactg ggtaaaacag     2100
aggcctgggc agggtctaga atggattggt ggtattaatc ctggaaataa ttatactacg     2160
tataagagga acttgaaggg caaggccaca ctgactgcag tcacatccgc cagcactgcc     2220
tacatggacc tcagcagcct gacaagtgag gactctgcgg tctattactg tacaagagag     2280
ggctatggta actacggggc ctggtttgct tactggggcc aggggactct ggtcaccgtc     2340
tcctcaacca cgacgccagc gccgcgacca ccaacaccgg cgcccaccat cgcgtcgcag     2400
cccctgtccc tgcgcccaga ggcgtgccgg ccagcggcgg gggcgcagt gcacacgagg     2460 gggctggact cgcctgtga tatctacatc tgggcgccct tggccgggac ttgtggggtc     2520
cttctcctgt cactggttat cacccttta tgcaaacggg gcagaaagaa actcctgtat     2580
atattcaaac aaccatttat gagaccagta caaactactc aagaggaaga tggctgtagc     2640
tgccgatttc cagaagaaga agaaggagga tgtgaactga gagtgaagtt cagcaggagc     2700
gcagacgccc ccgcgtacaa gcagggccag aaccagctct ataacgagct caatctagga     2760
cgaagagagg agtacgatgt tttggacaag agacgtggcc gggaccctga gatggggga     2820
```

-continued

```
aagccgagaa ggaagaaccc tcaggaaggc ctgtacaatg aactgcagaa agataagatg    2880
gcggaggcct acagtgagat tgggatgaaa ggcgagcgcc ggaggggcaa ggggcacgat    2940
ggcctttacc agggtctcag tacagccacc aaggacacct acgacgccct tcacatgcag    3000
gccctgcccc ctcgctaa                                                  3018

<210> SEQ ID NO 84
<211> LENGTH: 3018
<212> TYPE: DNA
<213> ORGANISM: Artificial Sequence
<220> FEATURE:
<223> OTHER INFORMATION: CD22/CD19 duoCAR

<400> SEQUENCE: 84
ggatccgcca ccatggcact acctgtcacg gcgttactgc tccccttggc gttactcctg      60
catgcggcga gacccgatgt tgtggtgact caaactccac tctccctgcc tgtcagcttt     120
ggagatcaag tttctatctc ttgcaggtct agtcagagtc ttgcaaacag ttatgggaac     180 accttttgt cttggtacct gcacaagcct ggccagtctc cacagctcct catctatggg     240
atttccaaca gattttctgg ggtgccagac aggttcactg gcagtggttc aggacagat     300 ttcacactca agatcagcac aataaagcct gaggacttgg gaatgtatta ctgcttacaa     360
ggtacacatc agccgtacac gttcggaggg gggaccaagc tggaaataaa acgtggcggt     420
ggcggttctg gtggcggtgg ctcgggcggt ggtggctcgg aggtccaact gcagcagtct     480
gggactgtac tggcaaggcc tgggggcttcc gtgaagatgt cctgcaaggc ttctggctac     540
aggtttacca actactggat tcactgggta aaacagaggc ctgggcaggg tctagaatgg     600
attggtggta ttaatcctgg aaataattat actacgtata gaggaactt gaagggcaag     660 gccacactga ctgcagtcac atccgccagc actgcctaca tggacctcag cagcctgaca     720
agtgaggact ctgcggtcta ttactgtaca agagagggct atggtaacta cggggcctgg     780
tttgcttact ggggccaggg gactctggtc accgtctcct caattgaagt tatgtatcct     840
cctccttacc tagacaatga aagagcaat ggaaccatta tccatgtgaa agggaaacac     900
ctttgtccaa gtcccctatt tcccggacct tctaagccc tttgggtgct ggtggtggtt     960
ggtggagtcc tggcttgcta tagcttgcta gtaacagtgg cctttattat tttctgggtg    1020
aggaagagag gcaggaagaa gctgctgtac atcttcaagc agcccttcat gagacccgtg    1080
cagaccacac aggaggagga cggctgcagc tgtaggttcc cagaggagga ggaggagga    1140 tgcgagctgc gcgtgaagtt tagccggtcc gccgatgcac ctgcatacaa gcaggacag    1200 aaccagctgt ataacgagct gaatctgggc cggagagagg agtatgacgt gctggataag    1260 aggagggac gcgacccga gatgggaggc aagcctcgga gaaagaaccc acaggagggc    1320
ctgtacaatg agctgcagaa ggacaagatg gccgaggcct attctgagat cggcatgaag    1380
ggagagaggc gccggggcaa gggacacgat ggcctgtacc agggcctgag caccgccaca    1440
aaggacacct atgatgccct gcacatgcag gccctgcccc ctcgcgaatt cggaagcgga    1500
gctactaact tcagcctgct gaagcaggct ggagacgtgg aggagaaccc tggacctatg    1560
gccttaccag tgaccgcctt gctcctgccg ctggccttgc tgctccacgc cgccaggccg    1620
gacatccaga tgacacagac tacatcctcc ctgtctgcct ctctgggaga cagagtcacc    1680
atcagttgca gggcaagtca ggacattagt aaatatttaa attggtatca gcagaaacca    1740
gatggaactg ttaaactcct gatctaccat acatcaagat tacactcagg agtcccatca    1800
```

-continued

```
aggttcagtg gcagtgggtc tggaacagat tattctctca ccattagcaa cctggagcaa   1860
gaagatattg ccacttactt ttgccaacag ggtaatacgc ttccgtacac gttcggaggg   1920
gggaccaagc tggagatcac aggtggcggt ggctcgggcg gtggtgggtc gggtggcggc   1980
ggatctgagg tgaaactgca ggagtcagga cctggcctgg tggcgccctc acagagcctg   2040
tccgtcacat gcactgtctc aggggtctca ttacccgact atggtgtaag ctggattcgc   2100
cagcctccac gaaagggtct ggagtggctg ggagtaatat ggggtagtga aaccacatac   2160
tataattcag ctctcaaatc cagactgacc atcatcaagg acaactccaa gagccaagtt   2220
ttcttaaaaa tgaacagtct gcaaactgat gacacagcca tttactactg tgccaaacat   2280
tattactacg gtggtagcta tgctatggac tactggggcc aaggaacctc agtcaccgtc   2340
tcctcaacca cgacgccagc gccgcgacca ccaacaccgg cgcccaccat cgcgtcgcag   2400
cccctgtccc tgcgcccaga ggcgtgccgg ccagcggcgg ggggcgcagt gcacacgagg   2460
gggctggact tcgcctgtga tatctacatc tgggcgccct tggccgggac ttgtgggtc     2520 cttctcctgt cactggttat caccctttac tgcaaacggg gcagaaagaa actcctgtat   2580
atattcaaac aaccatttat gagaccagta caaactactc aagaggaaga tggctgtagc   2640
tgccgatttc cagaagaaga agaaggagga tgtgaactga gagtgaagtt cagcaggagc   2700
gcagacgccc ccgcgtacaa gcagggccag aaccagctct ataacgagct caatctagga   2760
cgaagagagg agtacgatgt tttggacaag agacgtggcc gggaccctga gatgggggga   2820
aagccgagaa ggaagaaccc tcaggaaggc ctgtacaatg aactgcagaa agataagatg   2880
gcggaggcct acagtgagat tgggatgaaa ggcgagcgcc ggaggggcaa ggggcacgat   2940
ggcctttacc agggtctcag tacagccacc aaggacacct acgacgccct tcacatgcag   3000
gccctgcccc ctcgctaa                                                 3018
```

VECTOR GENETICALLY ENGINEERED WITH CHIMERIC ANTIGEN RECEPTOR AND AGAINST TWO OR MORE TARGETS AND APPLICATION THEREOF

CROSS REFERENCE TO RELATED APPLICATIONS

This application is a National Stage entry under 35 U.S.C. § 371 of PCT/CN2021/128240, filed on Nov. 2, 2021, and claims priority to PCT/CN2020/125956, filed on Nov. 2, 2020, the entire contents of which are incorporated herein by reference.

FIELD OF THE INVENTION

The present application belongs to the field of cell therapies, and in particular, relates to a chimeric antigen receptor-genetically engineered vector for combined treatment of diseases such as human tumors by means of two or more targets, a related immune cell and applications thereof.

BACKGROUND OF THE INVENTION

Chimeric antigen receptor-engineered T cell therapy (CART) is an effective adoptive cellular immunotherapy developed in recent years, in which autologously-derived T cells are genetically engineered to allow effector T lymphocytes to produce targeting cytotoxicity against tumor cells, thereby achieving the purpose of removing tumor cells in vivo.

The CART has achieved a significant clinical efficacy for relapsed or refractory acute lymphoblastic leukemia and lymphoma and has been recognized by the industry. The targeting ability of the CART depends on the method by which T cells are modified by means of the genetic engineering technology to express specific single-chain antibodies (scFvs) capable of recognizing their own tumor associated antigens (TAAs). The specific scFvs consist of light chain variable regions (VL) and heavy chain variable regions (VH) of TAA-specific monoclonal antibodies, with soft hinge regions between the VLs and the VHs. In addition to the expression of specific single-chain antibodies against tumor cells on the surfaces of T cells, co-stimulatory molecules that can synergistically activate T cells, such as CD28, 4-1BB and OX4, are expressed simultaneously in the T cells, thereby relying on the specific single-chain antibodies to recognize the tumor cells on the one hand, and on the other hand, synergistically activating the T cells by means of the above co-stimulatory molecules and CD3ζ to produce the targeting cytotoxicity.

Studies in China and abroad have found that the CART combination or sequential cellular therapy with CD19 and CD22 is helpful to reduce the level of a possible cytokine storm to further improve the long-term efficacy on a disease, and is also helpful to provide a re-treatment opportunity for patients who have failed in single treatment. To further improve the efficacy of the CART therapy, it is helpful to treat tumors by constructing CART cells by means of the combination of two or more different targets.

SUMMARY OF THE INVENTION

The present application provides a chimeric antigen receptor-genetically engineered vector for combined treatment of diseases such as human tumors by means of two or more targets, a related immune cell and applications thereof.

The chimeric antigen receptor-genetically engineered vector for combined treatment of diseases such as human tumors by means of two or more targets, a related immune cell and applications thereof described in the present application may have at least one beneficial effect selected from the group consisting of: 1) the killing ability against target cells can be enhanced; 2) the risk of disease recurrence caused by possible antigen escape is reduced; 3) each independent chimeric antigen receptor protein can be endowed with the expression level close to 1:1; 4) the recombination efficiency between a viral vector and a human genome can be improved to a large extent to obtain an immune cell with a high transfection efficiency; and 5) the clinical efficacy can be improved significantly.

In one aspect, the present application provides a nucleic acid molecule expressing at least two types of chimeric antigen receptors (CARs), comprising a nucleic acid sequence encoding a first antigen-binding domain and a nucleic acid sequence encoding a second antigen-binding domain, as well as nucleic acid sequences and/or cleavable peptide sequences of at least one pair of LoxP sites, with each pair of the LoxP sites recognizable by a corresponding LoxP site recognition enzyme, wherein the first antigen-binding domain and the second antigen-binding domain different from the first antigen-binding domain are involved in the composition of a first chimeric antigen receptor and a second chimeric antigen receptor, respectively, and wherein at least one pair of the LoxP sites comprises therebetween at least one nucleic acid sequence encoding the antigen-binding domain.

In some embodiments, in the nucleic acid molecule, the LoxP sites are selected from the group consisting of: wild-type LoxP, LoxP2722, LoxP511, LoxP5271, and LoxP3171.

In some embodiments, in the nucleic acid molecule, the antigen-binding domains specifically bind to tumor antigens.

In some embodiments, in the nucleic acid molecule, the tumor antigens are selected from the group consisting of: A33, B7H3, BCMA, CA125, CD1, CD10, CD102, CD11a, CD11b, CD123, CD13, CD133, CD134, CD137, CD138, CD14, CD15, CD19, CD2, CD20, CD200, CD21, CD22, CD23, CD25, CD27, CD28, CD3, CD30, CD33, CD34, CD36, CD37, CD38, CD4, CD40, CD41, CD42, CD43, CD44, CD45, CD5, CD56, CD58, CD65, CD66c, CD7, CD70, CD73, CD74, CD8, CD80, CD81, CD86, CD9, CD94, CD97, CD99, CEA, CEACAM6, CLL1, CS1, DLL1, DLL3, EGFR, EGFR VIII, ERBB2, FGF19, GD2, GD3, HER3, IL3Ra, NCAM, NG2, NKG2A, NTBA, PD-1, PDL-1, PSGL1, PSMA, ROR1, and VEGF.

In some embodiments, the nucleic acid molecule comprises a nucleic acid sequence encoding a promoter.

In some embodiments, in the nucleic acid molecule, the promoter is selected from the group consisting of: EF1α, CMV, MSCV, and UbC.

In some embodiments, the nucleic acid molecule comprises at least one nucleic acid sequence encoding a leader peptide.

In some embodiments, in the nucleic acid molecule, a 5'-terminal of the nucleic acid sequence encoding the leader peptide is linked to a 3'-terminal of the nucleic acid sequence encoding the promoter, or a 3'-terminal of the nucleic acid sequence encoding the leader peptide is linked to a of the nucleic acid sequence encoding the antigen-binding domain.

In some embodiments, in the nucleic acid molecule, the leader peptide comprises a leader peptide moiety derived from a protein selected from the group consisting of: CD8, CD33, and CD45.

In some embodiments, the nucleic acid molecule comprises a nucleic acid sequence encoding a non-antigen-binding function domain of a chimeric antigen receptor, wherein the non-antigen binding function domain comprises a hinge region, a transmembrane region, a co-stimulatory domain, and/or an intracellular signaling domain.

In some embodiments, in the nucleic acid molecule, the nucleic acid sequence encoding the non-antigen-binding function domain is located downstream of the nucleic acid sequence encoding the antigen-binding domain, or, between the nucleic acid sequence encoding the first antigen-binding domain and the nucleic acid sequence encoding the second antigen-binding domain.

In some embodiments, in the nucleic acid molecule, the hinge region comprises a hinge region derived from a protein selected from the group consisting of: CD8, CD28, and 4-1BB.

In some embodiments, in the nucleic acid molecule, the transmembrane region comprises a transmembrane region derived from a protein selected from the group consisting of: CD8, CD28 and CD19.

In some embodiments, in the nucleic acid molecule, the co-stimulatory domain comprises a co-stimulatory domain derived from a protein selected from the group consisting of: 4-1BB, OX40, CD2, CD27, CD28, CDS, ICAM-1, LFA-1, and ICOS.

In some embodiments, in the nucleic acid molecule, the intracellular signaling domain comprises an intracellular signaling domain derived from a protein selected from the group consisting of: CD3ζζ, FcεRIγ, and ZAP70.

In some embodiments, in the nucleic acid molecule, the nucleic acid molecule comprises a nucleic acid sequence encoding WPRE, wherein the nucleic acid sequence encoding WPRE is located downstream of the nucleic acid sequence encoding the non-antigen-binding function domain.

In some embodiments, in the nucleic acid molecule, the nucleic acid molecule comprises a nucleic acid sequence encoding a backbone vector, wherein the nucleic acid sequence encoding the backbone vector is located upstream of the nucleic acid sequence encoding the promoter.

In some embodiments, in the nucleic acid molecule, the backbone vector comprises a viral vector.

In some embodiments, in the nucleic acid molecule, the backbone vector comprises an HIV packaging vector.

In some embodiments, in the nucleic acid molecule, the nucleic acid molecule comprises a 5' LTR sequence located at a 5'-terminal of the nucleic acid molecule.

In some embodiments, the nucleic acid molecule comprises a 3' LTR sequence located at a 3'-terminal of the nucleic acid molecule.

In some embodiments, the nucleic acid molecule comprises a nucleic acid sequence encoding a recognition enzyme specifically recognizing the LoxP sites, wherein the recognition enzyme is selected from the group consisting of: CRE and Brec1.

In some embodiments, in the nucleic acid molecule, the nucleic acid sequence encoding the recognition enzyme is located between the nucleic acid sequence encoding the first antigen-binding domain and the nucleic acid sequence encoding the second antigen-binding domain.

In some embodiments, in the nucleic acid molecule, the nucleic acid sequence encoding the recognition enzyme is located upstream of the nucleic acid sequence encoding the first antigen-binding domain, and downstream of the nucleic acid sequence encoding the promoter.

In some embodiments, in the nucleic acid molecule, the nucleic acid sequence encoding the recognition enzyme is located downstream of the nucleic acid sequence encoding the non-antigen-binding function domain.

In some embodiments, in the nucleic acid molecule, the cleavable peptide is selected from the group consisting of: P2A, T2A, F2A, E2A, BmCPV2A, and BmIFV2A.

In some embodiments, in the nucleic acid molecule, the nucleic acid sequence encoding the cleavable peptide is located at a 3'-terminal and/or 5'-terminal of the nucleic acid sequence encoding the recognition enzyme.

In some embodiments, in the nucleic acid molecule, the nucleic acid sequence encoding the cleavable peptide is located at a 3'-terminal of the nucleic acid sequence encoding the non-antigen-binding function domain.

In some embodiments, in the nucleic acid molecule, the nucleic acid sequence encoding the cleavable peptide is located at a 3'-terminal of the nucleic acid sequence encoding the leader peptide.

In some embodiments, the nucleic acid molecule expresses two types of chimeric antigen receptors.

In some embodiments, the nucleic acid molecule comprises two different pairs of LoxP sites.

In some embodiments, in the nucleic acid molecule, a first pair of the LoxP sites comprises therebetween the nucleic acid sequence encoding the first antigen-binding domain.

In some embodiments, in the nucleic acid molecule, a second pair of the LoxP sites comprises therebetween the nucleic acid sequence encoding the second antigen-binding domain.

In some embodiments, in the nucleic acid molecule, the nucleic acid molecule comprises at least one pair of LoxP sites with reverse-complementing sequences.

In some embodiments, in the nucleic acid molecule, the one pair of LoxP sites with reverse-complementing sequences comprises therebetween the nucleic acid sequence encoding the first antigen-binding domain and a reverse-complementing sequence of the nucleic acid sequence encoding the second antigen-binding domain; or, the one pair of LoxP sites with reverse-complementing sequences comprises therebetween a reverse-complementing sequence of the nucleic acid sequence encoding the first antigen-binding domain, and the nucleic acid sequence encoding the second antigen-binding domain.

In some embodiments, the nucleic acid molecule expresses three types of chimeric antigen receptors.

In some embodiments, the nucleic acid molecule comprises four different pairs of LoxP sites.

In some embodiments, in the nucleic acid molecule, a first pair of the LoxP sites comprises therebetween the nucleic acid sequence encoding the first antigen-binding domain and the nucleic acid sequence encoding the second antigen-binding domain.

In some embodiments, in the nucleic acid molecule, a second pair of the LoxP sites comprises therebetween the nucleic acid sequence encoding the first antigen-binding domain.

In some embodiments, in the nucleic acid molecule, a third pair of the LoxP sites comprises therebetween the nucleic acid sequence encoding the second antigen-binding domain and a nucleic acid sequence encoding a third antigen-binding domain.

In some embodiments, in the nucleic acid molecule, a fourth pair of the LoxP sites comprises therebetween the nucleic acid sequence encoding the third antigen-binding domain.

In some embodiments, the nucleic acid molecule comprises a nucleotide sequence as set forth in SEQ ID NO: 77.

In another aspect, the present application provides a plasmid comprising the nucleic acid molecule as defined.

In some embodiments, the plasmid comprises a viral plasmid.

In another aspect, the present application provides a cell, comprising the nucleic acid molecule as defined or the plasmid as defined.

In some embodiments, the cell comprises a cell selected from the group consisting of: a T cell and a NK cell.

In some embodiments, the cell expresses at least two different types of chimeric antigen receptors.

In some embodiments, an application of the nucleic acid molecule as defined, the plasmid as defined, and/or the cell as defined in preparation of chimeric antigen receptors.

In another aspect, the present application provides a method for preparing a chimeric antigen receptor, comprising the following steps:

(1) providing a nucleic acid molecule comprising a nucleic acid sequence encoding a first antigen-binding domain and a nucleic acid sequence encoding a second antigen-binding domain, as well as at least one pair of LoxP sites and/or cleavable peptide sequences, with each pair of the LoxP sites recognizable by a corresponding LoxP site recognition enzyme, wherein the first antigen-binding domain and the second antigen-binding domain different from the first antigen-binding domain are involved in the composition of a first chimeric antigen receptor and a second chimeric antigen receptor, respectively, and wherein at least one pair of the LoxP sites comprises therebetween at least one nucleic acid sequence encoding the antigen-binding domain;

(2) contacting the nucleic acid molecule with the corresponding LoxP site recognition enzyme; and (3) removing the sequence between each pair of the LoxP sites respectively to form an expression molecule comprising only one nucleic acid molecule encoding the antigen-binding domain, wherein the expression molecule can express a chimeric antigen receptor.

In some embodiments, in the method, the contacting comprises adding the corresponding LoxP site recognition enzyme.

In some embodiments, in the method, the contacting comprises expressing the nucleic acid molecule encoding the corresponding LoxP site recognition enzyme.

In some embodiments, in the method, the nucleic acid molecule encoding the recognition enzyme is located on a vector.

In some embodiments, in the method, the nucleic acid molecule encoding the recognition enzyme is located on a different vector than the nucleic acid molecule in step (1).

In some embodiments, in the method, the nucleic acid molecule in step (1) comprises the nucleic acid molecule encoding the recognition enzyme.

In some embodiments, in the method, the LoxP sites are selected from the group consisting of: wild-type LoxP, LoxP2722, LoxP511, LoxP5271, and LoxP3171.

In some embodiments, in the method, the antigen-binding domains specifically bind to tumor antigens.

In some embodiments, in the method, the tumor antigens are selected from the group consisting of: CD19, CD22, CD20, GD2, and B7H3.

In some embodiments, the method comprises a nucleic acid sequence encoding a promoter.

In some embodiments, in the method, the promoter is selected from the group consisting of: EF1α, CMV, MSCV, and UbC.

In some embodiments, the method comprises at least one nucleic acid sequence encoding a leader peptide.

In some embodiments, in the method, a 5'-terminal of the nucleic acid sequence encoding the leader peptide is linked to a 3'-terminal of the nucleic acid sequence encoding the promoter, or a 3'-terminal of the nucleic acid sequence encoding the leader peptide is linked to a 5'-terminal of the nucleic acid sequence encoding the antigen-binding domain.

In some embodiments, in the method, the leader peptide comprises a leader peptide moiety derived from a protein selected from the group consisting of CD8, CD33, and CD45.

In some embodiments, in the method, the method comprises a nucleic acid sequence encoding a non-antigen-binding function domain of a chimeric antigen receptor, wherein the non-antigen binding function domain comprises a hinge region, a transmembrane region, a co-stimulatory domain, and/or an intracellular signaling domain.

In some embodiments, in the method, the nucleic acid sequence encoding the non-antigen-binding function domain is located downstream of the nucleic acid sequence encoding the antigen-binding domain, or, between the nucleic acid sequence encoding the first antigen-binding domain and the nucleic acid sequence encoding the second antigen-binding domain.

In some embodiments, in the method, the hinge region comprises a hinge region derived from a protein selected from the group consisting of: CD8, CD28, and 4-1BB In some embodiments, in the method, the transmembrane region comprises a transmembrane region derived from a protein selected from the group consisting of: CD8, CD28 and CD19.

In some embodiments, in the method, the co-stimulatory domain comprises a co-stimulatory domain derived from a protein selected from the group consisting of: 4-1BB, OX40, CD2, CD27, CD28, CDS, ICAM-1, LFA-1, and ICOS.

In some embodiments, in the method, the intracellular signaling domain comprises an intracellular signaling domain derived from a protein selected from the group consisting of: CD3ζ, FccRIγ, and ZAP70.

In some embodiments, the method comprises a nucleic acid sequence encoding WPRE, wherein the nucleic acid sequence encoding WPRE is located downstream of the nucleic acid sequence encoding the non-antigen-binding function domain.

In some embodiments, the method comprises a nucleic acid sequence encoding a backbone vector, wherein the nucleic acid sequence encoding the backbone vector is located upstream of the nucleic acid sequence encoding the promoter.

In some embodiments, in the method, the backbone vector comprises a viral vector.

In some embodiments, in the method, the backbone vector comprises an HIV packaging vector.

In some embodiments, the method comprises a 5' LTR sequence located at a 5'-terminal of the nucleic acid molecule.

In some embodiments, in the method comprises a 3' LTR sequence located at a 3'-terminal of the nucleic acid molecule.

In some embodiments, the method comprises a nucleic acid sequence encoding a recognition enzyme specifically recognizing the LoxP sites, wherein the recognition enzyme is selected from the group consisting of: CRE and Brec1.

In some embodiments, in the method, the nucleic acid sequence encoding the recognition enzyme is located between the nucleic acid sequence encoding the first anti-gen-binding domain and the nucleic acid sequence encoding the second antigen-binding domain.

In some embodiments, in the method, the nucleic acid sequence encoding the recognition enzyme is located upstream of the nucleic acid sequence encoding the first antigen-binding domain, and downstream of the nucleic acid sequence encoding the promoter.

In some embodiments, in the method, the nucleic acid sequence encoding the recognition enzyme is located down-stream of the nucleic acid sequence encoding the non-antigen-binding function domain.

In some embodiments, the cleavable peptide is selected from the group consisting of: P2A, T2A, F2A, E2A, BmCPV2A, and BmIFV2A.

In some embodiments, in the method, the nucleic acid sequence encoding the cleavable peptide is located at a 3'-terminal and/or 5'-terminal of the nucleic acid sequence encoding the recognition enzyme.

In some embodiments, in the method, the nucleic acid sequence encoding the cleavable peptide is located at a 3'-terminal of the nucleic acid sequence encoding the non-antigen-binding function domain.

In some embodiments, in the method, the nucleic acid sequence encoding the cleavable peptide is located at a 3'-terminal of the nucleic acid sequence encoding the leader peptide.

In some embodiments, in the method, two types of chimeric antigen receptors are expressed.

In some embodiments, the method comprises two differ-ent pairs of LoxP sites.

In some embodiments, in the method, a first pair of the LoxP sites comprises therebetween the nucleic acid sequence encoding the first antigen-binding domain.

In some embodiments, in the method, a second pair of the LoxP sites comprises therebetween the nucleic acid sequence encoding the second antigen-binding domain.

In some embodiments, the method comprises at least one pair of LoxP sites with reverse-complementing sequences.

In some embodiments, in the method, the one pair of LoxP sites with reverse-complementing sequences com-prises therebetween the nucleic acid sequence encoding the first antigen-binding domain and a reverse-complementing sequence of the nucleic acid sequence encoding the second antigen-binding domain; or, comprises therebetween a reverse-complementing sequence of the nucleic acid sequence encoding the first antigen-binding domain, and the nucleic acid sequence encoding the second antigen-binding domain.

In some embodiments, in the method, three types of chimeric antigen receptors are expressed.

In some embodiments, the method comprises four differ-ent pairs of LoxP sites.

In some embodiments, in the method, a first pair of the LoxP sites comprises therebetween the nucleic acid sequence encoding the first antigen-binding domain and the nucleic acid sequence encoding the second antigen-binding domain.

In some embodiments, in the method, a second pair of the LoxP sites comprises therebetween the nucleic acid sequence encoding the first antigen-binding domain.

In some embodiments, in the method, a third pair of the LoxP sites comprises therebetween the nucleic acid sequence encoding the second antigen-binding domain and a nucleic acid sequence encoding a third antigen-binding domain.

In some embodiments, in the method, a fourth pair of the LoxP sites comprises therebetween the nucleic acid sequence encoding the third antigen-binding domain.

In some embodiments, the method comprises a nucleotide sequence as set forth in any one of SEQ ID NOs. 75-77 and 83-84.

Other aspects and advantages of the present application may be readily perceived by those skilled in the art from the detailed description below. The detailed description below only illustrates and describes the exemplary embodiments of the present application. As would be appreciated by those skilled in the art, the content of the present application allows those killed in the art to change the specific embodi-ments disclosed without departing from the spirit and scope involved in the present application. Accordingly, the accom-panying drawings and the description in the specification of the present application are merely for an exemplary but not restrictive purpose.

BRIEF DESCRIPTION OF THE DRAWINGS

The specific features of the invention involved in the present application are listed in the appended claims. The characteristics and advantages of the invention involved in the present application may be better understood by refer-ring to the exemplary embodiments and the accompanying drawings described in detail below. The accompanying drawings are briefly illustrated as follows:

FIGS. 9A-G show the transfection of human T lympho-cytes by single-target and dual-target lentiviral vector-pack-aged viruses according to the present application;

FIG. 17 shows the relapse-free survival (RFS) and overall survival (OS) of enrolled patients according to the present application.

DETAILED DESCRIPTION OF THE PREFERRED EMBODIMENTS

The embodiments of the invention of the present application will be illustrated by specific examples below. Those familiar with this technology may easily understand other advantages and effects of the invention of the present application from the content disclosed in the specification.

TERMS & DEFINITIONS

In the present application, the term "nucleic acid molecule expressing at least two types of chimeric antigen receptors (CARs)" generally refers to a recombinant nucleic acid sequence capable of expressing a recombinant polypeptide construct comprising at least two extracellular antigen-binding domains. In some embodiments, the nucleic acid molecule expressing at least two types of chimeric antigen receptors (CARs) comprises at least one nucleic acid sequence encoding a first antigen-binding domain, a nucleic acid sequence encoding a second antigen-binding domain, and nucleic acid sequences of at least one pair of LoxP sites, with each pair of the LoxP sites recognizable by a corresponding LoxP site recognition enzyme, wherein the first antigen-binding domain and the second antigen-binding domain different from the first antigen-binding domain are involved in the composition of a first chimeric antigen receptor and a second chimeric antigen receptor, respectively, and wherein at least one pair of the LoxP sites comprises therebetween at least one nucleic acid sequence encoding the antigen-binding domain. In one aspect, antigens targeted by the antigen-binding domains may be CD19, CD22, and CD20. In one aspect, the nucleic acid molecule expressing at least two types of chimeric antigen receptors (CARs) comprise a promoter nucleic acid sequence and a leader peptide nucleic acid sequence. In one aspect, the nucleic acid molecule expressing at least two types of chimeric antigen receptors (CARs) comprise a nucleic acid sequence encoding a non-antigen-binding function domain, wherein the non-antigen binding function domain comprises a hinge region, a transmembrane region, a co-stimulatory domain, and/or an intracellular signaling domain. In one aspect, the nucleic acid molecule expressing at least two types of chimeric antigen receptors (CARs) comprises a co-stimulatory domain, which may be 4-1BB, OX40, CD2, CD27, CD28, CDS, ICAM-1, LFA-1 and ICOS. In one aspect, the nucleic acid molecule expressing at least two types of chimeric antigen receptors (CARs) comprises an intracellular signaling domain, which may be CD3ζ, FccRIγ and ZAP70. In one aspect, the nucleic acid molecule expressing at least two types of chimeric antigen receptors (CARs) comprises a cleavable peptide, which may be P2A, T2A, F2A, E2A, BmCPV2A and BmIFV2A.

Figure 4:
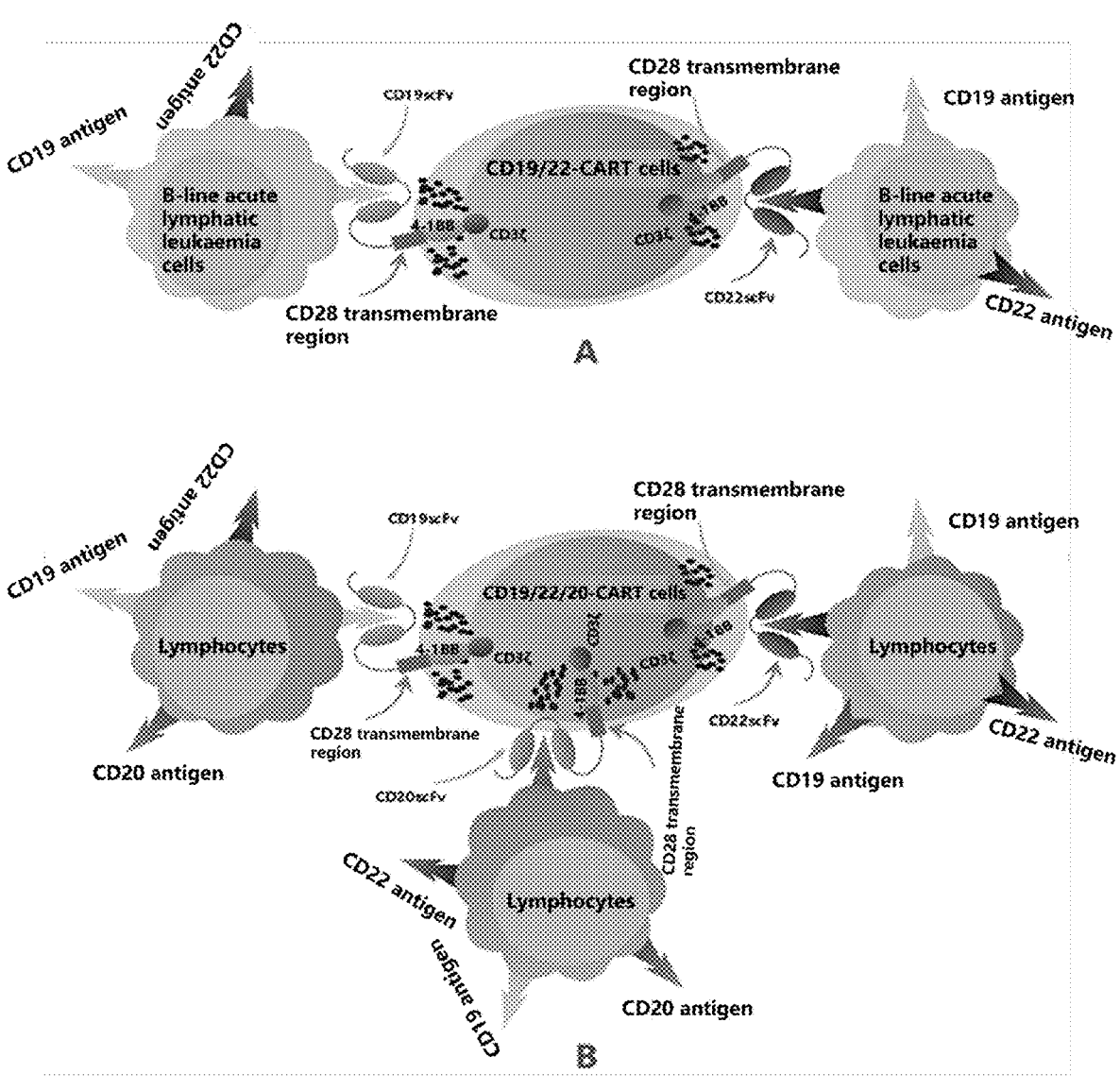
FIG. 4 shows schematic structural diagrams of chimeric antigen receptor structures reconstituted under the action of CRE into two or more single complete chimeric antigen receptor structures to kill target cells, according to the present application.

In the present application, the term "a method for preparing a chimeric antigen receptor" generally refers to a method for reconstituting chimeric antigen receptors (CAR) at two or more targets into two or more single complete chimeric antigen receptors under the action of a LoxP site recognition enzyme. In one aspect, this method requires a nucleic acid molecule comprising a nucleic acid sequence encoding a first antigen-binding domain, a nucleic acid sequence encoding a second antigen-binding domain, and at least one pair of LoxP sites, with each pair of the LoxP sites recognizable by a corresponding LoxP site recognition enzyme, wherein the first antigen-binding domain and the second antigen-binding domain different from the first antigen-binding domain are involved in the composition of a first chimeric antigen receptor and a second chimeric antigen receptor, respectively, and wherein at least one pair of the LoxP sites comprises therebetween at least one nucleic acid sequence encoding the antigen-binding domain. In one aspect, it is required to contact the nucleic acid molecule with the corresponding LoxP site recognition enzyme. In one aspect, during preparation, it is required to remove the sequence between each pair of the LoxP sites respectively to form an expression molecule comprising only one nucleic acid molecule encoding the antigen-binding domain, wherein the expression molecule can express a chimeric antigen receptor. In the present application, the chimeric antigen receptors (CAR) at two or more targets are reconstituted into two or more single complete chimeric antigen receptors under the action of the LoxP site recognition enzyme to kill tumor cells (as shown in FIG. 4).

In the present application, the term "CD3ζ", also written as CD3zeta, generally refers to an amino acid residue from a cytoplasm domain of a ζ-chain of a cluster of differentiation 3 (CD3). In some embodiments, CD3ζ may act as an intracellular signaling domain of CAR to synergistically activate T cells together with 4-1BB to produce targeting cytotoxicity. For example, the CD3ζ may comprise a nucleic acid sequence as set forth in SEQ ID NO: 73. For example, the CD3ζ may comprise a nucleic acid sequence as set forth in SEQ ID NO: 82.

In the present application, the term "specific single-chain antibody (scFv)" generally refers to linker-linked molecules of an antibody heavy chain variable region (VH) and an antibody light chain variable region (VL). See, for example, Bird et al., Science, 242: 423-426 (1988); and Huston et al., Proc. Natl. Acad. Sci. USA, 85: 5879-5883 (1988). In some embodiments, the heavy and light chain variable regions of scFv may be derived from CD19, CD20 or CD22.

In the present application, the term "CD19 antigen" generally refers to an important membrane antigen that is on a human B lymphocyte and associated with proliferation and differentiation. The amino acid sequence of human CD19 can be found in UniProt/Swiss-Prot at Accession No. P15391. In the present application, the antigen targeted by the antigen-binding domain of the nucleic acid molecule expressing at least two types of chimeric antigen receptors (CARs) may be CD19.

In the present application, the term "CD22 antigen" generally refers to an important membrane antigen that is on a human B lymphocyte and associated with proliferation and differentiation. The amino acid sequence of human CD22 can be found in UniProt/Swiss-Prot at Accession No. P20273. In the present application, the antigen targeted by the antigen-binding domain of the nucleic acid molecule expressing at least two types of chimeric antigen receptors (CARs) may be CD22.

In the present application, the term "CD20 antigen" generally refers to an important membrane antigen that is on a human B lymphocyte and associated with proliferation and differentiation. The amino acid sequence of human CD20 can be found in UniProt/Swiss-Prot at Accession No. P11836. In the present application, the antigen targeted by the antigen-binding domain of the nucleic acid molecule expressing at least two types of chimeric antigen receptors (CARs) may be CD20.

In the present application, the term "4-1BB" generally refers to a T cell costimulatory molecule. In some embodiments, 4-1BB acts as an intracellular signal co-stimulatory molecule in the CART structure to synergistically activate T cells together with CD3ζ to produce targeting cytotoxicity. In some embodiments, the 4-1BB may comprise a nucleic acid sequence as set forth in SEQ ID NO: 72. In some embodiments, the 4-1BB may comprise a nucleic acid sequence as set forth in SEQ ID NO: 81.

DETAILED DESCRIPTION OF THE INVENTION

Nucleic Acid Molecule

Figure 1A:
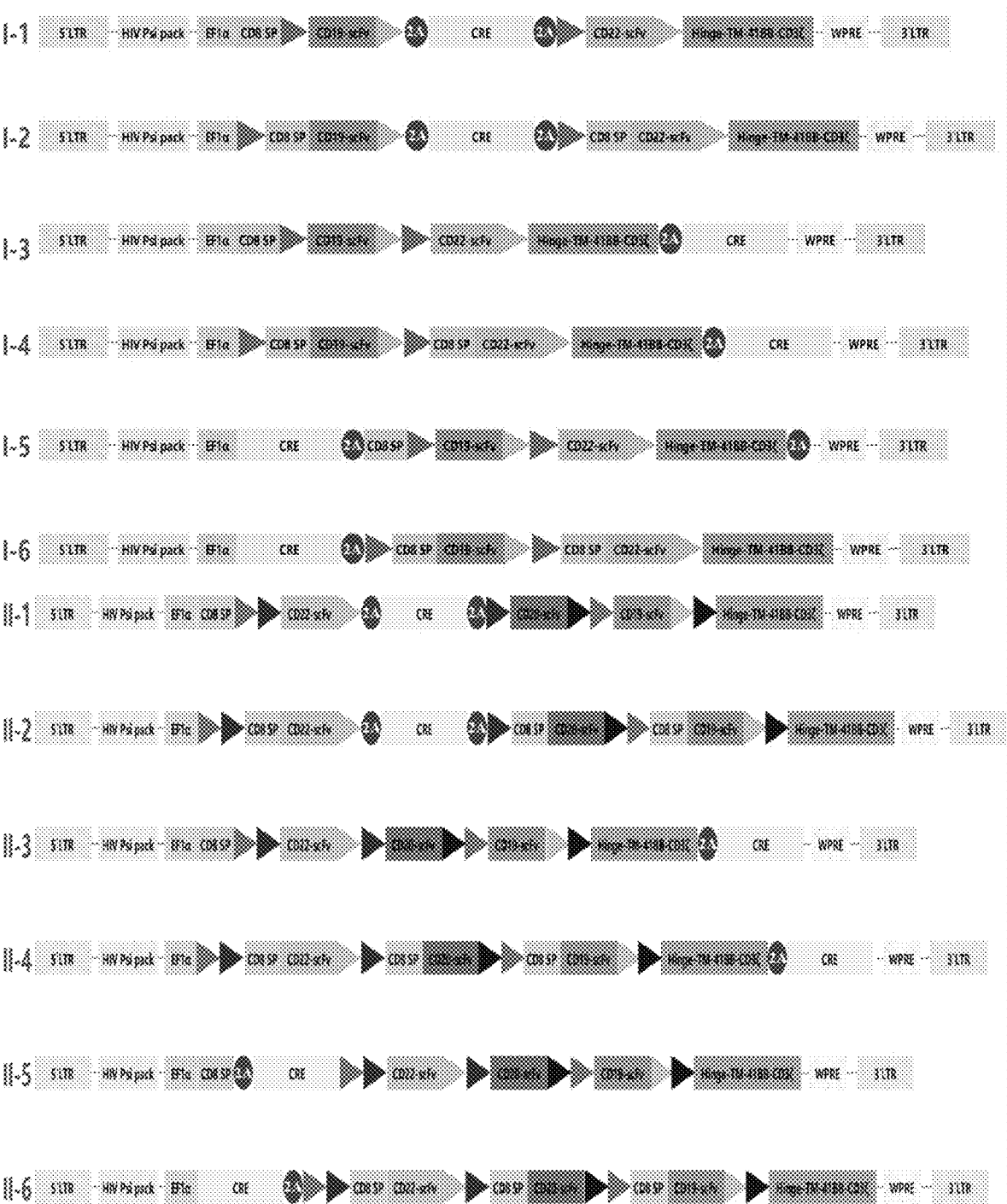
FIGS. 1A-B show schematic structural diagrams of vec-tors (I-1~III-6) genetically engineered with chimeric antigen receptors according to the present application.
Figure 1B:
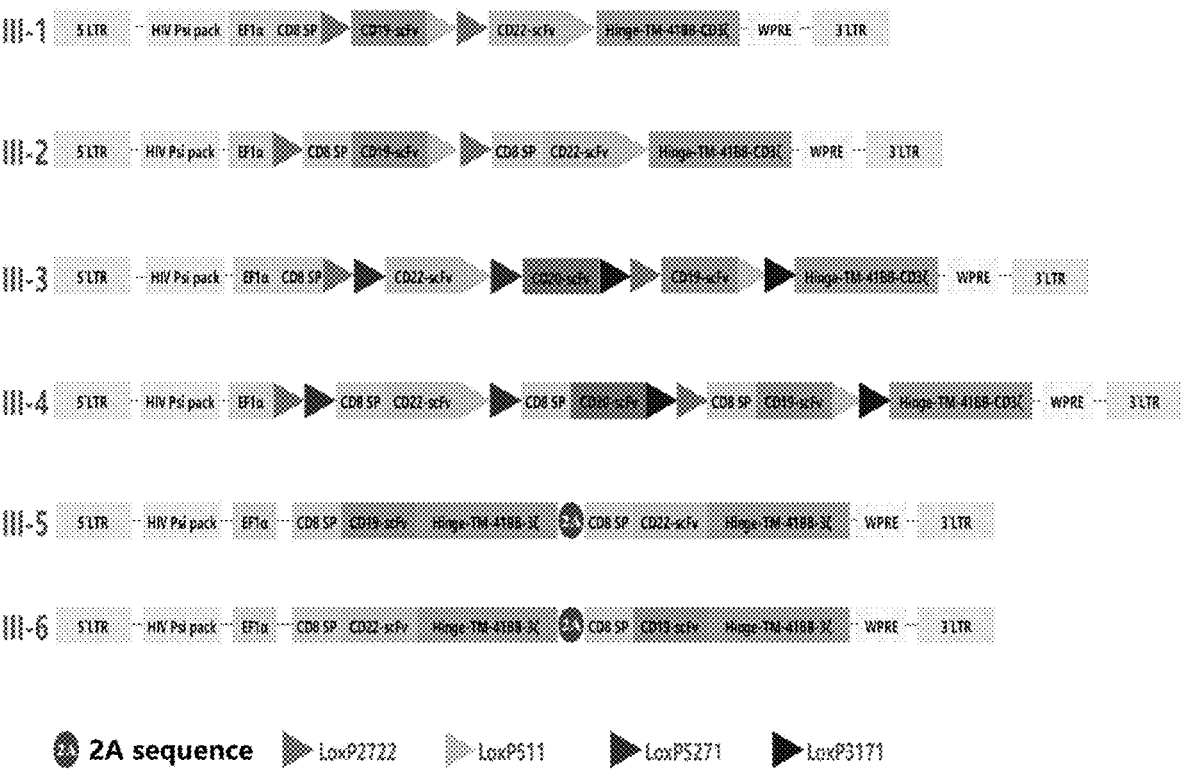
Figure 2:
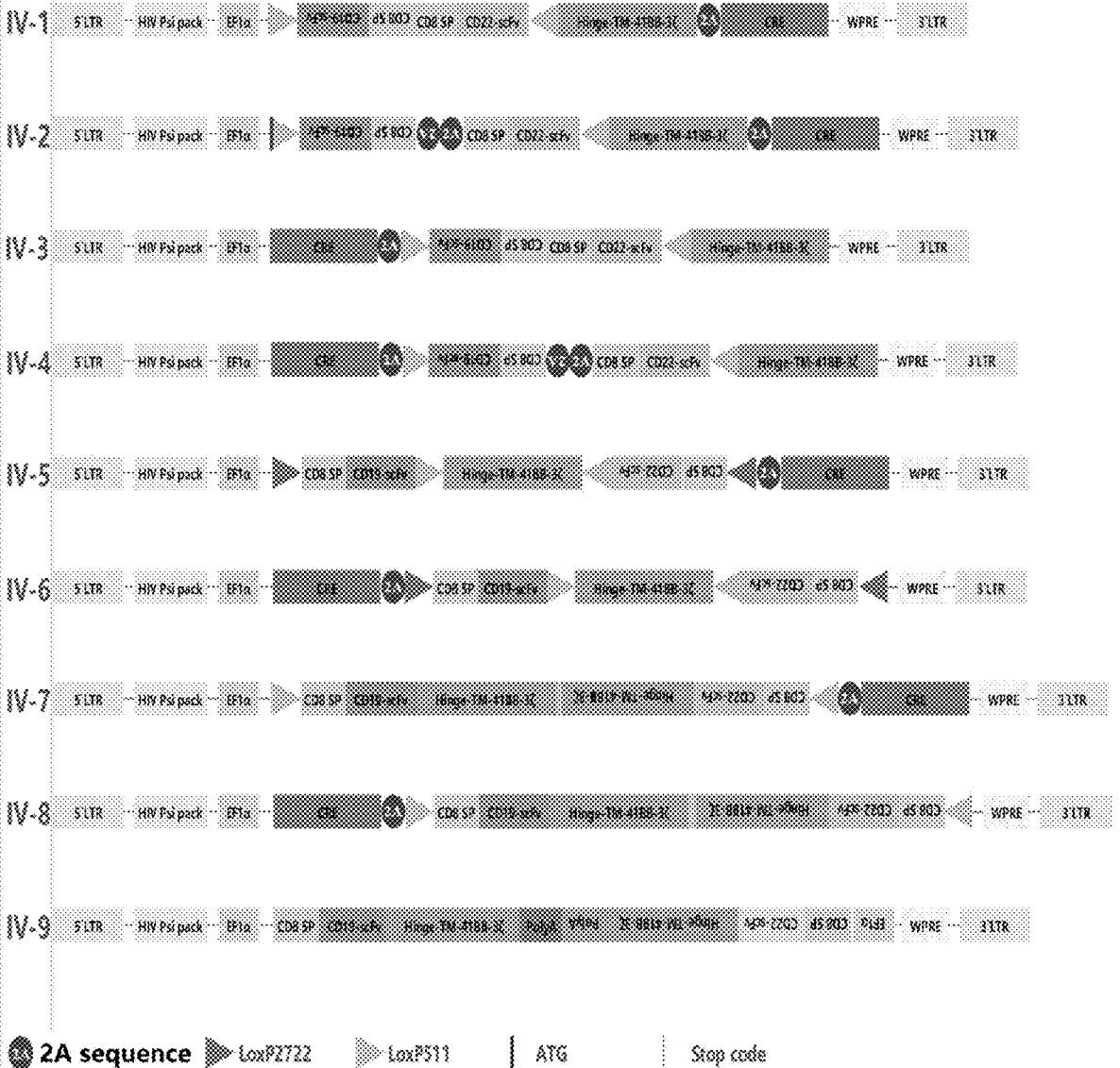
FIG. 2 shows schematic structural diagrams of vectors (IV-1-IV-9) genetically engineered with chimeric antigen receptors according to the present application.

In one aspect, the present application provides a nucleic acid molecule expressing at least two types of chimeric antigen receptors (CARs), comprising a nucleic acid sequence encoding a first antigen-binding domain, a nucleic acid sequence encoding a second antigen-binding domain, and nucleic acid sequences and/or cleavable peptide sequences of at least one pair of LoxP sites, with each pair of the LoxP sites recognizable by a corresponding LoxP site recognition enzyme, wherein the first antigen-binding domain and the second antigen-binding domain different from the first antigen-binding domain are involved in the composition of a first chimeric antigen receptor and a second chimeric antigen receptor, respectively, and wherein at least one pair of the LoxP sites comprises therebetween at least one nucleic acid sequence encoding the antigen-binding domain (as shown in FIGS. 1 and 2).

In the present application, the nucleic acid molecule may express at least two types of chimeric antigen receptors, and the nucleic acid molecule may comprise a nucleic acid sequence encoding a first antigen-binding domain, a nucleic acid sequence encoding a second antigen binding domain, and a cleavable peptide sequence. In some embodiments, the sequence of the cleavable peptide is located between the nucleic acid sequence encoding the first antigen-binding domain and the nucleic acid sequence encoding the second antigen-binding domain.

In the nucleic acid molecule of the present application, the LoxP sites may be selected from the group consisting of: wild-type LoxP, LoxP2722, LoxP511, LoxP5271 and LoxP3171. For example, the LoxP site may comprise a nucleotide sequence as set forth in any one selected from the group consisting of: SEQ ID NO: 12, SEQ ID NO: 13, SEQ ID NO: 14, SEQ ID NO: 15, and SEQ ID NO: 16.

In the nucleic acid molecule of the present application, the antigen-binding domains may specifically bind to tumor antigens. For example, the antigen-binding domains may comprise any tumor antigen or a combination thereof selected from the group consisting of: A33, B7H3, BCMA, CA125, CD1, CD10, CD102, CD11a, CD11b, CD123, CD13, CD133, CD134, CD137, CD138, CD14, CD15, CD19, CD2, CD20, CD200, CD21, CD22, CD23, CD25, CD27, CD28, CD3, CD30, CD33, CD34, CD36, CD37, CD38, CD4, CD40, CD41, CD42, CD43, CD44, CD45, CD5, CD56, CD58, CD65, CD66c, CD7, CD70, CD73, CD74, CD8, CD80, CD81, CD86, CD9, CD94, CD97, CD99, CEA, CEACAM6, CLL1, CS1, DLL1, DLL3, EGFR, EGFR VIII, ERBB2, FGF19, GD2, GD3, HER3, IL3Ra, NCAM, NG2, NKG2A, NTBA, PD-1, PDL-1, PSGL1, PSMA, ROR1 and VEGF. For example, the anti-gen-binding domain may comprise any tumor antigen or a combination thereof selected from the group consisting of: CD19, CD22, CD20, GD2, B7H3, CD7, CD5, CD33, CD123, CLL1, ROR1 and CD38.

In the present application, the nucleic acid molecule may comprise a nucleic acid sequence of a promoter. For example, the promoter may be EF1α, CMV, MSCV, and UbC. For example, a sequence of the promoter may comprise a nucleic acid sequence as set forth in SEQ ID NO: 1.

In some embodiments, in the nucleic acid molecule, the leader peptide may comprise a leader peptide moiety derived from a protein selected from the group consisting of: CD8, CD33, and CD45.

In some embodiments, the nucleic acid molecule may comprise at least one nucleic acid sequence encoding a leader peptide. For example, a sequence of the leader peptide may comprise a nucleotide sequence as set forth in any one selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 78.

In the present application, the nucleic acid molecule may comprise a nucleic acid sequence encoding a non-antigen-binding function domain of a chimeric antigen receptor. For example, the non-antigen binding function domain may comprise a hinge region, a transmembrane region, a co-stimulatory domain, and/or an intracellular signaling domain.

In the present application, in the nucleic acid molecule, the hinge region may comprise a hinge region derived from a protein selected from the group consisting of: CD8, CD28, and 4-1BB. For example, the hinge region may comprise a nucleic acid sequence as set forth in SEQ ID NO: 70.

For example, the hinge region may comprise a nucleic acid sequence as set forth in SEQ ID NO: 79.

In the present application, in the nucleic acid molecule, the transmembrane region may comprise a transmembrane region derived from a protein selected from the group consisting of: CD8, CD28, and CD19. For example, the transmembrane region may comprise a nucleic acid sequence as set forth in SEQ ID NO: 71. For example, the transmembrane region may comprise a nucleic acid sequence as set forth in SEQ ID NO: 80.

In the present application, in the nucleic acid molecule, the co-stimulatory domain may comprise a co-stimulatory domain derived from a protein selected from the group consisting of: 4-1BB, OX40, CD2, CD27, CD28, CDS, ICAM-1, LFA-1, and ICOS. For example, the co-stimulatory domain may be derived from 4-1BB, with a nucleic acid sequence as set forth in SEQ ID NO: 72 or SEQ ID NO: 81.

In the present application, in the nucleic acid molecule, the intracellular signaling domain may comprise an intracellular signaling domain derived from a protein selected from the group consisting of: CD3ζ, FccRIγ, and ZAP70. For example, the intracellular signaling domain may be derived from CD3ζ, with a nucleic acid sequence as set forth in SEQ ID NO: 73 or SEQ ID NO: 82.

In the present application, the nucleic acid molecule may comprise a nucleic acid sequence encoding a recognition enzyme specifically recognizing the LoxP sites, wherein the recognition enzyme may be selected from the group consisting of: CRE and Brec1. For example, the nucleic acid sequence encoding the recognition enzyme specifically recognizing the LoxP sites may be derived from CRE, with a sequence as set forth in SEQ ID NO: 74.

In the present application, the nucleic acid molecule may comprise at least one nucleic acid sequence encoding a cleavable peptide, wherein the cleavable peptide may be selected from the group consisting of: P2A, T2A, F2A, E2A, BmCPV2A, and BmIFV2A. For example, the cleavable peptide may be derived from P2A and T2A, with a sequence that may comprise a nucleic acid sequence as set forth in any one selected from the group consisting of: SEQ ID NO: 17, SEQ ID NO: 18, SEQ ID NO: 19, and SEQ ID NO: 20.

In the present application, the nucleic acid molecule may comprise a nucleic acid sequence encoding a backbone vector. For example, the backbone vector may comprise an HIV packaging vector, with a sequence as set forth in SEQ ID NO: 21.

In the present application, the nucleic acid molecule may comprise a 5'LTR sequence as set forth in SEQ ID NO: 22.

In the present application, the nucleic acid molecule may comprise a 3'LTR sequence as set forth in SEQ ID NO: 22.

In the present application, the nucleic acid molecule may comprise a nucleic acid sequence encoding WPRE, with the sequence as set forth in SEQ ID NO: 23.

In the present application, in the nucleic acid molecule, the 5'-terminal of the nucleic acid sequence encoding the leader peptide may be linked to the 3'-terminal of the nucleic acid sequence encoding the promoter, or the 3'-terminal of the nucleic acid sequence encoding the leader peptide may be linked to the 5'-terminal of the nucleic acid sequence encoding the antigen-binding domain.

In the present application, in the nucleic acid molecule, the 5'-terminal of the nucleic acid sequence of the promoter may be linked to the 3'-terminal of the nucleic acid sequence of the HIV packaging vector, or the 3'-terminal of the nucleic acid sequence encoding the promoter may be linked to the 5'-terminal of the nucleic acid sequence encoding the leader peptide.

In the present application, in the nucleic acid molecule, the nucleic acid sequence encoding the non-antigen-binding function domain may be located downstream of the nucleic acid sequence encoding the antigen-binding domain, or, between the nucleic acid sequence encoding the first antigen-binding domain and the nucleic acid sequence encoding the second antigen-binding domain.

In the present application, in the nucleic acid molecule, the nucleic acid sequence encoding the first antigen-binding domain may be located downstream of the nucleic acid sequence encoding the leader peptide.

In the present application, in the nucleic acid molecule, the nucleic acid sequence encoding the second antigen-binding domain may be located upstream of the nucleic acid sequence encoding the non-antigen-binding function domain.

In the present application, in the nucleic acid molecule, the nucleic acid sequence encoding WPRE may be located downstream of the nucleic acid sequence encoding the non-antigen-binding function domain. For example, the nucleic acid sequence encoding WPRE may be a sequence as set forth in SEQ ID NO: 23.

In the present application, in the nucleic acid molecule, the nucleic acid sequence encoding the backbone vector may be located upstream of the nucleic acid sequence encoding the promoter. For example, the nucleic acid sequence encoding the backbone vector may be a sequence as set forth in SEQ ID NO: 21.

In the present application, the 5'LTR sequence may be located at a 5'-terminal of the nucleic acid molecule.

In the present application, the 3'LTR sequence may be located at a 3'-terminal of the nucleic acid molecule.

In the present application, the nucleic acid sequence encoding the recognition enzyme may be located between the nucleic acid sequence encoding the first antigen-binding domain and the nucleic acid sequence encoding the second antigen-binding domain.

In the present application, in the nucleic acid molecule, the nucleic acid sequence encoding the recognition enzyme may be located upstream of the nucleic acid sequence encoding the first antigen-binding domain, and downstream of the nucleic acid sequence encoding the promoter.

In the present application, in the nucleic acid molecule, the nucleic acid sequence encoding the recognition enzyme may be located downstream of the nucleic acid sequence encoding the non-antigen-binding function domain.

In the present application, in the nucleic acid molecule, the nucleic acid sequence encoding the cleavable peptide may be located at the 3'-terminal and/or 5'-terminal of the nucleic acid sequence encoding the recognition enzyme.

In the present application, in the nucleic acid molecule, the nucleic acid sequence encoding the cleavable peptide may be located at the 3'-terminal of the nucleic acid sequence encoding the non-antigen-binding function domain.

In the present application, in the nucleic acid molecule, the nucleic acid sequence encoding the cleavable peptide may be located at the 3'-terminal of the nucleic acid sequence encoding the leader peptide.

In the present application, in the nucleic acid molecule, the nucleic acid sequence encoding the LoxP site may be located at the 5'-terminal or 3'-terminal of the nucleic acid sequence encoding the leader peptide.

In the present application, in the nucleic acid molecule, the nucleic acid sequence encoding the LoxP site may be located at the 3'-terminal or 5'-terminal of the nucleic acid sequence encoding the first antigen-binding domain.

In the present application, in the nucleic acid molecule, the nucleic acid sequence encoding the LoxP site may be located at the 3'-terminal or 5'-terminal of the nucleic acid sequence encoding the second antigen-binding domain.

In the present application, the nucleic acid molecule may express two types of chimeric antigen receptors.

In the present application, the nucleic acid molecule may comprise two different pairs of LoxP sites.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the leader peptide, a nucleic acid sequence encoding a LoxP site 1, the nucleic acid sequence encoding the first antigen-binding domain, a nucleic acid sequence encoding a LoxP site 2, the nucleic acid sequence encoding the cleavable peptide, the nucleic acid sequence encoding the recognition enzyme, the nucleic acid sequence encoding the cleavable peptide, the nucleic acid sequence encoding the LoxP site 1, the nucleic acid sequence encoding the second antigen-binding domain, the nucleic acid sequence encoding the LoxP site 2, the nucleic acid sequence encoding the non-antigen-binding function domain, the WPRE, and the 3'LTR.

In the present application, the nucleic acid molecule may comprise, from the 5'-terminal to the 3'-terminal, 5' LTR, the HIV packaging vector, the nucleic acid sequence encoding the promoter, the nucleic acid sequence encoding the leader peptide, the nucleic acid sequence encoding the LoxP site 1, the nucleic acid sequence encoding the first antigen-binding domain, the nucleic acid sequence encoding the LoxP site 2, the nucleic acid sequence encoding the cleavable peptide, the nucleic acid sequence encoding the recognition enzyme, the nucleic acid sequence encoding the cleavable peptide, the nucleic acid sequence encoding the LoxP site 1, the nucleic acid sequence encoding the leader peptide, the nucleic acid sequence encoding the second antigen-binding domain, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the leader peptide, the nucleic acid sequence encoding the LoxP site 1, the nucleic acid sequence encoding the first antigen-binding domain, the nucleic acid sequence encoding the LoxP site 2, the nucleic acid sequence encoding the LoxP site 1, the nucleic acid sequence encoding the second antigen-binding domain, the nucleic acid sequence encoding the LoxP site 2, the nucleic acid sequence encoding the non-antigen-binding function domain, the nucleic acid sequence encoding the cleavable peptide, the nucleic acid sequence encoding the recognition enzyme, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the LoxP site 1, the nucleic acid sequence encoding the leader peptide, the nucleic acid sequence encoding the first antigen-binding domain, the nucleic acid sequence encoding the LoxP site 2, the nucleic acid sequence encoding the LoxP site 1, the nucleic acid sequence encoding the leader peptide, the nucleic acid sequence encoding the second antigen-binding domain, the nucleic acid sequence encoding the LoxP site 2, the nucleic acid sequence encoding the non-antigen-binding function domain, the nucleic acid sequence encoding the cleavable peptide, the nucleic acid sequence encoding the recognition enzyme, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the recognition enzyme, the nucleic acid sequence encoding the cleavable peptide, the nucleic acid sequence encoding the leader peptide, the nucleic acid sequence encoding the LoxP site 1, the nucleic acid sequence encoding the first antigen-binding domain, the nucleic acid sequence encoding the LoxP site 2, the nucleic acid sequence encoding the LoxP site 1, the nucleic acid sequence encoding the second antigen-binding domain, the nucleic acid sequence encoding the LoxP site 2, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the recognition enzyme, the nucleic acid sequence encoding the cleavable peptide, the nucleic acid sequence encoding the LoxP site 1, the nucleic acid sequence encoding the leader peptide, the nucleic acid sequence encoding the first antigen-binding domain, the nucleic acid sequence encoding the LoxP site 2, the nucleic acid sequence encoding the LoxP site 1, the nucleic acid sequence encoding the leader peptide, the nucleic acid sequence encoding the second antigen-binding domain, the nucleic acid sequence encoding the LoxP site 2, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the leader peptide, the nucleic acid sequence encoding the LoxP site 1, the nucleic acid sequence encoding the first antigen-binding domain, the nucleic acid sequence encoding the LoxP site 2, the nucleic acid sequence encoding the LoxP site 1, the nucleic acid sequence encoding the second antigen-binding domain, the nucleic acid sequence encoding the LoxP site 2, the nucleic acid sequence encoding the non-antigen-binding function domain, the WPRE, and the 3'LTR.

Figure 3:
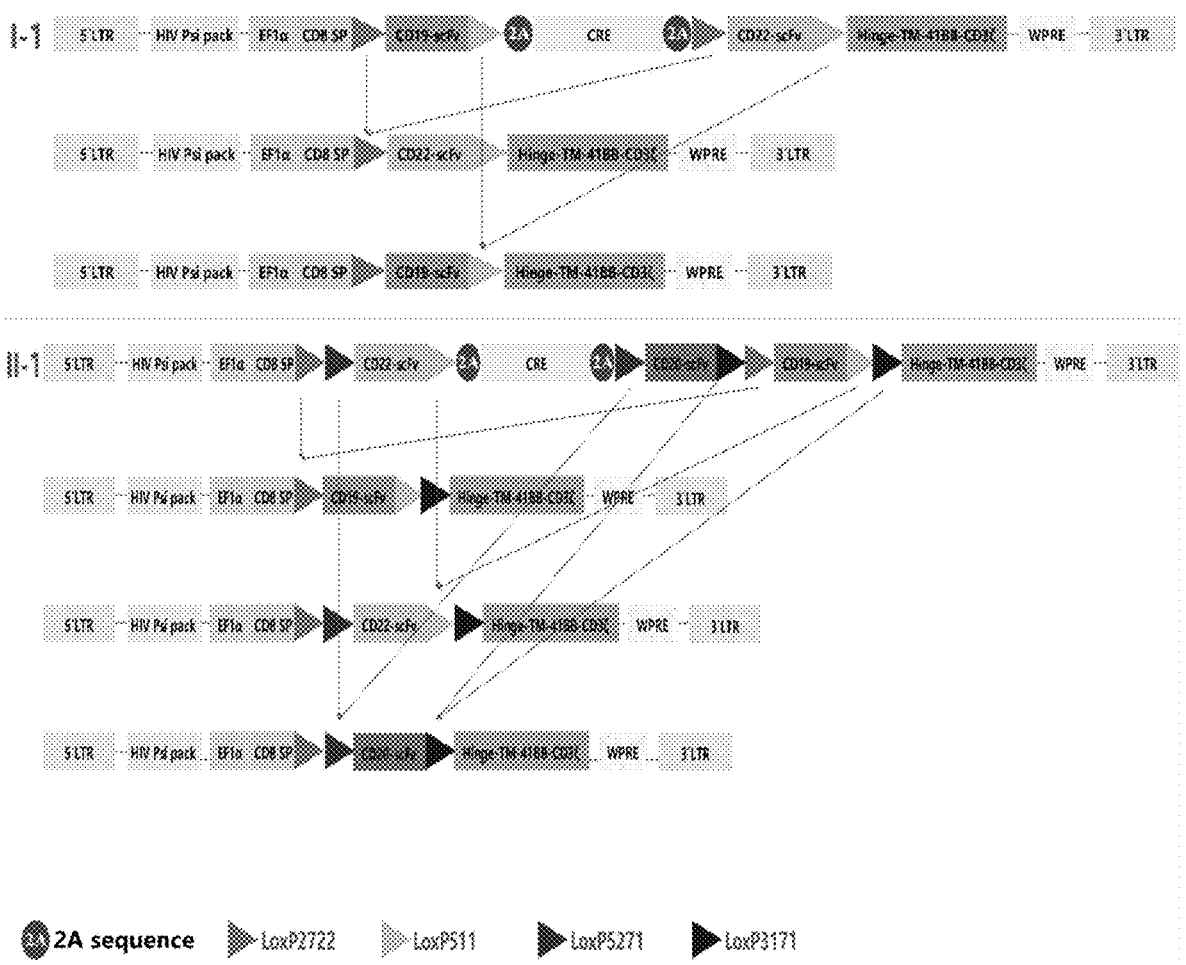
FIG. 3 shows schematic structural diagrams of chimeric antigen receptor structures reconstituted under the action of CRE into two or more single complete chimeric antigen receptor structures, according to the present application.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the LoxP site 1, the nucleic acid sequence encoding the leader peptide, the nucleic acid sequence encoding the first antigen-binding domain, the nucleic acid sequence encoding the LoxP site 2, the nucleic acid sequence encoding the LoxP site 1, the nucleic acid sequence encoding the leader peptide, the nucleic acid sequence encoding the second antigen-binding domain, the nucleic acid sequence encoding the LoxP site 2, the nucleic acid sequence encoding the non-antigen-binding function domain, the WPRE, and the 3'LTR.
In the present application, the nucleic acid molecule may contact the corresponding LoxP site recognition enzyme, the sequence between each pair of the LoxP sites may be removed respectively to form an expression molecule comprising only one nucleic acid molecule encoding the antigen-binding domain, and the expression molecule may express a chimeric antigen receptor. For example, the corresponding LoxP site recognition enzyme may respectively contact the nucleic acid sequences encoding the LoxP sites 1 and the nucleic acid sequences encoding the LoxP sites 2, and the sequences between the two LoxP sites 1 and the two LoxP sites 2 can be respectively removed, such that the nucleic acid molecule is reconstituted into an expression molecule capable of expressing two single and complete chimeric antigen receptor structures carrying the first antigen-binding domain and the second antigen-binding domain, respectively (as shown in FIG. 3).

In the present application, in the nucleic acid molecule, a first pair of the LoxP sites may comprise therebetween the nucleic acid sequence encoding the first antigen-binding domain. For example, the first antigen may be CD19, and the CD19-targeted antigen-binding domain may comprise a light chain variable region and a heavy chain variable region.

For example, the light chain variable region of the CD19-targeted antigen-binding domain may comprise a nucleic acid sequence as set forth in any one selected from the group consisting of: SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33; and the heavy chain variable region of the CD19-targeted antigen-binding domain may comprise a nucleic acid sequence as set forth in any one selected from the group consisting of: SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43.

In the present application, in the nucleic acid molecule, a first pair of the LoxP sites may comprise therebetween the nucleic acid sequence encoding the first antigen-binding domain. For example, the first antigen may be GD2, and the GD2-targeted antigen-binding domain may comprise a light chain variable region and a heavy chain variable region.

For example, the nucleic acid sequence of the light chain variable region of the GD2-targeted antigen-binding domain may be as set forth in SEQ ID NO: 44, SEQ ID NO: 45, SEQ ID NO: 46, and SEQ ID NO: 48; and the nucleic acid sequence of the heavy chain variable region of the GD2-targeted antigen-binding domain may be as set forth in SEQ ID NO: 49, SEQ ID NO: 50, SEQ ID NO: 51, and SEQ ID NO: 53.

In the present application, in the nucleic acid molecule, a second pair of the LoxP sites may comprise therebetween the nucleic acid sequence encoding the second antigen-binding domain. For example, the second antigen may be CD20, and a CD20-targeted antigen-binding domain may comprise a light chain variable region and a heavy chain variable region.

For example, the light chain variable region of the CD20-targeted antigen-binding domain may comprise a nucleic acid sequence as set forth in any one selected from the group consisting of: SEQ ID NO: 56, SEQ ID NO: 57, and SEQ ID NO: 58; and the heavy chain variable region of the CD20-targeted antigen-binding domain may comprise a nucleic acid sequence as set forth in any one selected from the group consisting of: SEQ ID NO: 59, SEQ ID NO: 60, and SEQ ID NO: 61.

In the present application, in the nucleic acid molecule, a second pair of the LoxP sites may comprise therebetween the nucleic acid sequence encoding the second antigen-binding domain. For example, the second antigen may be CD22, and a CD22-targeted antigen-binding domain may comprise a light chain variable region and a heavy chain variable region.

For example, the light chain variable region of the CD22-targeted antigen-binding domain may comprise a nucleic acid sequence as set forth in any one selected from the group consisting of: SEQ ID NO: 62, SEQ ID NO: 63, SEQ ID NO: 64, and SEQ ID NO: 65; and the heavy chain variable region of the CD22-targeted antigen-binding domain may comprise a nucleic acid sequence as set forth in any one selected from the group consisting of: SEQ ID NO: 66, SEQ ID NO: 67, SEQ ID NO: 68, and SEQ ID NO: 69.

In the present application, in the nucleic acid molecule, a second pair of the LoxP sites may comprise therebetween the nucleic acid sequence encoding the second antigen-binding domain. For example, the second antigen may be B7H3, and a B7H3-targeted antigen-binding domain may comprise a light chain variable region and a heavy chain variable region.

For example, the nucleic acid sequence of the light chain variable region of the B7H3-targeted antigen-binding domain may be as set forth in SEQ ID NO: 47; and the nucleic acid sequence of the heavy chain variable region of the B7H3-targeted antigen-binding domain may be as set forth in SEQ ID NO: 52.

For example, the nucleic acid sequence of the light chain variable region of the B7H3-targeted antigen-binding domain may be as set forth in SEQ ID NO: 54; and the nucleic acid sequence of the heavy chain variable region of the B7H3-targeted antigen-binding domain may be as set forth in SEQ ID NO: 55.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the leader peptide, the nucleic acid sequence encoding the first antigen-binding domain, the nucleic acid sequence encoding the non-antigen-binding function domain, the sequence encoding the cleavable peptide, the nucleic acid sequence encoding the leader peptide, the nucleic acid sequence encoding the second antigen-binding domain, the nucleic acid sequence encoding the non-antigen-binding function domain, the WPRE, and the 3'LTR. In the present application, an expression molecule comprising only one nucleic acid molecule encoding the antigen-binding domain may be formed by means of the sequence of the cleavable peptide, and the expression molecule may express a chimeric antigen receptor. For example, the first antigen may be selected from the group consisting of: CD19, CD22, CD20, GD2 and B7H3. For example, the second antigen may be selected from the group consisting of: CD19, CD22, CD20, GD2 and B7H3.

For example, the first antigen may be CD19, and a CD19-targeted antigen-binding domain may comprise a light chain variable region and a heavy chain variable region; and the second antigen may be CD22, and a CD22-targeted antigen-binding domain may comprise a light chain variable region and a heavy chain variable region. For example, the light chain variable region of the CD19-targeted antigen-binding domain may comprise a nucleic acid sequence as set forth in any one selected from the group consisting of: SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33; and the heavy chain variable region of the CD19-targeted antigen-binding domain may comprise a nucleic acid sequence as set forth in any one selected from the group consisting of: SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43. For example, the light chain variable region of the CD22-targeted antigen-binding domain may comprise a nucleic acid sequence as set forth in any one selected from the group consisting of: SEQ ID NO: 62, SEQ ID NO: 63, SEQ ID NO: 64, and SEQ ID NO: 65; and the heavy chain variable region of the CD22-targeted antigen-binding domain may comprise a nucleic acid sequence as set forth in any one selected from the group consisting of: SEQ ID NO: 66, SEQ ID NO: 67, SEQ ID NO: 68, and SEQ ID NO: 69. For example, the nucleic acid molecule may encode a structure as shown in III-5 in FIG. 1 of the present application. For example, the nucleic acid molecule may comprise a nucleic acid sequence as set forth in SEQ ID NO: 83. For example, the structure shown in III-5 in FIG. 1 may comprise a nucleic acid sequence as set forth in SEQ ID NO: 83.

For example, the first antigen may be CD22, and a CD22-targeted antigen-binding domain may comprise a light chain variable region and a heavy chain variable region; and the second antigen may be CD19, and a CD19-targeted antigen-binding domain may comprise a light chain variable region and a heavy chain variable region. For example, the light chain variable region of the CD22-targeted antigen-binding domain may comprise a nucleic acid sequence as set forth in any one selected from the group consisting of: SEQ ID NO: 62, SEQ ID NO: 63, SEQ ID NO: 64, and SEQ ID NO: 65; and the heavy chain variable region of the CD22-targeted antigen-binding domain may comprise a nucleic acid sequence as set forth in any one selected from the group consisting of: SEQ ID NO: 66, SEQ ID NO: 67, SEQ ID NO: 68, and SEQ ID NO: 69. For example, the light chain variable region of the CD19-targeted antigen-binding domain may comprise a nucleic acid sequence as set forth in any one selected from the group consisting of: SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33; and the heavy chain variable region of the CD19-targeted antigen-binding domain may comprise a nucleic acid sequence as set forth in any one selected from the group consisting of: SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43. For example, the nucleic acid molecule may encode a structure as shown in III-6 in FIG. 1 of the present application. For example, the nucleic acid molecule may comprise a nucleic acid sequence as set forth in SEQ ID NO: 84. For example, the structure shown in III-6 in FIG. 1 may comprise a nucleic acid sequence as set forth in SEQ ID NO: 84.

In the present application, in the nucleic acid molecule, the LoxP sites may be selected from the group consisting of: wild-type LoxP, LoxP2722, LoxP511, LoxP5271 and LoxP3171. For example, the LoxP site may comprise a nucleotide sequence as set forth in any one selected from the group consisting of: SEQ ID NO: 12, SEQ ID NO: 13, SEQ ID NO: 14, SEQ ID NO: 15, and SEQ ID NO: 16.

In the present application, the nucleic acid molecule may comprise a nucleic acid sequence of a promoter. For example, the promoter may be EF1α, CMV, MSCV, and UbC. For example, a sequence of the promoter may comprise a nucleic acid sequence as set forth in any one selected from the group consisting of: SEQ ID NO: 1.

In some embodiments, in the nucleic acid molecule, the leader peptide may comprise a leader peptide moiety derived from a protein selected from the group consisting of: CD8, CD33, and CD45.

In the present application, the nucleic acid molecule may comprise at least one nucleic acid sequence encoding a leader peptide. For example, a sequence of the leader peptide may comprise a nucleotide sequence as set forth in any one selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 78.

In the present application, the nucleic acid molecule may comprise a nucleic acid sequence encoding a non-antigen-binding function domain of a chimeric antigen receptor. For example, the non-antigen binding function domain may comprise a hinge region, a transmembrane region, a co-stimulatory domain, and/or an intracellular signaling domain.

In the present application, in the nucleic acid molecule, the hinge region may comprise a hinge region derived from a protein selected from the group consisting of: CD8, CD28, and 4-1BB. For example, the hinge region may comprise a nucleic acid sequence as set forth in SEQ ID NO: 70. For example, the hinge region may comprise a nucleic acid sequence as set forth in SEQ ID NO: 79.

In the present application, in the nucleic acid molecule, the transmembrane region may comprise a transmembrane region derived from a protein selected from the group consisting of: CD8, CD28 and CD19. For example, the transmembrane region may comprise a nucleic acid sequence as set forth in SEQ ID NO: 71. For example, the transmembrane region may comprise a nucleic acid sequence as set forth in SEQ ID NO: 80.

In the present application, in the nucleic acid molecule, the co-stimulatory domain may comprise a co-stimulatory domain derived from a protein selected from the group consisting of: 4-1BB, OX40, CD2, CD27, CD28, CDS, ICAM-1, LFA-1, and ICOS. For example, the co-stimulatory domain may be derived from 4-1BB. For example, the co-stimulatory domain may comprise a nucleic acid sequence as set forth in SEQ ID NO: 72 or SEQ ID NO: 81.

In the present application, in the nucleic acid molecule, the intracellular signaling domain may comprise an intracellular signaling domain derived from a protein selected from the group consisting of: CD3ζ, FcεRIγ, and ZAP70. For example, the intracellular signaling domain may be derived from CD3ζ. For example, the intracellular signaling domain may comprise a nucleic acid sequence as set forth in SEQ ID NO: 73 or SEQ ID NO: 82.

In the present application, the nucleic acid molecule may comprise a nucleic acid sequence encoding a recognition enzyme specifically recognizing the LoxP sites, wherein the recognition enzyme may be selected from the group consisting of: CRE and Brec1. For example, the nucleic acid sequence encoding the recognition enzyme specifically recognizing the LoxP sites may be derived from CRE, with a sequence as set forth in SEQ ID NO: 74.

In the present application, in the nucleic acid molecule, the cleavable peptide may be selected from the group consisting of: P2A, T2A, F2A, E2A, BmCPV2A, and BmIFV2A. For example, the cleavable peptide may be derived from P2A and T2A, with a sequence that may comprise a nucleic acid sequence as set forth in any one selected from the group consisting of: SEQ ID NO: 17, SEQ ID NO: 18, SEQ ID NO: 19, and SEQ ID NO: 20.

In the present application, the nucleic acid molecule may comprise a nucleic acid sequence encoding a backbone vector. For example, the backbone vector may comprise an HIV packaging vector, with a sequence as set forth in SEQ ID NO: 21.

In the present application, the nucleic acid molecule may comprise a 5'LTR sequence as set forth in SEQ ID NO: 22.

In the present application, the nucleic acid molecule may comprise a 3'LTR sequence as set forth in SEQ ID NO: 22.

In the present application, the nucleic acid molecule may comprise a nucleic acid sequence encoding WPRE, with the sequence as set forth in SEQ ID NO: 23.

In the present application, the nucleic acid molecule may comprise at least one pair of LoxP sites with reverse-complementing sequences.

In the present application, in the nucleic acid molecule, the one pair of LoxP sites with reverse-complementing sequences may comprise therebetween the nucleic acid sequence encoding the first antigen-binding domain and a reverse-complementing sequence of the nucleic acid sequence encoding the second antigen-binding domain; or, the one pair of LoxP sites with reverse-complementing sequences may comprise therebetween a reverse-complementing sequence of the nucleic acid sequence encoding the first antigen-binding domain, and the nucleic acid sequence encoding the second antigen-binding domain.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the LoxP site 1, the reverse-complementing nucleic acid sequence encoding the first antigen-binding domain, the reverse-complementing nucleic acid sequence encoding the leader peptide, the nucleic acid sequence encoding the leader peptide, the nucleic acid sequence encoding the second antigen-binding domain, the reverse-complementing nucleic acid sequence encoding the LoxP site 1, the nucleic acid sequence encoding the non-antigen-binding function domain, the nucleic acid sequence encoding the cleavable peptide, the nucleic acid sequence encoding the recognition enzyme, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, an initiation codon ATG, the nucleic acid sequence encoding the LoxP site 1, the reverse-complementing nucleic acid sequence encoding the first antigen-binding domain, the reverse-complementing nucleic acid sequence encoding the leader peptide, the nucleic acid sequence encoding the cleavable peptide, the nucleic acid sequence encoding the leader peptide, the nucleic acid sequence encoding the second antigen-binding domain, the reverse-complementing nucleic acid sequence encoding the LoxP site 1, the nucleic acid sequence encoding the non-antigen-binding function domain, the nucleic acid sequence encoding the cleavable peptide, the nucleic acid sequence encoding the recognition enzyme, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the recognition enzyme, the nucleic acid sequence encoding the cleavable peptide, the nucleic acid sequence encoding the LoxP site 1, the reverse-complementing nucleic acid sequence encoding the first antigen-binding domain, the reverse-complementing nucleic acid sequence encoding the leader peptide, the nucleic acid sequence encoding the leader peptide, the nucleic acid sequence encoding the second antigen-binding domain, the reverse-complementing nucleic acid sequence encoding the LoxP site 1, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the recognition enzyme, the nucleic acid sequence encoding the cleavable peptide, the nucleic acid sequence encoding the LoxP site 1, the reverse-complementing nucleic acid sequence encoding the first antigen-binding domain, the reverse-complementing nucleic acid sequence encoding the leader peptide, the reverse-complementing nucleic acid sequence encoding the cleavable peptide, the nucleic acid sequence encoding the cleavable peptide, the nucleic acid sequence encoding the second antigen-binding domain, the reverse-complementing nucleic acid sequence encoding the LoxP site 1, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the LoxP site 1, the nucleic acid sequence encoding the leader peptide, the nucleic acid sequence encoding the first antigen-binding domain, the nucleic acid sequence encoding the LoxP site 2, the nucleic acid sequence encoding the non-antigen-binding function domain, the reverse-complementing nucleic acid sequence encoding the LoxP site 2, the reverse-complementing nucleic acid sequence encoding the second antigen-binding domain, the reverse-complementing nucleic acid sequence encoding the leader peptide, the reverse-complementing nucleic acid sequence encoding the LoxP site 1, the nucleic acid sequence encoding the cleavable peptide, the nucleic acid sequence encoding the recognition enzyme, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the recognition enzyme, the nucleic acid sequence encoding the cleavable peptide, the nucleic acid sequence encoding the leader peptide, the nucleic acid sequence encoding the first antigen-binding domain, the nucleic acid sequence encoding the LoxP site 2, the nucleic acid sequence encoding the non-antigen-binding function domain, the reverse-complementing nucleic acid sequence encoding the LoxP site 2, the reverse-complementing nucleic acid sequence encoding the second antigen-binding domain, the reverse-complementing nucleic acid sequence encoding the leader peptide, the nucleic acid sequence encoding the LoxP site 1, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the LoxP site 1, the nucleic acid sequence encoding the leader peptide, the nucleic acid sequence encoding the first antigen-binding domain, the nucleic acid sequence encoding the non-antigen-binding function domain, a termination codon, a termination codon, the reverse-complementing nucleic acid sequence encoding the non-antigen-binding function domain, the reverse-complementing nucleic acid sequence encoding the second antigen-binding domain, the reverse-complementing nucleic acid sequence encoding the leader peptide, the reverse-complementing nucleic acid sequence encoding the LoxP site 1, the nucleic acid sequence encoding the cleavable peptide, the nucleic acid sequence encoding the recognition enzyme, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the recognition enzyme, the nucleic acid sequence encoding the cleavable peptide, the nucleic acid sequence encoding the leader peptide, the nucleic acid sequence encoding the first antigen-binding domain, the nucleic acid sequence encoding the non-antigen-binding function domain, a termination codon, a termination codon, the reverse-complementing nucleic acid sequence encoding the non-antigen-binding function domain, the reverse-complementing nucleic acid sequence encoding the second antigen-binding domain, the reverse-complementing nucleic acid sequence encoding the leader peptide, the reverse-complementing nucleic acid sequence encoding the LoxP site 1, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the leader peptide, the nucleic acid sequence encoding the first antigen-binding domain, the nucleic acid sequence encoding the non-antigen-binding function domain, a PolyA sequence, a PolyA reverse-complementing sequence, the reverse-complementing nucleic acid sequence encoding the non-antigen-binding function domain, the reverse-complementing nucleic acid sequence encoding the second antigen-binding domain, the reverse-complementing nucleic acid sequence encoding the leader peptide, the reverse-complementing nucleic acid sequence of the promoter, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the leader peptide, the nucleic acid sequence encoding the first antigen-binding domain, the nucleic acid sequence encoding the non-antigen-binding function domain, the nucleic acid sequence encoding the cleavable peptide, the nucleic acid sequence encoding the leader peptide, the nucleic acid sequence encoding the second antigen-binding domain, the nucleic acid sequence encoding the non-antigen-binding function domain, the WPRE, and the 3'LTR.

For example, in the nucleic acid molecule, the first antigen may be CD19, and the nucleic acid sequence encoding the first antigen-binding domain may comprise a light chain variable region and a heavy chain variable region. For example, the light chain variable region of the CD19-targeted antigen-binding domain may comprise a nucleic acid sequence as set forth in any one selected from the group consisting of: SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33; and the heavy chain variable region of the CD19-targeted antigen-binding domain may comprise a nucleic acid sequence as set forth in any one selected from the group consisting of: SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43.

For example, in the nucleic acid molecule, the second antigen may be CD22, and the nucleic acid sequence encoding the second antigen-binding domain may comprise a light chain variable region and a heavy chain variable region. For example, the light chain variable region of the CD22-targeted antigen-binding domain may comprise a nucleic acid sequence as set forth in any one selected from the group consisting of: SEQ ID NO: 62, SEQ ID NO: 63, SEQ ID NO: 64, and SEQ ID NO: 65; and the heavy chain variable region of the CD22-targeted antigen-binding domain may comprise a nucleic acid sequence as set forth in any one selected from the group consisting of: SEQ ID NO: 66, SEQ ID NO: 67, SEQ ID NO: 68, and SEQ ID NO: 69.

In the present application, the nucleic acid molecule may comprise a nucleic acid sequence of a promoter. For example, the promoter may be EF1α, CMV, MSCV, and UbC. For example, a sequence of the promoter may comprise a nucleic acid sequence as set forth in SEQ ID NO: 1.

In some embodiments, in the nucleic acid molecule, the leader peptide may comprise a leader peptide moiety derived from a protein selected from the group consisting of: CD8, CD33, and CD45.

In the present application, the nucleic acid molecule may comprise at least one nucleic acid sequence encoding a leader peptide. For example, a sequence of the leader peptide may comprise a nucleotide sequence as set forth in any one selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 78.

In the present application, the nucleic acid molecule may comprise a nucleic acid sequence encoding a non-antigen-binding function domain of a chimeric antigen receptor. For example, the non-antigen binding function domain may comprise a hinge region, a transmembrane region, a co-stimulatory domain, and/or an intracellular signaling domain.

In the present application, in the nucleic acid molecule, the hinge region may comprise a hinge region derived from a protein selected from the group consisting of: CD8, CD28, and 4-1BB. For example, the hinge region may comprise a nucleic acid sequence as set forth in SEQ ID NO: 70 or SEQ ID NO: 79.

In the present application, in the nucleic acid molecule, the transmembrane region may comprise a transmembrane region derived from a protein selected from the group consisting of: CD8, CD28 and CD19. For example, the transmembrane region may comprise a nucleic acid sequence as set forth in SEQ ID NO: 71 or SEQ ID NO: 80.

In the present application, in the nucleic acid molecule, the co-stimulatory domain may comprise a co-stimulatory domain derived from a protein selected from the group consisting of: 4-1BB, OX40, CD2, CD27, CD28, CDS, ICAM-1, LFA-1, and ICOS. For example, the co-stimulatory domain may be derived from 4-1BB, with a nucleic acid sequence as set forth in SEQ ID NO: 72 or SEQ ID NO: 81.

In the present application, in the nucleic acid molecule, the intracellular signaling domain may comprise an intracellular signaling domain derived from a protein selected from the group consisting of: CD3ζ, FccRIγ, and ZAP70. For example, the intracellular signaling domain may be derived from CD3ζ, with a nucleic acid sequence as set forth in SEQ ID NO: 73 or SEQ ID NO: 82.

In the present application, the nucleic acid molecule may comprise a nucleic acid sequence encoding a recognition enzyme specifically recognizing the LoxP sites, wherein the recognition enzyme may be selected from the group consisting of: CRE and Brec1. For example, the nucleic acid sequence encoding the recognition enzyme specifically recognizing the LoxP sites may be derived from CRE, with a sequence as set forth in SEQ ID NO: 74.

In the present application, the nucleic acid molecule may comprise at least one nucleic acid sequence encoding a cleavable peptide, wherein the cleavable peptide may be selected from the group consisting of: P2A, T2A, F2A, E2A, BmCPV2A, and BmIFV2A. For example, the cleavable peptide may be derived from P2A and T2A, with a sequence that may comprise a nucleic acid sequence as set forth in any one selected from the group consisting of: SEQ ID NO: 17, SEQ ID NO: 18, SEQ ID NO: 19, and SEQ ID NO: 20.

In the present application, the nucleic acid molecule may comprise a nucleic acid sequence encoding a backbone vector. For example, the backbone vector may comprise an HIV packaging vector, with a sequence as set forth in SEQ ID NO: 21.

In the present application, the nucleic acid molecule may comprise a 5'LTR sequence as set forth in SEQ ID NO: 22.

In the present application, the nucleic acid molecule may comprise a 3'LTR sequence as set forth in SEQ ID NO: 22.

In the present application, the nucleic acid molecule may comprise a nucleic acid sequence encoding WPRE, with the sequence as set forth in SEQ ID NO: 23.

In the present application, the nucleic acid molecule capable of expressing two types of chimeric antigen receptors may express a CD19-targeted chimeric antigen receptor and a CD22-targeted chimeric antigen receptor.

In the present application, the nucleic acid molecule capable of expressing two types of chimeric antigen receptors may express a GD2-targeted chimeric antigen receptor and a B7H3-targeted chimeric antigen receptor.

In the present application, the nucleic acid molecule capable of expressing two types of chimeric antigen receptors may comprise a nucleic acid sequence as set forth in any one of SEQ ID NOs: 75, 76, 83, and 84.

In the present application, the nucleic acid molecule may express three types of chimeric antigen receptors.

In the present application, the nucleic acid molecule may comprise four different pairs of LoxP sites.

In the present application, in the nucleic acid molecule, the first pair of the LoxP sites may comprise therebetween the nucleic acid sequence encoding the first antigen-binding domain and the nucleic acid sequence encoding the second antigen-binding domain.

In the present application, in the nucleic acid molecule, the second pair of the LoxP sites may comprise therebetween the nucleic acid sequence encoding the first antigen-binding domain.

In the present application, in the nucleic acid molecule, the third pair of the LoxP sites may comprise therebetween the nucleic acid sequence encoding the second antigen-binding domain and a nucleic acid sequence encoding a third antigen-binding domain.

In the present application, in the nucleic acid molecule, the fourth pair of the LoxP sites may comprise therebetween the nucleic acid sequence encoding the first antigen-binding domain.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the leader peptide, the nucleic acid sequence encoding the LoxP site 1, the nucleic acid sequence encoding the LoxP site 3, the nucleic acid sequence encoding the first antigen-binding domain, the nucleic acid sequence encoding the LoxP site 2, the nucleic acid sequence encoding the cleavable peptide, the nucleic acid sequence encoding the recognition enzyme, the nucleic acid sequence encoding the cleavable peptide, the nucleic acid sequence encoding the LoxP site 3, the nucleic acid sequence encoding the second antigen-binding domain, the nucleic acid sequence encoding the LoxP site 4, the nucleic acid sequence encoding the LoxP site 1, the nucleic acid sequence encoding the third antigen-binding domain, the nucleic acid sequence encoding the LoxP site 2, the nucleic acid sequence encoding the LoxP site 4, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the LoxP site 3, the nucleic acid sequence encoding the LoxP site 3, the nucleic acid sequence encoding the leader peptide, the nucleic acid sequence encoding the first antigen-binding domain, the nucleic acid sequence encoding the LoxP site 2, the nucleic acid sequence encoding the cleavable peptide, the nucleic acid sequence encoding the recognition enzyme, the nucleic acid sequence encoding the cleavable peptide, the nucleic acid sequence encoding the LoxP site 3, the nucleic acid sequence encoding the leader peptide, the nucleic acid sequence encoding the second antigen-binding domain, the nucleic acid sequence encoding the LoxP site 4, the nucleic acid sequence encoding the LoxP site 1, the nucleic acid sequence encoding the leader peptide, the nucleic acid sequence encoding the third antigen-binding domain, the nucleic acid sequence encoding the LoxP site 2, the nucleic acid sequence encoding the LoxP site 4, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the leader peptide, the nucleic acid sequence encoding the LoxP site 1, the nucleic acid sequence encoding the LoxP site 3, the nucleic acid sequence encoding the first antigen-binding domain, the nucleic acid sequence encoding the LoxP site 2, the nucleic acid sequence encoding the LoxP site 3, the nucleic acid sequence encoding the second antigen-binding domain, the nucleic acid sequence encoding the LoxP site 4, the nucleic acid sequence encoding the LoxP site 1, the nucleic acid sequence encoding the third antigen-binding domain, the nucleic acid sequence encoding the LoxP site 2, the nucleic acid sequence encoding the LoxP site 4, the nucleic acid sequence encoding the non-antigen-binding function domain, the nucleic acid sequence encoding the cleavable peptide, the nucleic acid sequence encoding the recognition enzyme, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the LoxP site 3, the nucleic acid sequence encoding the LoxP site 3, the nucleic acid sequence encoding the leader peptide, the nucleic acid sequence encoding the first antigen-binding domain, the nucleic acid sequence encoding the LoxP site 2, the nucleic acid sequence encoding the LoxP site 3, the nucleic acid sequence encoding the leader peptide, the nucleic acid sequence encoding the second antigen-binding domain, the nucleic acid sequence encoding the LoxP site 4, the nucleic acid sequence encoding the LoxP site 1, the nucleic acid sequence encoding the leader peptide, the nucleic acid sequence encoding the third antigen-binding domain, the nucleic acid sequence encoding the LoxP site 2, the nucleic acid sequence encoding the LoxP site 4, the nucleic acid sequence encoding the non-antigen-binding function domain, the nucleic acid sequence encoding the cleavable peptide, the nucleic acid sequence encoding the recognition enzyme, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the recognition enzyme, the nucleic acid sequence encoding the cleavable peptide, the nucleic acid sequence encoding the leader peptide, the nucleic acid sequence encoding the LoxP site 1, the nucleic acid sequence encoding the LoxP site 3, the nucleic acid sequence encoding the first antigen-binding domain, the nucleic acid sequence encoding the LoxP site 2, the nucleic acid sequence encoding the LoxP site 3, the nucleic acid sequence encoding the second antigen-binding domain, the nucleic acid sequence encoding the LoxP site 4, the nucleic acid sequence encoding the LoxP site 1, the nucleic acid sequence encoding the third antigen-binding domain, the nucleic acid sequence encoding the LoxP site 2, the nucleic acid sequence encoding the LoxP site 4, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the recognition enzyme, the nucleic acid sequence encoding the cleavable peptide, the nucleic acid sequence encoding the LoxP site 3, the nucleic acid sequence encoding the LoxP site 3, the nucleic acid sequence encoding the leader peptide, the nucleic acid sequence encoding the first antigen-binding domain, the nucleic acid sequence encoding the LoxP site 2, the nucleic acid sequence encoding the LoxP site 3, the nucleic acid sequence encoding the leader peptide, the nucleic acid sequence encoding the second antigen-binding domain, the nucleic acid sequence encoding the LoxP site 4, the nucleic acid sequence encoding the LoxP site 1, the nucleic acid sequence encoding the leader peptide, the nucleic acid sequence encoding the third antigen-binding domain, the nucleic acid sequence encoding the LoxP site 2, the nucleic acid sequence encoding the LoxP site 4, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the leader peptide, the nucleic acid sequence encoding the LoxP site 1, the nucleic acid sequence encoding the LoxP site 3, the nucleic acid sequence encoding the first antigen-binding domain, the nucleic acid sequence encoding the LoxP site 2, the nucleic acid sequence encoding the LoxP site 3, the nucleic acid sequence encoding the second antigen-binding domain, the nucleic acid sequence encoding the LoxP site 4, the nucleic acid sequence encoding the LoxP site 1, the nucleic acid sequence encoding the third antigen-binding domain, the nucleic acid sequence encoding the LoxP site 2, the nucleic acid sequence encoding the LoxP site 4, the nucleic acid sequence encoding the non-antigen-binding function domain, the WPRE, and the 3'LTR.

In the present application, the nucleic acid molecule may comprise, from the 5'-terminal to the 3'-terminal, the 5' LTR, the HIV packaging vector, the nucleic acid sequence encoding the promoter, the nucleic acid sequence encoding the LoxP site 3, the nucleic acid sequence encoding the LoxP site 3, the nucleic acid sequence encoding the leader peptide, the nucleic acid sequence encoding the first antigen-binding domain, the nucleic acid sequence encoding the LoxP site 2, the nucleic acid sequence encoding the LoxP site 3, the nucleic acid sequence encoding the leader peptide, the nucleic acid sequence encoding the second antigen-binding domain, the nucleic acid sequence encoding the LoxP site 4, the nucleic acid sequence encoding the LoxP site 1, the nucleic acid sequence encoding the leader peptide, the nucleic acid sequence encoding the third antigen-binding domain, the nucleic acid sequence encoding the LoxP site 2, the nucleic acid sequence encoding the LoxP site 4, the nucleic acid sequence encoding the non-antigen-binding function domain, the WPRE, and the 3'LTR. In the present application, the nucleic acid molecule may contact the corresponding LoxP site recognition enzyme, the sequence between each pair of the LoxP sites may be removed respectively to form an expression molecule comprising only one nucleic acid molecule encoding the antigen-binding domain, and the expression molecule may express a chimeric antigen receptor. For example, the corresponding LoxP site recognition enzyme may respectively contact and recognize the nucleic acid sequences encoding the LoxP sites 1, the nucleic acid sequences encoding the LoxP sites 2, and the nucleic acid sequences encoding the LoxP sites 3, and the sequences between the two LoxP sites 1, the two LoxP sites 2, and the two LoxP sites 3 can be respectively removed, such that the nucleic acid molecule is reconstituted into an expression molecule capable of expressing three single and complete chimeric antigen receptor structures carrying the first antigen-binding domain, the second antigen-binding domain, and the third antigen-binding domain, respectively.

For example, in the nucleic acid molecule, the first antigen may be CD22, and the nucleic acid sequence encoding the second antigen-binding domain may comprise a light chain variable region and a heavy chain variable region. For example, the light chain variable region of the CD22-targeted antigen-binding domain may comprise a nucleic acid sequence as set forth in any one selected from the group consisting of: SEQ ID NO: 62, SEQ ID NO: 63, SEQ ID NO: 64, and SEQ ID NO: 65; and the heavy chain variable region of the CD22-targeted antigen-binding domain may comprise a nucleic acid sequence as set forth in any one selected from the group consisting of: SEQ ID NO: 66, SEQ ID NO: 67, SEQ ID NO: 68, and SEQ ID NO: 69.

For example, in the nucleic acid molecule, the second antigen may be CD20, and the nucleic acid sequence encoding the second antigen-binding domain may comprise a light chain variable region and a heavy chain variable region. The light chain variable region of the CD20-targeted antigen-binding domain may comprise a nucleic acid sequence as set forth in any one selected from the group consisting of: SEQ ID NO: 56, SEQ ID NO: 57, and SEQ ID NO: 58; and the heavy chain variable region of the CD20-targeted antigen-binding domain may comprise a nucleic acid sequence as set forth in any one selected from the group consisting of: SEQ ID NO: 59, SEQ ID NO: 60, and SEQ ID NO: 61.

For example, in the nucleic acid molecule, the third antigen may be CD19, and the nucleic acid sequence encoding the first antigen-binding domain may comprise a light chain variable region and a heavy chain variable region. For example, the light chain variable region of the CD19-targeted antigen-binding domain may comprise a nucleic acid sequence as set forth in any one selected from the group consisting of: SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33; and the heavy chain variable region of the CD19-targeted antigen-binding domain may comprise a nucleic acid sequence as set forth in any one selected from the group consisting of: SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43.

In the present application, the nucleic acid molecule may comprise a nucleic acid sequence of a promoter. For example, the promoter may be EF1α, CMV, MSCV, and UbC. For example, a sequence of the promoter may comprise a nucleic acid sequence as set forth in SEQ ID NO: 1.

In the present application, the nucleic acid molecule may comprise at least one nucleic acid sequence encoding a leader peptide. For example, a sequence of the leader peptide may comprise a nucleotide sequence as set forth in any one selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 78.

In some embodiments, in the nucleic acid molecule, the leader peptide may comprise a leader peptide moiety derived from a protein selected from the group consisting of: CD8, CD33, and CD45.

In the present application, the nucleic acid molecule may comprise a nucleic acid sequence encoding a non-antigen-binding function domain of a chimeric antigen receptor. For example, the non-antigen binding function domain may comprise a hinge region, a transmembrane region, a co-stimulatory domain, and/or an intracellular signaling domain.

In the present application, in the nucleic acid molecule, the hinge region may comprise a hinge region derived from a protein selected from the group consisting of: CD8, CD28, and 4-1BB. For example, the hinge region may comprise a nucleic acid sequence as set forth in SEQ ID NO: 70 or SEQ ID NO: 79.

In the present application, in the nucleic acid molecule, the transmembrane region may comprise a transmembrane region derived from a protein selected from the group consisting of: CD8, CD28, and CD19. For example, the transmembrane region may comprise a nucleic acid sequence as set forth in SEQ ID NO: 71 or SEQ ID NO: 80.

In the present application, in the nucleic acid molecule, the co-stimulatory domain may comprise a co-stimulatory domain derived from a protein selected from the group consisting of: 4-1BB, OX40, CD2, CD27, CD28, CDS, ICAM-1, LFA-1, and ICOS. For example, the co-stimulatory domain may be derived from 4-1BB, with a nucleic acid sequence as set forth in SEQ ID NO: 72 or SEQ ID NO: 81.

In the present application, in the nucleic acid molecule, the intracellular signaling domain may comprise an intracellular signaling domain derived from a protein selected from the group consisting of: CD3ζ, FcεRIγ, and ZAP70. For example, the intracellular signaling domain may be derived from CD3ζ, with a nucleic acid sequence as set forth in SEQ ID NO: 73 or SEQ ID NO: 82.

In the present application, the nucleic acid molecule may comprise a nucleic acid sequence encoding a recognition enzyme specifically recognizing the LoxP sites, wherein the recognition enzyme may be selected from the group consisting of: CRE and Brec1. For example, the nucleic acid sequence encoding the recognition enzyme specifically recognizing the LoxP sites may be derived from CRE, with a sequence as set forth in SEQ ID NO: 74.

In the present application, the nucleic acid molecule may comprise at least one nucleic acid sequence encoding a cleavable peptide, wherein the cleavable peptide may be selected from the group consisting of: P2A, T2A, F2A, E2A, BmCPV2A, and BmIFV2A. For example, the cleavable peptide may be derived from P2A and T2A, with a sequence that may comprise a nucleic acid sequence as set forth in any one selected from the group consisting of: SEQ ID NO: 17, SEQ ID NO: 18, SEQ ID NO: 19, and SEQ ID NO: 20.

In the present application, the nucleic acid molecule may comprise a nucleic acid sequence encoding a backbone vector. For example, the backbone vector may comprise an HIV packaging vector, with a sequence as set forth in SEQ ID NO: 21.

In the present application, the nucleic acid molecule may comprise a 5'LTR sequence as set forth in SEQ ID NO: 22.

In the present application, the nucleic acid molecule may comprise a 3'LTR sequence as set forth in SEQ ID NO: 22.

In the present application, the nucleic acid molecule may comprise a nucleic acid sequence encoding WPRE, with the sequence as set forth in SEQ ID NO: 23.

In the present application, the nucleic acid molecule capable of expressing three types of chimeric antigen receptors may express the CD19-targeted chimeric antigen receptor, the CD22-targeted chimeric antigen receptor, and the CD20-targeted chimeric antigen receptor.

In the present application, the nucleic acid molecule capable of expressing three types of chimeric antigen receptors may comprise a nucleic acid sequence as set forth in SEQ ID NO: 77.

Plasmid, Host Cell and Preparation Methods

In another aspect, the present application provides a plasmid or plasmids, which may comprise the nucleic acid molecule or nucleic acid molecules of the present application. Each plasmid may comprise the nucleic acid molecule or nucleic acid molecules. In addition, the plasmid may further comprise other genes, for example, a marker gene allowing selection of this vector in a suitable host cell and under a suitable condition. In addition, the plasmid may further comprise an expression control element allowing correct expression of a coding region in a suitable host. Such a control element is well known to those skilled in the art, which, for example, may comprise a ribosome binding site, an enhancer, and other control elements that regulate gene transcription or mRNA translation. For example, the plasmid may be a viral plasmid.

In another aspect, the present application provides a host cell, which may comprise the nucleic acid molecule or nucleic acid molecules of the present application and/or the plasmid or plasmids of the present application. In the present application, each type of or each host cell may comprise one or one type of the nucleic acid molecule or plasmid of the present application. In the present application, each type of or each cell may comprise a plurality of (for example, two or more) or a plurality of types of (for example, two or more types of) plasmids of the present application. For example, the plasmid of the present application may be introduced into the host cell, for example, a T cell, an NK cell, or other immune cells or the like. The vector of the present application may be introduced into the host cell by methods known in the art, for example, electroporation, lipofectine transfection, lipofectamin transfection or the like. In the present application, the cell may express at least two different types of chimeric antigen receptors.

In another aspect, the present application provides a method for preparing a chimeric antigen receptor. The method may comprise the following steps:

(1) providing a nucleic acid molecule comprising a nucleic acid sequence encoding a first antigen-binding domain, a nucleic acid sequence encoding a second antigen-binding domain, and at least one pair of LoxP sites, with each pair of the LoxP sites recognizable by a corresponding LoxP site recognition enzyme, wherein the first antigen-binding domain and the second antigen-binding domain different from the first antigen-binding domain are involved in the composition of a first chimeric antigen receptor and a second chimeric antigen receptor, respectively, and wherein at least one pair of the LoxP sites comprises therebetween at least one nucleic acid sequence encoding the antigen-binding domain;

(2) contacting the nucleic acid molecule with the corresponding LoxP site recognition enzyme; and (3) removing the sequence between each pair of the LoxP sites respectively to form an expression molecule comprising only one nucleic acid molecule encoding the antigen-binding domain, wherein the expression molecule can express a chimeric antigen receptor.

In the present application, in the method, the contacting may comprise adding the corresponding LoxP site recognition enzyme.

In the present application, in the method, the contacting may comprise expressing the nucleic acid molecule encoding the corresponding LoxP site recognition enzyme.

In the present applications, in the method, the nucleic acid molecule encoding the recognition enzyme may be located on a vector.

In the present application, the nucleic acid molecule encoding the recognition enzyme may be located on a different vector than the nucleic acid molecule in step (1).

In the present application, in the method, the nucleic acid molecule in step (1) may comprise the nucleic acid molecule encoding the recognition enzyme.

In the present application, the method may comprise a nucleotide sequence as set forth in any one of SEQ ID NOs. 75-77 and 83-84.

Not wishing to be bound by any particular theory, the following examples are merely to illustrate the nucleic acid molecule, preparation method and uses and the like according to the present application, and are not intended to limit the scope of the present invention.

EXAMPLES

Example 1 Construction of Chimeric Antigen Receptor-Genetically Engineered Vector 1. First, a RRE sequence was inserted between restriction endonuclease sites NotI and HindIII of an expression vector, a cPPT sequence was inserted between an EF1α promoter and CD8a; WPRE was inserted between CD3ζ and LoxP; and a protein tag was added to a 5'-terminal of each scFv fragment.

2. In addition to the general components of the expression vector, the chimeric antigen receptor-genetically engineered vector taking CD19 and CD22 as targets was composed of the following main elements:

I-1: a leader peptide sequence CD8a, a LoxP site 1, a CD19-scFv sequence, a LoxP site 2, a P2A sequence, a CRE protein sequence, a T2A sequence, a LoxP site 1, a CD22-scFv sequence, a LoxP site 2, a hinge region, a transmembrane region, a co-stimulatory molecule 4-1BB, and an effector molecule CD3ζ. The complete sequence formed by the elements was as set forth in SEQ ID NO: 70.

The leader peptide sequence CD8a (as set forth in SEQ ID NO: 11), the LoxP site 1 (as set forth in SEQ ID NO: 13), the CD19-scFv sequence (VL in scFv as set forth in SEQ ID NO: 30 and VH in scFv as set forth in SEQ ID NO: 40), the LoxP site 2 (as set forth in SEQ ID NO: 14), the P2A sequence (as set forth in SEQ ID NO: 17), the CRE protein sequence (as set forth in SEQ ID NO: 74), the T2A sequence (as set forth in SEQ ID NO: 18), the CD22-scFv sequence (VL in scFv as set forth in SEQ ID NO: 65 and VH in scFv as set forth in SEQ ID NO: 69), the hinge region (as set forth in SEQ ID NO: 70), the transmembrane region (as set forth in SEQ ID NO: 71), the co-stimulatory molecule 4-1BB (as set forth in SEQ ID NO: 72), the effector molecule CD3ζ (as set forth in SEQ ID NO: 73) were obtained by a gene synthesis method.

In addition to the general components of the expression vector, the chimeric antigen receptor-genetically engineered vector taking GD2 and B7H3 as targets was composed of the following main components: in short, the CD19-scFv and/or CD22-scFv sequence(s) in I-1 was substituted with GD2-scFv sequence (VL in scFv as set forth in SEQ ID NO: 48 and VH in scFv as set forth in SEQ ID NO: 53) and/or B7H3-scFv sequence (VL in scFv as set forth in SEQ ID NO: 47 and VH in scFv as set forth in SEQ ID NO: 52).

In addition to the general components of the expression vector, the chimeric antigen receptor-genetically engineered vector taking CD19, CD22 and CD20 as targets was composed of the following main sequences:

II-1: a leader peptide sequence CD8a, a LoxP site 1, a LoxP site 3, a CD22-scFv sequence, a LoxP site 2, a P2A sequence, a CRE protein sequence, a T2A sequence, a LoxP site 3, a CD20-scFv sequence, a LoxP site 4, a LoxP site 1, CD19-scFv, a LoxP site 2, a LoxP site 4, a hinge region, a transmembrane region, a co-stimulatory molecule 4-1BB, an effector molecule CD3ζ. The complete sequence formed by the elements was as set forth in SEQ ID NO: 72.

The leader peptide sequence CD8a (as set forth in SEQ ID NO: 11), the LoxP site 1 (as set forth in SEQ ID NO: 13), the LoxP site 3 (as set forth in SEQ ID NO: 15), the CD22-scFv sequence (VL in scFv as set forth in SEQ ID NO: 65 and VH in scFv as set forth in SEQ ID NO: 69), the LoxP site 2 (as set forth in SEQ ID NO: 14), the P2A sequence (as set forth in SEQ ID NO: 17), the CRE protein sequence (as set forth in SEQ ID NO: 74), the T2A sequence (as set forth in SEQ ID NO: 18), the CD20-scFv sequence (as set forth in SEQ ID NOs: 56-61), the LoxP site 4 (as set forth in SEQ ID NO: 16), CD19-scFv (VL in scFv as set forth in SEQ ID NO: 30 and VH in scFv as set forth in SEQ ID NO: 40), the hinge region (as set forth in SEQ ID NO: 70), the transmembrane region (as set forth in SEQ ID NO: 71), the co-stimulatory molecule 4-1BB (as set forth in SEQ ID NO: 72), and the effector molecule CD3ζ (as set forth in SEQ ID NO: 73) were obtained by a gene synthesis method.

3. By designing suitable digestion sites, double enzyme digestion was performed on I-1, II-1, and the expression vector respectively by using the selected restriction endonucleases BamH1 and Spe1; the digested I-1 was linked to the expression vector; the digested II-1 was linked to the expression vector; the linked products were used to transform DH5a competent *Escherichia coli*; and positive clones were inoculated and then held overnight.

4. The plasmids were extracted from bacteria.

Figure 5:
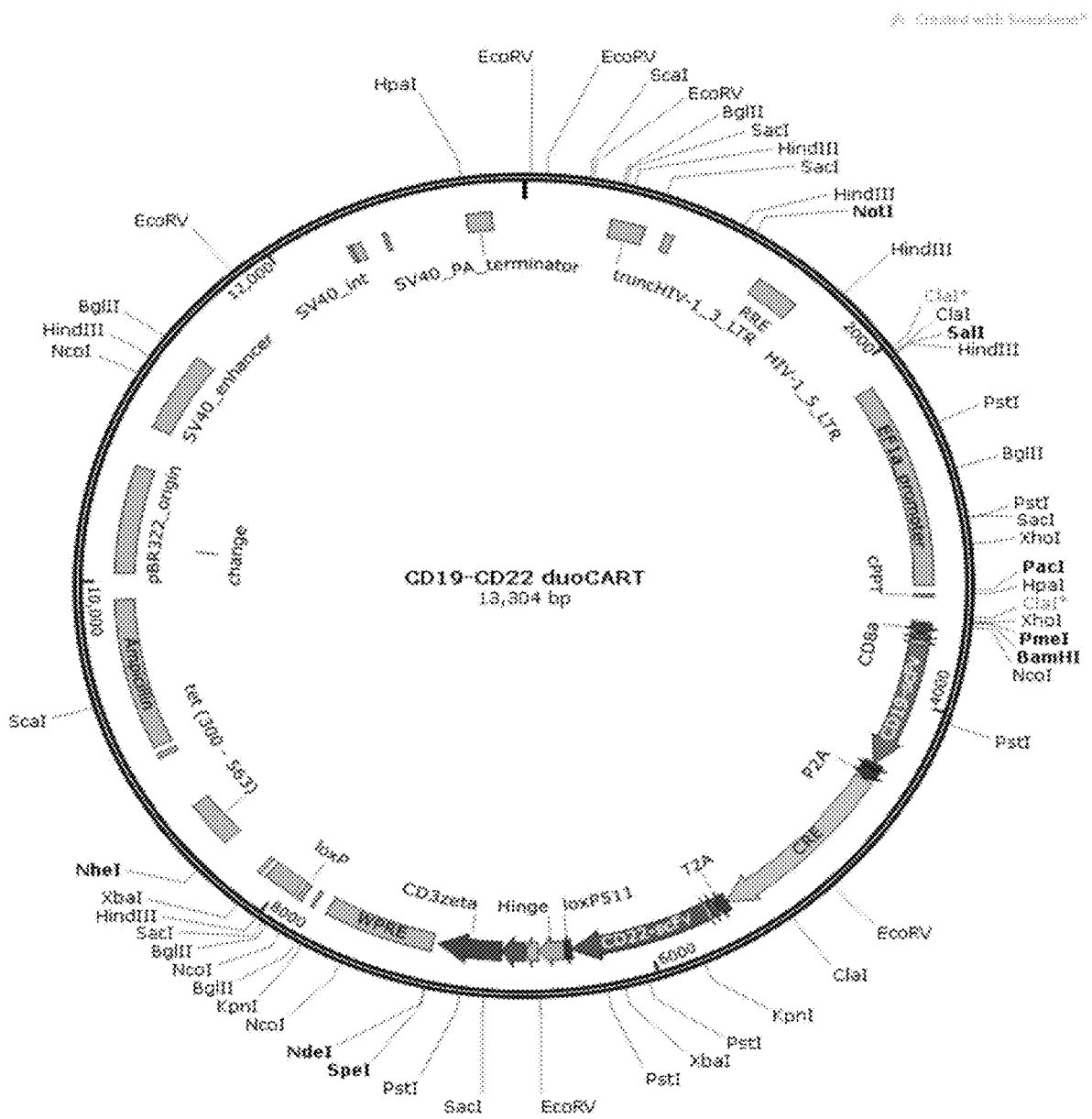
FIG. 5 shows a schematic diagram of a CD19/CD22 dual-targeting vector according to the present application.
Figure 6:
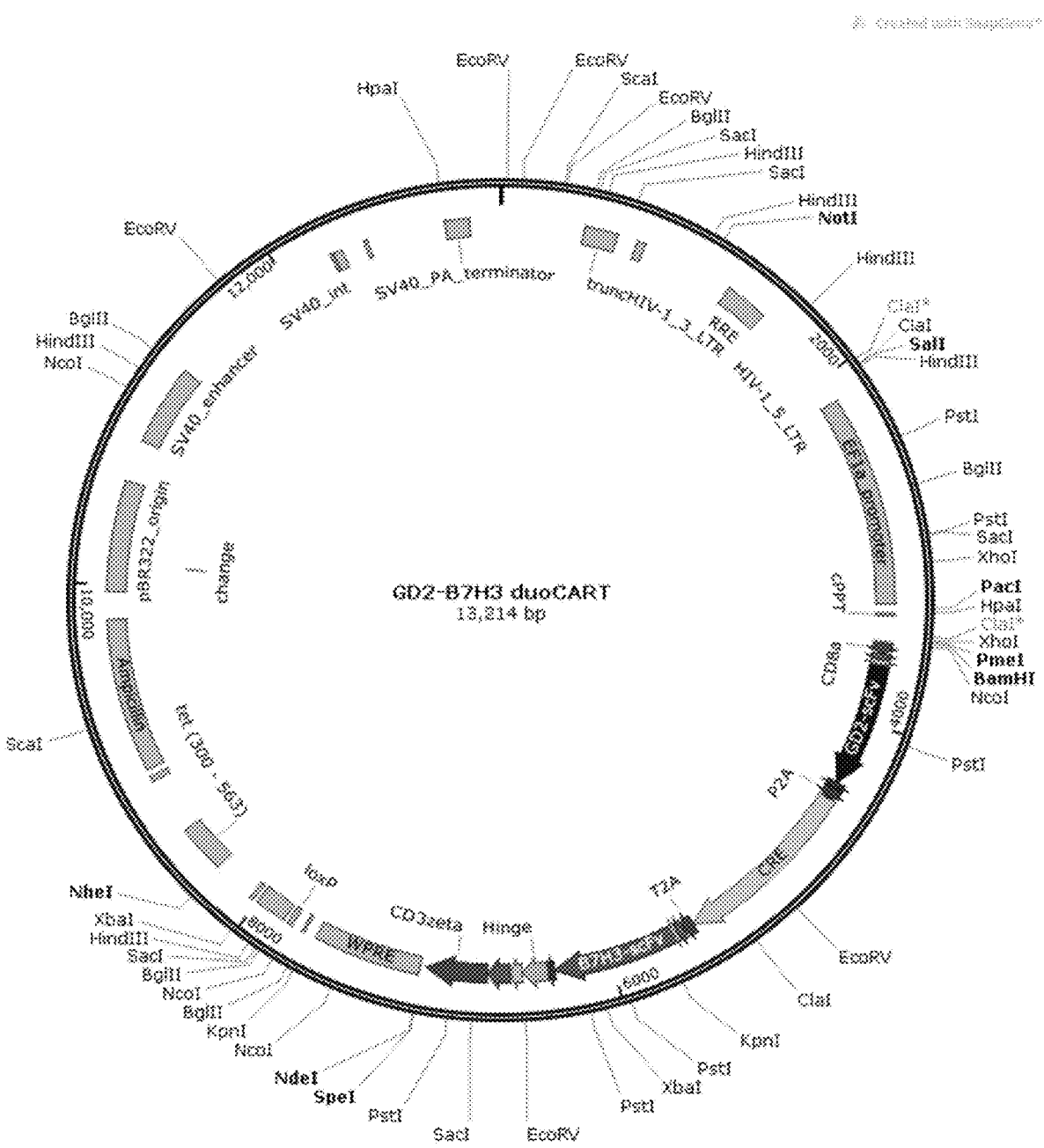
FIG. 6 shows a GD2/B7H3 dual-targeting vector accord-ing to the present application.
Figure 7:
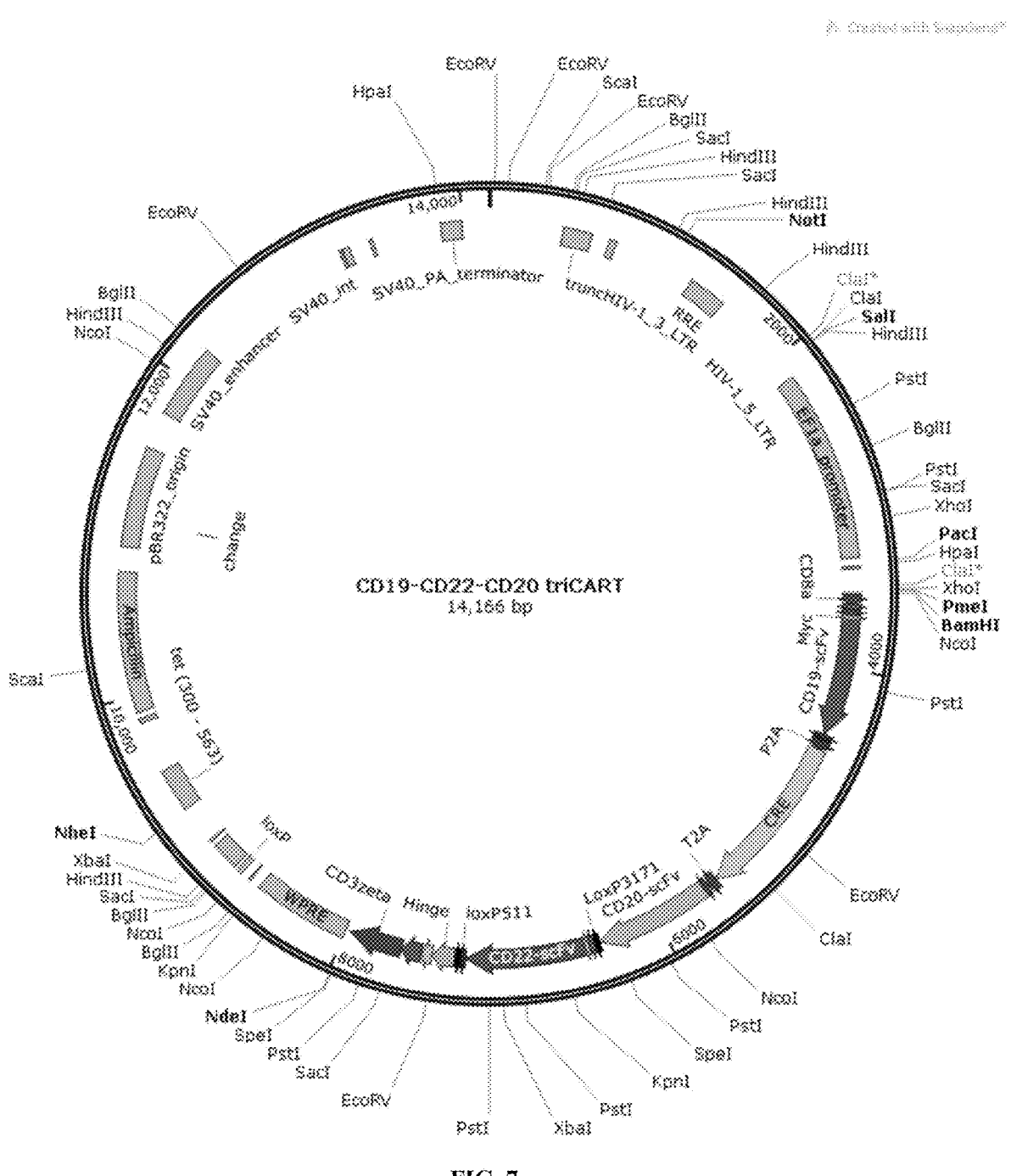
FIG. 7 shows a structural diagram of a CD19/CD22/CD20 triple-targeting vector according to the present application.

Digestion identification and sequencing were carried out. Finally, the expression vector and the I-1 were digested and linked to obtain a chimeric antigen receptor-genetically engineered vector CD19-CD22 duoCART New19CRE22-CAR v3 (as shown in FIG. 5) (corresponding to the nucleic acid sequence of SEQ ID NO: 75), the expression vector was digested and linked to obtain a chimeric antigen receptor-genetically engineered vector GD2-B7H3 duoCART (as set forth in FIG. 6), and the expression vector and II-1 were digested and linked to obtain a chimeric antigen receptor-genetically engineered vector CD19-CD22-CD20 triCART (as set forth in FIG. 7). The 111-5 structure corresponds to the chimeric antigen receptor-genetically engineered vectorCD19-CD22 duoCART (III-5) (as set forth in FIG. 8A) (corresponding to the nucleic acid sequence of SEQ ID NO: 83); the 111-6 structure corresponds to a chimeric antigen receptor-genetically engineered vector CD22-CD19 duoCART (III-6) (as set forth in FIG. 8B) (corresponding to the nucleic acid sequence of SEQ ID NO: 84).

Example 2 Preparation of Virus with Chimeric Antigen Receptor-Genetically Engineered Vector 1. The chimeric antigen receptor-genetically engineered vectors CD19-CD22 duoCART New19CRE22-CAR v3, GD2-B7H3 duoCART and CD19-CD22-CD20 triCART and viral packaging plasmids were transfected at a molar ratio of 1:1:1, with a total mass of 6 ug/10 cm Dish; and 293T cells were transfected with lentiviruses for 72 h and 96 h, cultural supernatant was then collected, and the viruses were concentrated.

2. By the real-time quantitative PCR method, $1\times10^6$ 293 T cells were transfected at the concentration gradient of 1 ul:2 ul:4 ul:8 ul:16 ul:32 ul of the lentiviruses for determination of virus titration, and finally, viruses with the chimeric antigen receptor-genetically engineered vectors CD19-CD22 duoCART New19CRE22-CAR v3, GD2-B7H3 duoCART, and CD19-CD22-CD20 triCART were obtained, respectively. The MOI values of the viruses were: 1) CD19-CD22 duoCART New19CRE22-CAR v3: 2-3; 2) GD2-B7H3 duoCART: 2-3; and 3) CD19-CD22-CD20 triCART: 5-10, respectively.

Example 3 Virus Transfection of Immune Cells

1. Human peripheral blood T lymphocytes were collected, and transfected with the above viruses. Then, the transfection efficiency was measured by flow cytometry using fluorescently labeled antibodies. The fluorescently labeled antibody used for CD19-CART was APC, the fluorescently labeled antibody used for CD22-CART was FITC, and the fluorescently labeled antibody used for CD20-CART was PE.

Figure 8:
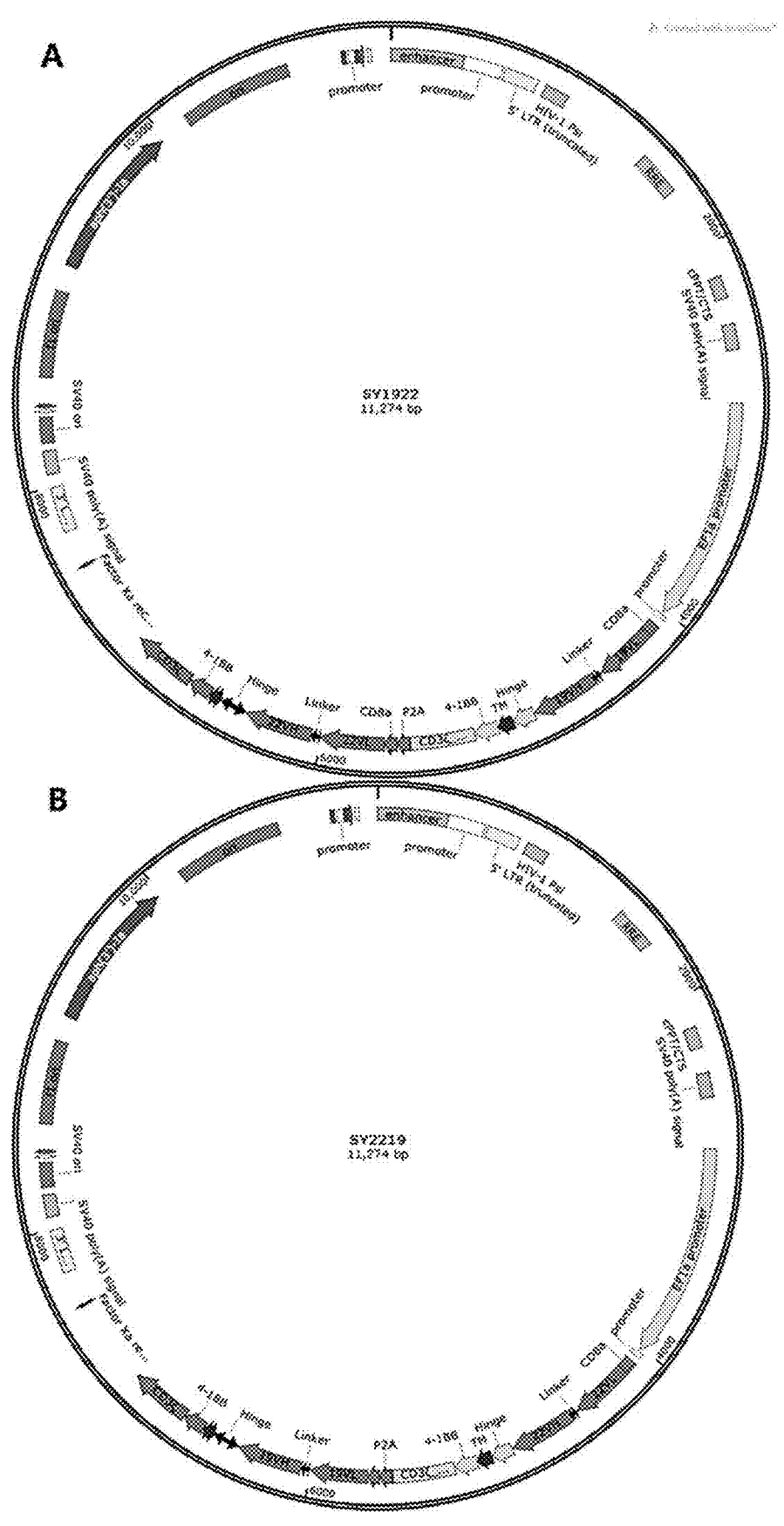
FIG. 8A shows a schematic diagram of the construction of the CD19/CD22 dual-targeting vector according to the pres-ent application.
FIG. 8B shows a schematic diagram of the construction of the CD22/CD19 dual-targeting vector according to the present application.
Figure 9G:
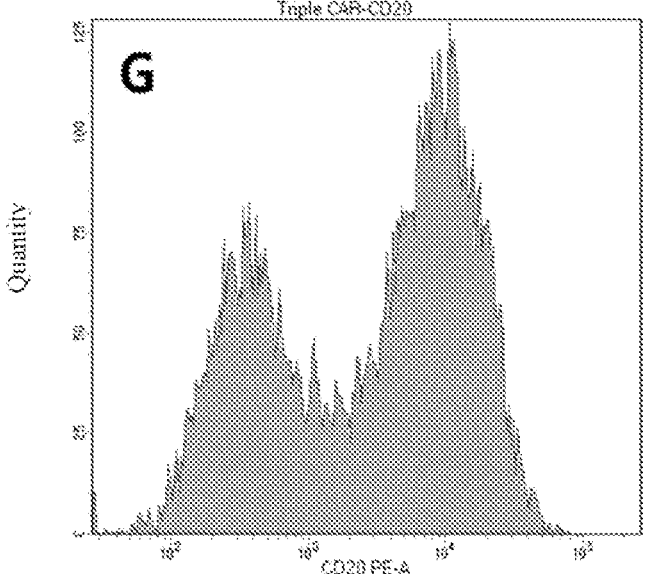

2. The virus prepared by the chimeric antigen receptor-genetically engineered vector was generally transfected at a transfection efficiency of more than 20%, mostly between 40% and 70%, after in vitro transfection, as shown in FIG. 8. In FIG. 8, human T lymphocytes were transfected with single-target and dual-target lentiviral vector-packaged viruses. In FIG. 8, A shows the transfection efficiency of single-target CD19-CART; B shows the transfection efficiency of single-target CD22-CART; C shows the transfection efficiency of CD19-CART in the two-target CD19/CD22-CART; D shows the transfection efficiency of CD22-CART in the dual-target CD19/CD22-CART; E shows the transfection efficiency of CD19-CART in the triple-target CD19/CD22/CD20-CART vector; F shows the transfection efficiency of CD22-CART in the triple-target CD19/CD22/CD20-CART vector; and G shows the transfection efficiency of CD20-CART in the triple-target CD19/CD22/CD20-CART vector. As can be seen from the figures, the dual-target and triple-target derived viruses show no significant difference in transfection efficiency as compared to the single-target virus.

3. After transfection, the resulting CART cells were Single-CD19-CART, Single-CD22-CART, dual-CD19-CD22-CART (corresponding to CD19-CD22 duoCART New19CRE22-CAR v3) and tri-CD19-CD22-CD20-CART, respectively.

Example 4 Detection of Killing Effect of CART Cells on Target Cells

1. At the ratio of 1:5 of Single-CD19-CART to CD19, CD22 and/or CD20-positive leukemia cell lines, the ratio of 1:5 of Single-CD22-CART to CD19, CD22 and/or CD20-positive leukemia cell lines, and the ratio of 1:5 of dual-CD19-CD22-CART cells to CD19, CD22 and/or CD20-positive leukemia cell lines, the three CART cells were mixed with CD19, CD22 and/or CD20-positive leukemia cell lines respectively and co-incubated as test groups; and at the same time, virus-transfected T lymphocytes obtained by preparing vector packages with irrelevant sequences were taken as a control group.

Figure 10:
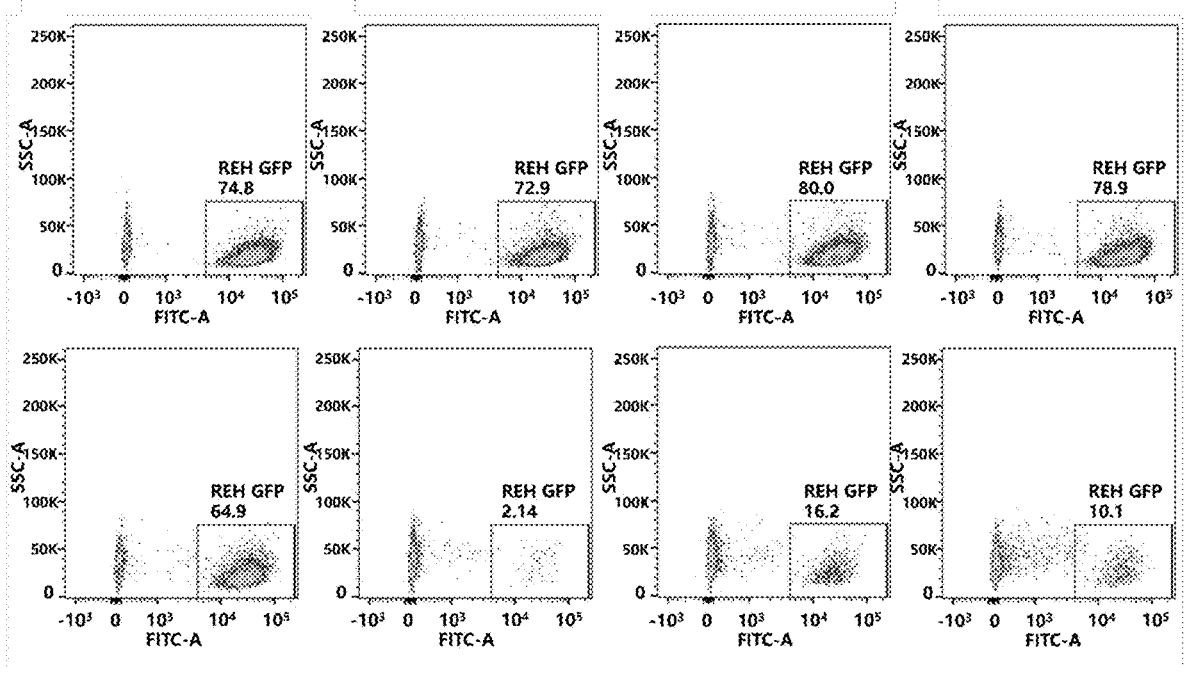
FIG. 10 shows an in vitro cell killing assay of CD19 and CD22 dual-targeting specific CART cells according to the present application.

2. After 0 h, 24 h and 48 h of incubation, in vitro killing assays were carried out by flow cytometry; the killing effects of Single-CD19-CART, Single-CD22-CART, and dual-CD19-CD22-CART cells on leukemia cells-REH were compared at different incubation times; and these cells were compared with the virus-transfected T lymphocytes obtained by preparing vector packages with irrelevant sequences. The results of the killing effects of the three groups of cells on leukemia cells-REH are shown in FIG. 10. The first row shows the maps of Single-CD19-CART, Single-CD22-CART, and dual-CD19-CD22-CART cells co-incubated with leukemia cells-REH for 0 hour. It can be seen that the proportion of leukemia cells in the co-incubation system was 74.8% (control group), 72.9% (Single-CD19-CART group), 80.0% (Single-CD22-CART group), and 78.9% (dual-CD19-CD22-CART group), respectively. The second row shows the maps of Single-CD19-CART, Single-CD22-CART, and dual-CD19-CD22-CART cells co-incubated with leukemia cells-REH for 24 hours. It can be seen that the proportion of leukemia cells in the co-incubation system was 64.9% (control group), 2.14% (Single-CD19-CART group), 16.2% (Single-CD22-CART group), and 10.1% (dual-CD19-CD22-CART group), respectively. It can be seen that, compared with the control group, the dual-CD19-CD22-CART cells show a greatly enhanced killing effect on target cells after 24 h of co-incubation.

Example 5 Acquisition and Proliferation of CART Cells

1. Human peripheral blood was collected at 0.5-2 ml/kg, and subjected to magnetic bead sorting to obtain CD3ζ-positive T lymphocytes or CD56-positive NK cells.

2. CD3ζ/CD28 immunomagnetic beads were added for stimulatory activation and viral transfection, and CD3ζ/CD28 immunomagnetic beads, interleukin-7 and interleukin-15 were continuously given for in vitro proliferation. The cells could be proliferated more than 100 times in 7-8 days.

3. By adjustment based on an in vivo load, the quantities of the dual-CD19-CD22-CART, tri-CD19-CD22-CD20-CART and dual-GD2-B7H3-CART cells reached $2\times10^5$/kg-$2\times10^7$/kg, and these cells were washed and transfused back to a human body.

Figure 11:
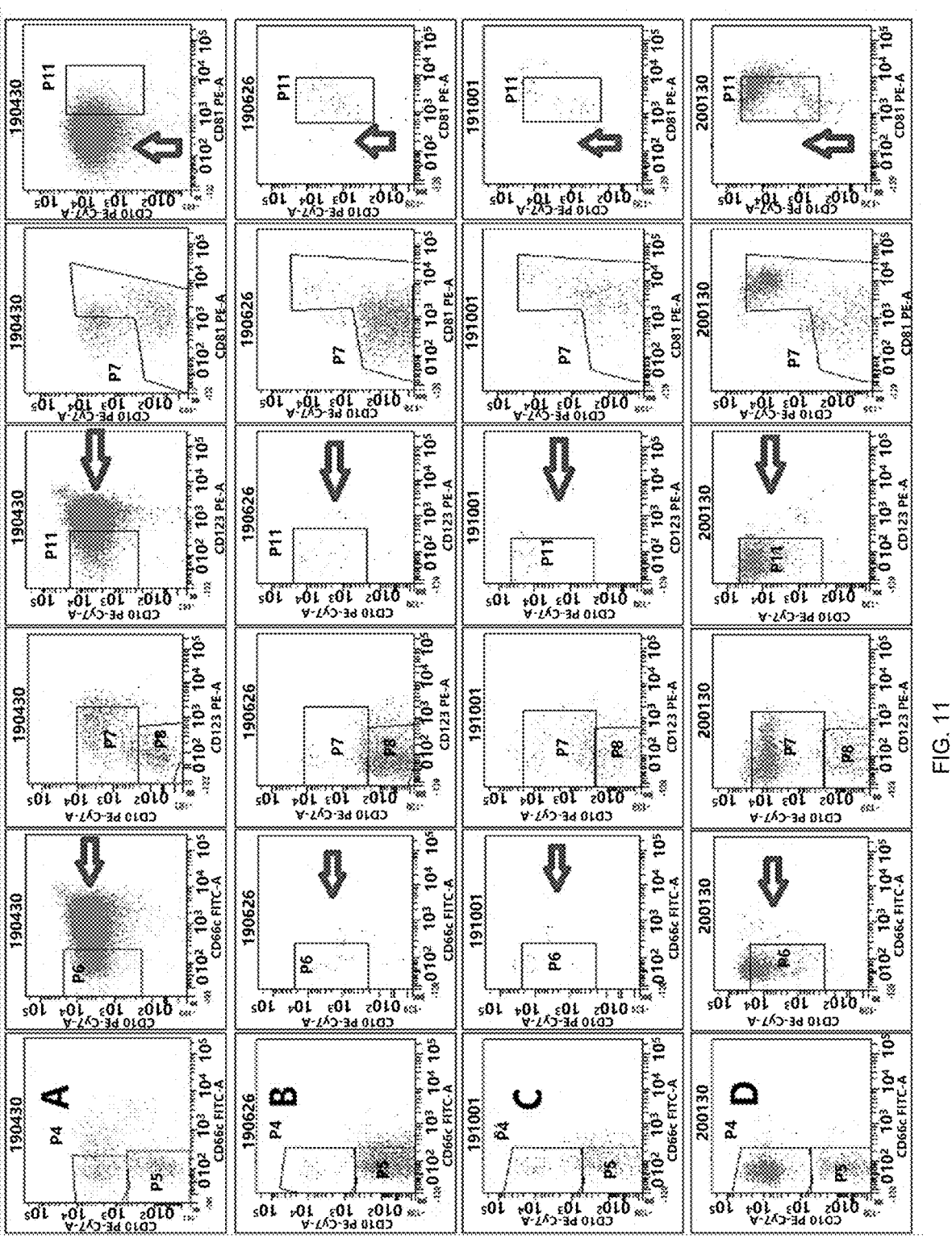
FIG. 11 shows the detection results of minimal residual disease (MRD) of a patient, with acute lymphoblastic leukemia relapsed after bone marrow transplantation, before and after CD19/CD22 dual-target CART infusion according to the present application.

Example 6 Dual-CD19-CD22-CART for Treatment of Patient with Acute Lymphoblastic Leukemia Relapsed after Bone Marrow Transplantation The detection results of minimal residual disease of a patient, with acute lymphoblastic leukemia relapsed after bone marrow transplantation, before and after dual-CD19-CD22-CART infusion are shown in FIG. 11, in which A shows the detection results of minimal residual disease before the treatment with dual-CD19-CD22-CART (the patient shows high expression of CD66c and CD123 and low expression of CD81 in leukemia cells), with the arrow pointing to the leukemia cells; and B, C and D shows the detection results of minimal residual disease after the treatment with dual-CD19-CD22-CART. It can be seen that the leukemia cells disappear for 9 months and are still in a complete remission status.

Figure 12:
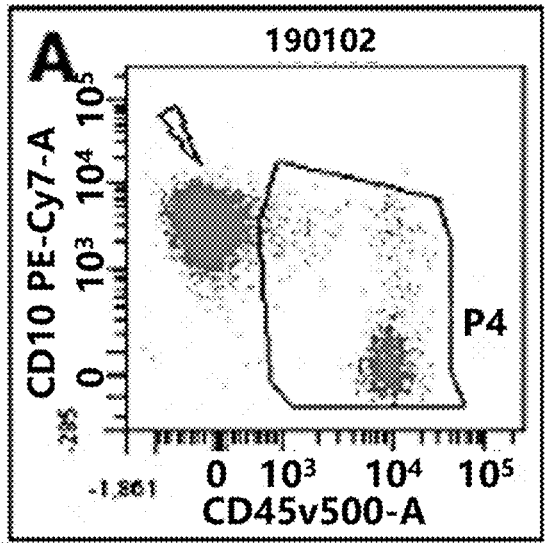
FIG. 12 shows the detection results of minimal residual disease (MRD) of a patient, with multiple relapsed acute lymphoblastic leukemia, before and after CD19/CD22/CD20 triple-target CART infusion according to the present application.
Figure 12:
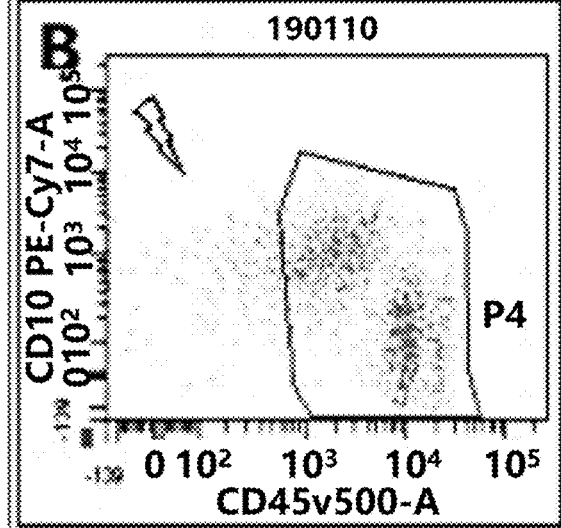
Figure 12:
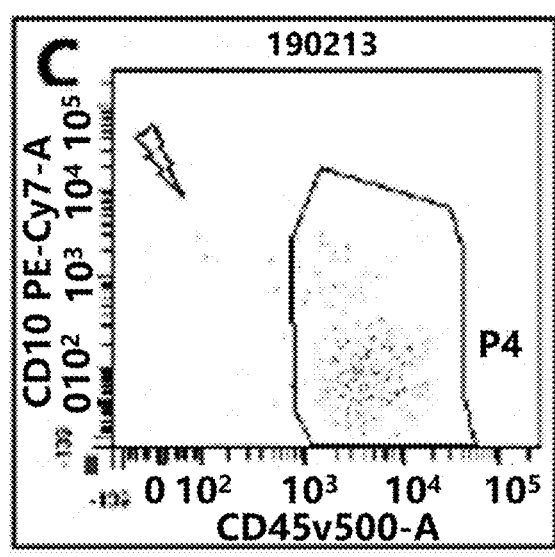
Figure 12:
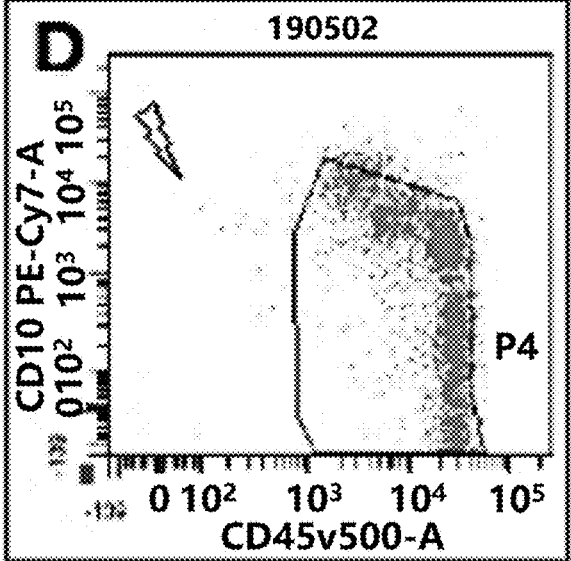
Figure 12:
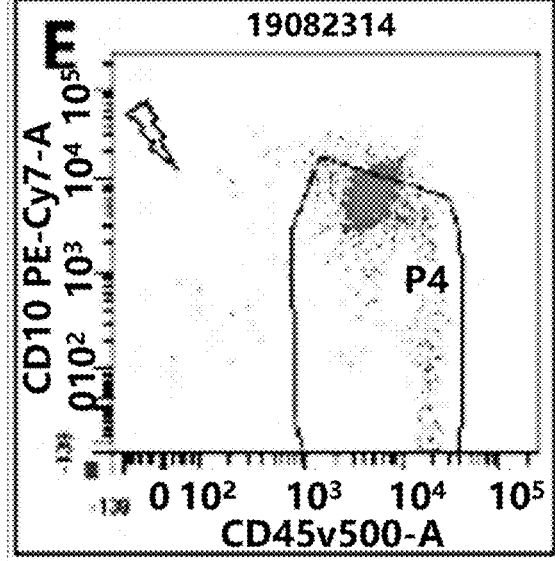

Example 7 Tri-CD19-CD22-CD20-CART for Treatment of Patient with Multiple Relapsed Acute Lymphoblastic Leukemia The detection results of minimal residual disease of a patient, with multiple relapsed acute lymphoblastic leukemia, before and after tri-CD19-CD22-CD20-CART infusion are shown in FIG. 12, in which A shows the detection results of minimal residual disease before the treatment with tri-CD19-CD22-CD20-CART (the patient shows low expression of CD45 in leukemia cells), with the arrow pointing to the leukemia cells; and B, C and D shows the detection results of minimal residual disease after the treatment with tri-CD19-CD22-CD20-CART. It can be seen that the leukemia continues to disappear.

Figure 13:
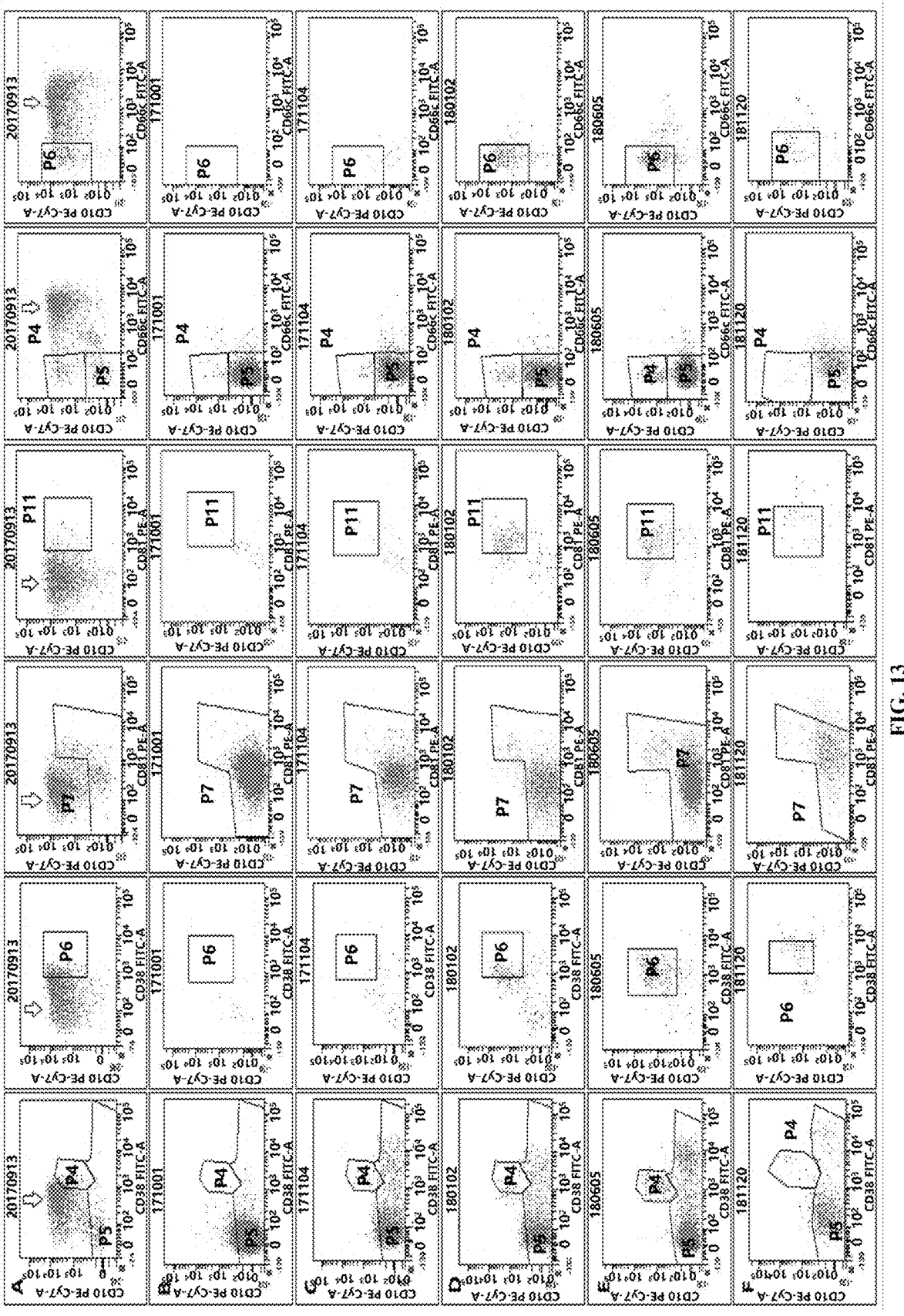
FIG. 13 shows the detection results of minimal residual disease (MRD) of a patient, with acute lymphoblastic leukemia relapsed in both bone marrow and main center, before and after CD19/CD22 dual-target CART infusion according to the present application.

Example 8 Dual-CD19-CD22-CART for Treatment of Patient with Acute Lymphoblastic Leukemia Relapsed in Both Bone Marrow and Main Center The detection results of minimal residual disease of a patient, with acute lymphoblastic leukemia relapsed in both bone marrow and main center, before and after dual-CD19-CD22-CART infusion are shown in FIG. 13, in which A shows the detection results of minimal residual disease before the treatment with dual-CD19-CD22-CART (the patient shows low expression of CD38 and CD81 in leukemia cells), with the arrow pointing to the leukemia cells; and B, C, D, E and F shows the detection results of minimal residual disease after the treatment with dual-CD19-CD22-CART. It can be seen that the leukemia cells disappear for 14 months and are still in a complete remission status.

Example 9 Tri-CD19-CD22-CD20-CART for Treatment of Burkitt Lymphoma Patient

Figure 14:
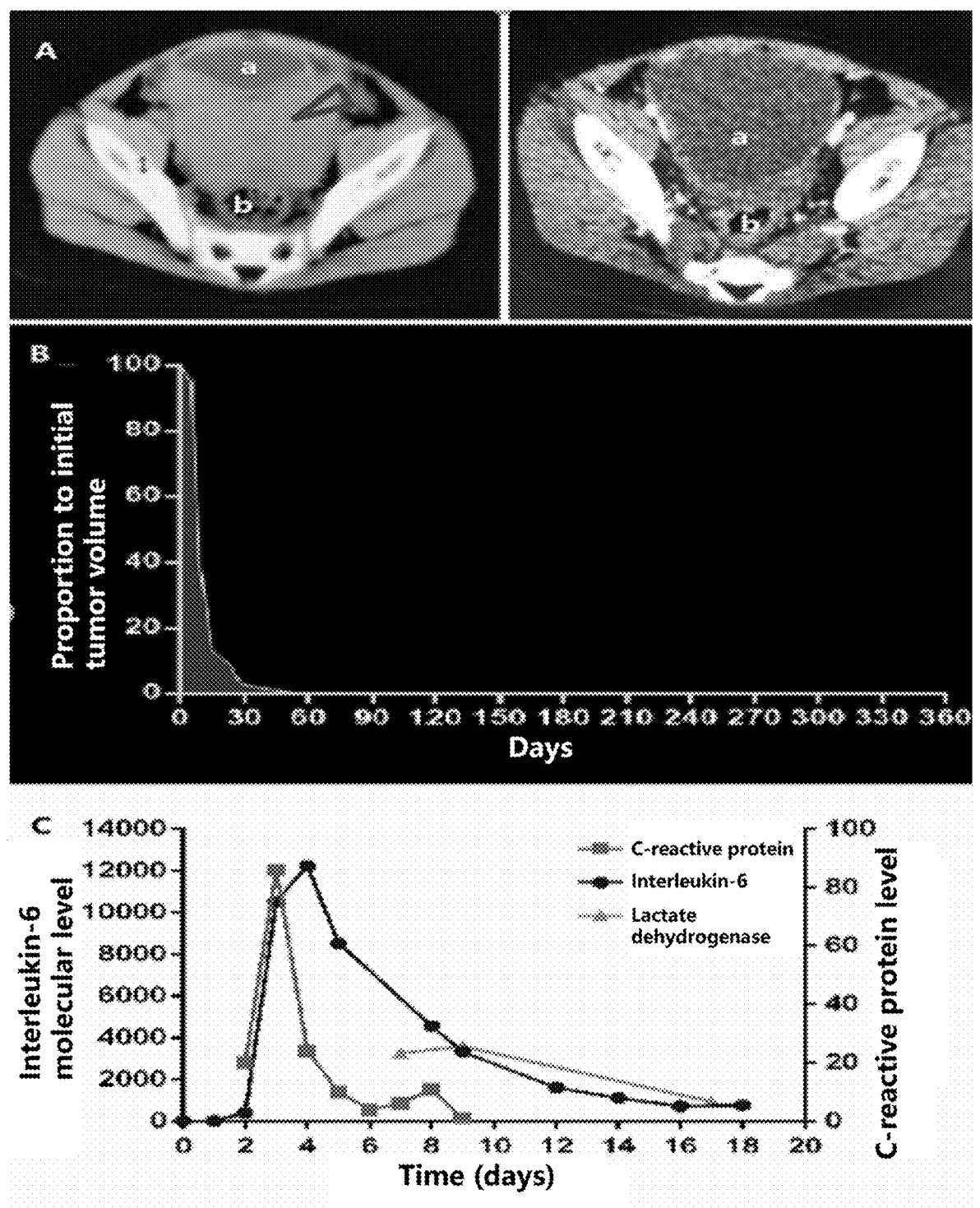
FIG. 14 shows the condition of a Burkitt lymphoma patient treated with CD19/CD22/CD20 triple-target CART according to the present application.

The condition of a Burkitt lymphoma patient treated with tri-CD19-CD22-CD20-CART is shown in FIG. 14. In FIG. 14, A shows the tumor changes before and after treatment. It can be seen that a tumor with the size of 6.6 cm between the bladder (marked as a in the figure) and the rectum (marked as b in the figure) of the patient before treatment completely disappears after treatment; B shows the tumor changes observed continuously for one year, in which the tumor basically disappears after more than 1 month without relapse; and C shows the changes of C-reactive protein, cytokines (mainly interleukin-6) and lactate dehydrogenase or the like in the patient during the treatment.

Figure 15:
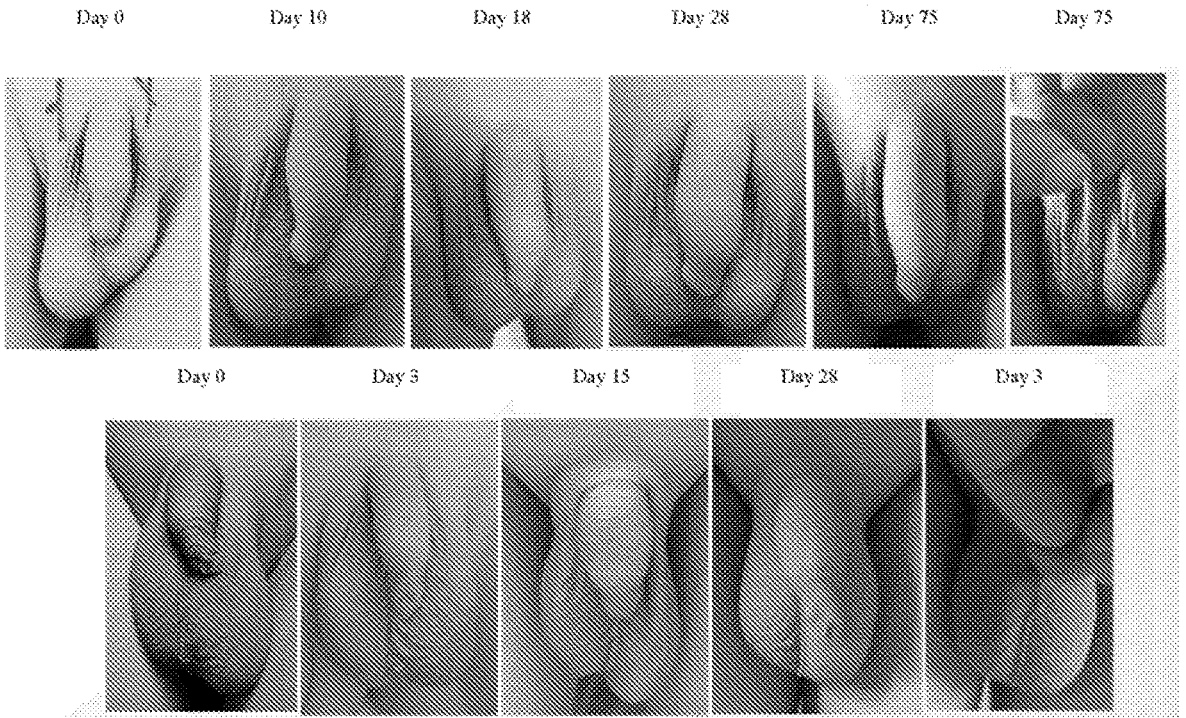
FIG. 15 shows the conditions of two patients, with acute lymphoblastic leukemia relapsed in testicles, treated with the CD19/CD22 dual-target CART according to the present application.

Example 10 Dual-CD19-CD22-CART for Treatment of Patients with Acute Lymphoblastic Leukemia Relapsed in Testicles The conditions of two patients, with acute lymphoblastic leukemia relapsed in testicles, after receiving dual-CD19-CD22-CART treatment are shown in FIG. 15, in which the upper and lower columns show the conditions of the two patients, with acute lymphoblastic leukemia relapsed in testicles, treated with the dual-CD19-CD22-CART, respectively. It can be seen that, after the injection on Day 0, the leukemia-infiltrated testicles of the patients gradually shrink to a normal size. After pathological biopsy, no leukemia cells were seen after the treatment with dual-CD19-CD22-CART.

Example 11 Dual-GD2-B7H3-CART for Treatment of Neuroblastoma Patient

Figure 16A:
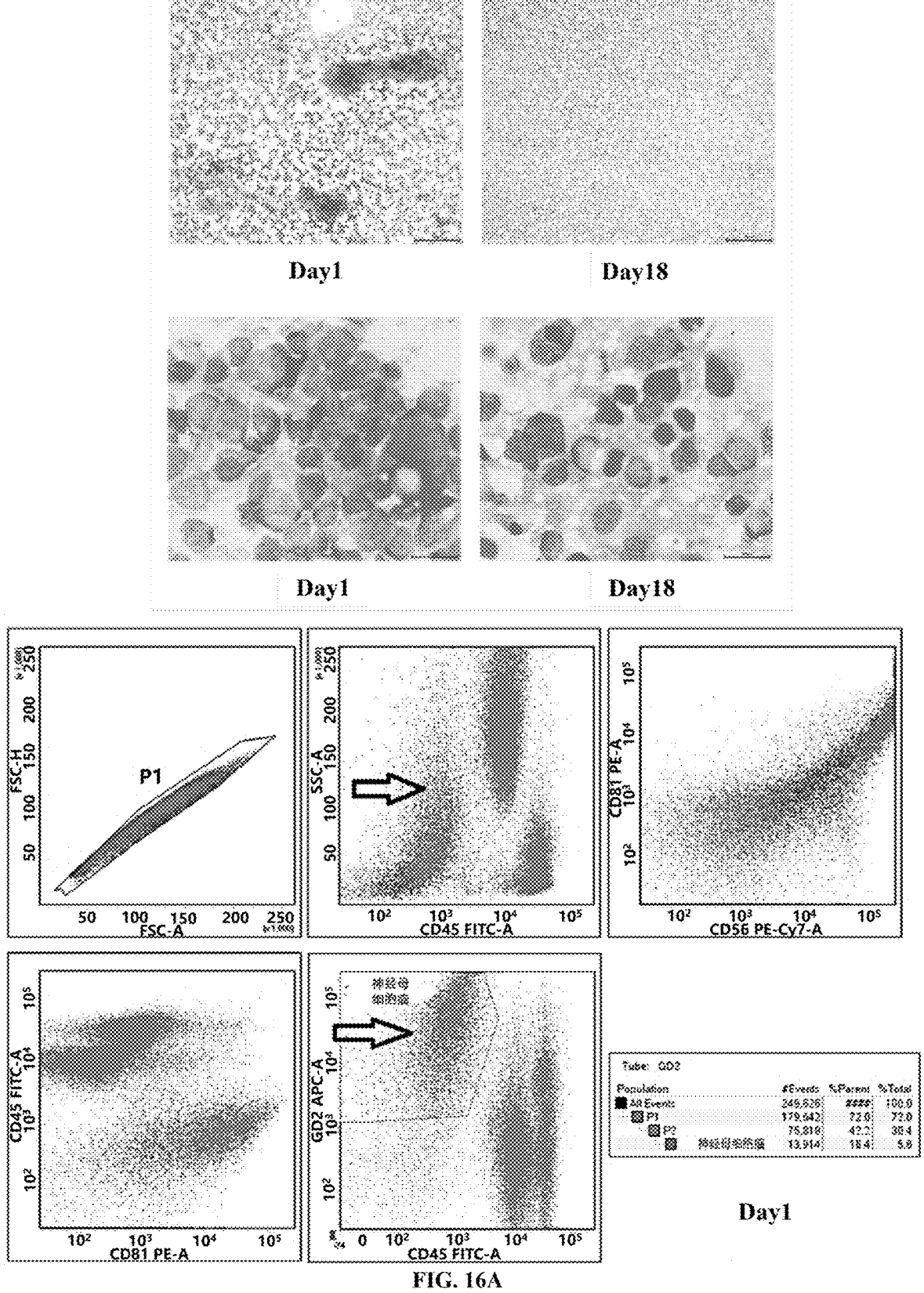
FIG. 16 shows the treatment results of a neuroblastoma patient receiving GD2/B7H3 dual-target CART according to the present application.
Figure 16B:
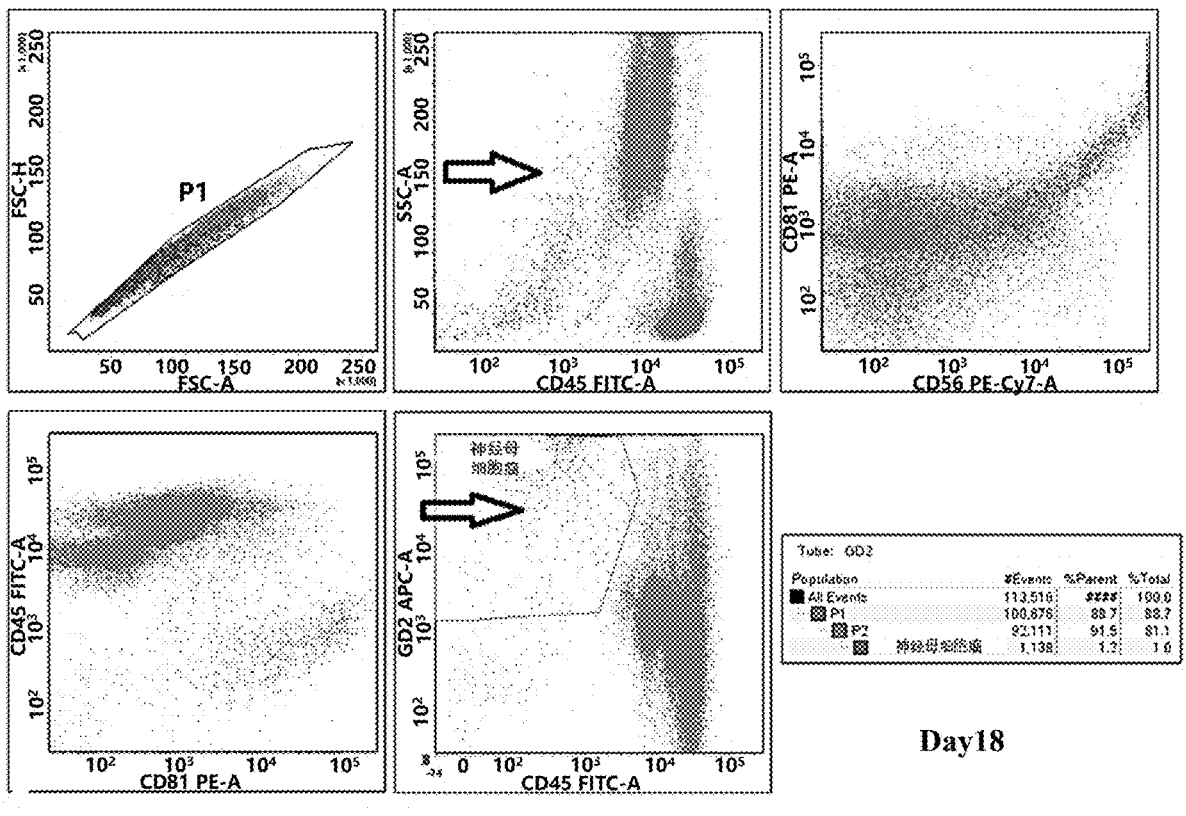

The conditions of a neuroblastoma patient after receiving dual-GD2-B7H3-CART treatment are shown in FIG. 16, in which A shows the results of bone marrow smear under a low-power microscope before and after treatment, and it can be seen that tumor cells in the bone marrow are significantly reduced after 18 days of treatment; B shows the results of bone marrow smear under a high-power microscope before and after treatment, and it can be seen that tumor cells in the bone marrow are significantly reduced after 18 days of treatment; and C and D show the flow cytometry results before and after treatment, where tumor cells in the bone marrow decrease from 60% before treatment to 1.2%.

Figure 17A:
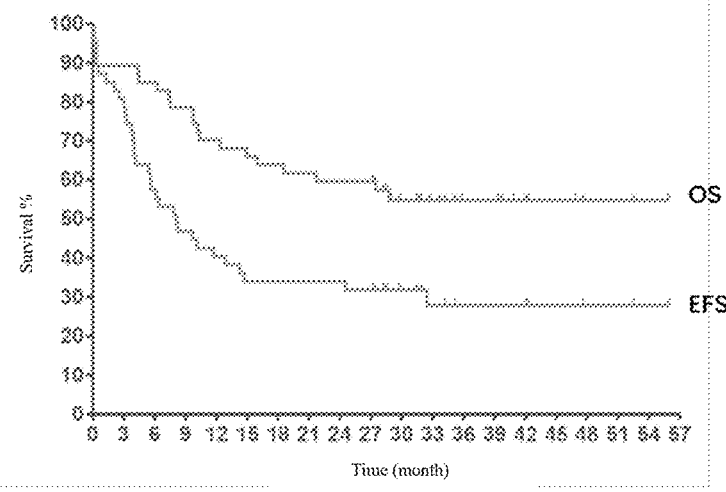
FIG. 17A shows the therapeutic efficacy of single-target CD19-CART.

Example 12 Disease Remission Rate, Event-free Survival and Overall Survival of Clinically Treated Patients 1. From March, 2017 to August, 2019, 47 child patients with relapsed and refractory acute lymphoblastic leukemia (ALL) successively received CD19 single-target CART treatment, with an average observation time of 23.8 months and a maximum observation time of 55.5 months. After receiving the Single-CD19-CART treatment, the negative conversion rate of minimal residual disease was 97.9% (47/48); the primary disease relapsed in 29 patients, and the second tumor occurred to 1 patient (MLL-AF4-positive mixed lineage leukemia relapse before Single-CD19-CART treatment); and the relapse rate of the disease was 38.2% (21/55). Among the 29 patients with relapsed primary disease, 19 patients had CD19-positive relapse and 10 patients had CD19-negative relapse, with overall 2-year event-free survival of 34.0% and overall 3-year survival of 59.6%, as shown in FIG. 17A.

Figure 17B:
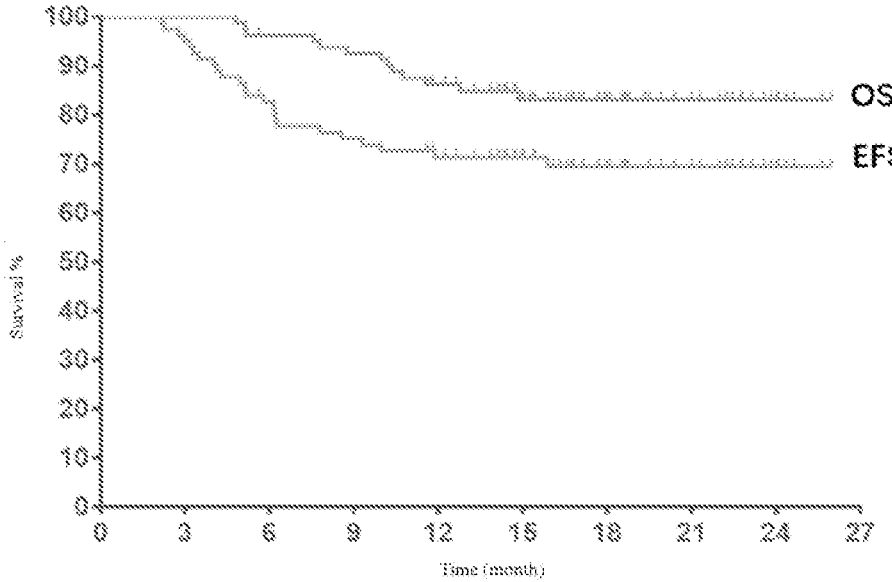
FIG. 17B shows the therapeutic efficacy of dual-target CD19/CD22-CART.

2. From September, 2019 to October, 2020, 81 child patients with relapsed and refractory acute lymphoblastic leukemia received treatment with CD19-CD22 duoCART New19CRE22-CAR v3, with an average observation time of 16.4 months and a maximum observation time of 25.9 months. One patient died from CRES without primary disease evaluation. Among other patients receiving the CART treatment, the negative conversion rate of minimal residual disease was 98.8% (80/81); and the primary disease relapsed in 22 patients, including 1 patient with unknown leukemia phenotype after relapse, 1 patient with CD19–/CD22– relapse, 4 patients with CD19–/CD22+ relapse, and 14 patients with CD19+/CD22+ relapse. The disease relapse rate was 27.2%, mainly including CD19+ relapse. The overall 1-year event-free survival was 71.4%, and the overall 1-year survival was 86.3%, as shown in FIG. 17B. The analysis shows that the therapeutic efficacy of CD19-CD22 dual-target CART is much higher than that of single CD19 target, with a P value being statistically significant.

Figure 17C:
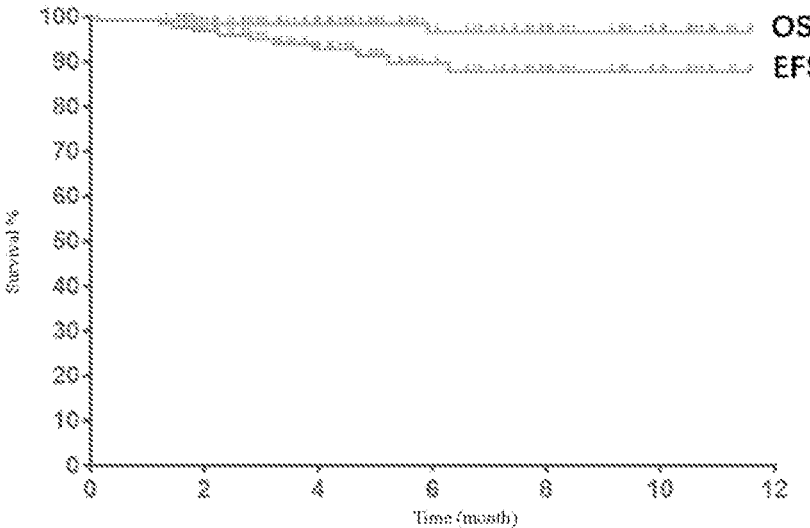
FIG. 17C shows the therapeutic efficacy of dual-target CD19/CD22-CART.

3. From November, 2020 to November, 2021, 132 child patients with relapsed and refractory acute lymphoblastic leukemia received the CART treatment with CD19-CD22 duoCART (III-5) and CD22-CD19 duoCART (III-6), with an average observation time of 5.3 months and a maximum observation time of 11.6 months. No patients had CRS or CRES death, the negative conversion rate of minimal residual disease was 100.0% (132/132), and the primary disease relapsed in 8 patients, including 5 patients with CD19–/CD22+ relapse and 3 patients with CD19+/CD22+ relapse. The relapse rate of the disease was 6.1%, and the relapse rate of CD19+ was greatly reduced. The 6-month event-free survival was 89.7% and the overall 6-month survival was 96.7%, as shown in FIG. 17C. The analysis shows that the therapeutic efficacy of CD19-CD22 duoCART (III-5) and CD22-CD19 duoCART (III-6) is further superior to that of CD19-CD22 duoCART New19CRE22-CAR v3, with a P value being statistically significant.

Figure 17D:
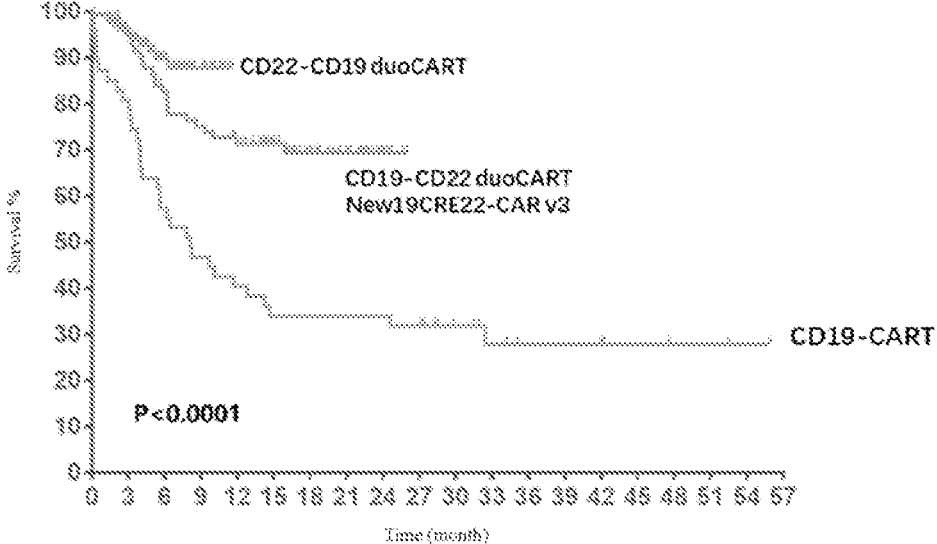
FIG. 17D shows the comparison of clinical efficacy across different constructs.

In terms of the analysis of CD19 single-target construction and CD19 and CD22 dual-target construction, CD19-CD22 duoCART (III-5) and CD22-CD19 duoCART (III-6) (both mainly differing in the sequential order of ScFvs of CD19 and CD22, without significant difference in vitro and in vivo) show the best therapeutic efficacy, as shown in FIG. 17D.

The invention claimed is:

1. A nucleic acid molecule expressing at least two types of chimeric antigen receptors (CAR), comprising a nucleic sequence encoding a leader peptide, a nucleic acid sequence encoding a first antigen-binding domain, a nucleic sequence encoding a first non-antigen binding function domain, a nucleic sequence encoding a cleavable peptide, a nucleic sequence encoding a leader sequence, a nucleic acid sequence encoding a second antigen-binding domain, and a nucleic sequence encoding a first non-antigen binding function domain;

wherein said non-antigen binding function domain comprises a hinge region, a transmembrane region, a co-stimulatory domain and an intracellular signaling domain, wherein the nucleic acid molecule comprises a nucleotide sequence as set forth in SEQ ID NO: 83 or SEQ ID NO: 84.

2. The nucleic acid molecule according to claim 1, comprising a nucleic acid sequence encoding a promoter.

3. The nucleic acid molecule according to claim 2, wherein said promoter is selected from the group consisting of: EF1α, CMV, MSCV, and UbC.

4. The nucleic acid molecule according to claim 1, comprising a nucleic acid sequence encoding WPRE, wherein said nucleic acid sequence encoding WPRE is located downstream of said nucleic acid sequence encoding the non-antigen-binding function domain.

5. The nucleic acid molecule according to claim 1, comprising a nucleic acid sequence encoding a backbone vector, wherein said nucleic acid sequence encoding the backbone vector is located upstream of said nucleic acid sequence encoding the promoter.

6. The nucleic acid molecule according to claim 5, wherein said backbone vector comprises a viral vector.

7. The nucleic acid molecule according to claim 5, wherein said backbone vector comprises an HIV packaging vector.

8. The nucleic acid molecule according to claim 1, comprising a 5' LTR sequence located at a 5'-terminal of said nucleic acid molecule, and a 3' LTR sequence located at a 3'-terminal of said nucleic acid molecule.

9. The nucleic acid molecule according to claim 1, which expresses two types of chimeric antigen receptors.

10. A plasmid, comprising the nucleic acid molecule of claim 1.

11. The plasmid according to claim 10, comprising a viral plasmid.

12. A cell, comprising the nucleic acid molecule of claim 1.

13. The cell according to claim 12, comprising a cell selected from the group consisting of: a T cell and a NK cell.

* * * * *